:

US008367349B2

(12) United States Patent
Dzamko et al.

(10) Patent No.: US 8,367,349 B2
(45) Date of Patent: Feb. 5, 2013

(54) METHODS FOR IDENTIFYING MODULATORS OF LRRK2

(75) Inventors: Nicolas Dzamko, Dundee (GB); Dario Alessi, Dundee (GB); R. Jeremy Nichols, Dundee (GB)

(73) Assignee: Medical Research Council (GB)

( * ) Notice: Subject to any disclaimer, the term of this patent is extended or adjusted under 35 U.S.C. 154(b) by 0 days.

(21) Appl. No.: 12/828,674

(22) Filed: Jul. 1, 2010

(65) Prior Publication Data

US 2011/0256062 A1    Oct. 20, 2011

Related U.S. Application Data

(63) Continuation-in-part of application No. 12/763,005, filed on Apr. 19, 2010, now abandoned.

(30) Foreign Application Priority Data

Apr. 19, 2010   (GB) .................................... 1006502.7
Jun. 30, 2010   (GB) .................................... 1011010.4

(51) Int. Cl.
    *G01N 33/566*    (2006.01)
(52) U.S. Cl. .......................................... 435/7.1; 436/501
(58) Field of Classification Search .................... None
     See application file for complete search history.

(56) References Cited

U.S. PATENT DOCUMENTS

2009/0004112 A1*  1/2009  Abeliovich ................... 424/9.2
2009/0142784 A1*  6/2009  Alessi et al. .................... 435/15

FOREIGN PATENT DOCUMENTS

| GB | 2 463 646 A | 3/2010 |
| WO | 2008/091799 A2 | 7/2008 |
| WO | 2008/122789 A2 | 10/2008 |
| WO | 2010/031988 A2 | 3/2010 |

OTHER PUBLICATIONS

Alegre-Abarrategui et al. "LRRK2 regulates autophagic activity and localizes to specific membrane microdomains in a novel human genomic reporter cellular model." Human Molecular Genetics, 2009, vol. 18, No. 21, pp. 4022-4034.
Anand et al. "LRRK2 in Parkinson's disease: biochemical functions." FEBS Journal 276 (2009) 6428-6435.
Anand et al. "Investigation of leucine-rich repeat kinase 2: Enzymological properties and novel assays." FEBS Journal 276 (2009) 466-478.
Bain et al. "The selectivity of protein kinase inhibitors: a further update." Biochem. J. (2007) 408, 297-315.
Berg et al. "14-3-3 Proteins in the Nervous System." Nat Rev Neurosci. 4, 752-762, 2003.
Biskup et al. "Zeroing in on LRRK2-Linked Pathogenic Mechanisms in Parkinson's Disease." Biochim Niophys Acta., 2009; 1792(27): 625-633.

Chen et al. "Interaction of Akt-Phosphorylated Ataxin-1 with 14-3-3 Mediates Neurodegeneration in Spinocerebellar Ataxia Type 1." Cell, vol. 113, 457-468, 2003.
Covy et al. "Identification of Compounds that Inhibit the Kinase Activity of Leucine-rich Repeat Kinase 2." Biochem Biophys Res Comm. 2009; 378(3): 473-477.
Dzamko et al. "Inhibition of LRRK2 kinase activity leads to dephosphorylation of Ser910/Ser935, disruption of 14-3-3 binding and altered cytoplasmic localisation." Biochem J. manuscript BJ20100784, Jul. 21, 2010.
Gloeckner et al. "The Parkinson disease-associated protein kindase LRRK2 exhibits MAPKKK activity and phosphorylates MKK3/6 and MKK4/7, in vitro." Journal of Neurochemistry, 2009, 109, 959-968.
Gloeckner et al. "Phosphopeptide Analysis Reveals Two Discrete Clusters of Phosphorylation in the N-Terminal and the Roc Domain of the Parkinson-Disease Associated Protein Kinase LRRK2." Journal of Proteome Research, 2010, vol. 9, No. 4, p. 1738-1745.
Greggio et al. "Kinase activity is required for the toxic effects of mutant LRRK2/dardain." Neurobiology of Disease 23 (2006) 329-341.
Greggio et al. "The Parkinson Disease-associated Leucine-rich Repeat Kinase 2 (LRRK2) is a Dimer that Undergoes Intramolecular Autophosphorylation." The Journal of Biological Chemistry, vol. 283, No. 24, p. 16906-19914, 2008.
Greggio et al. "The Parkinson's disease kinase LRRK2 autophosphorylates its GTPase domain at multiple sites." Biochemical and Biophysical Research Communications 389 (2009) 449-454.
Greggio et al. "Leucine-rich repeat kinase 2 mutations and Parkinson's disease: three questions." ASN Neuro 1(1): 13-24, 2009.
Hausser et al. "Phospho-specific binding of 14-3-3 proteins to phosphatidylinositol 4-kinase III beta protects from dephosphorylation and stabilizes lipid kinase activity." J Cell Sci. 119, 3613-3621, 2006.
Healy et al. "Phenotype, genotype, and worldwide genetic penetrance of LRRK2-associated Parkinson's disease: a case-control study." Lancet Neurol. 7, 583-590, 2008.
Hutchins et al. "Dephosphorylation of the inhibitory phosphorylation site S287 in *Xenopus* Cdc25C by protein phosphatase-2A is inhibited by 14-3-3 binding." FEBS Lett. 528, 267-271, 2002.
Jaleel et al. "LRRK2 phosphorylates moesin at threonine-558: characterization of how Parkinson's disease mutants affect kinase activity." Biochem J. 405, 307-317, 2007.
Kamikawaji et al. "Identification of the Autophorphorylation Sites of LRRK2." Biochemistry, vol. 48, p. 10963-10975, 2009.
Lesage et al. "LRRK2 exon 41 mutations in sporadic Parkinson disease in Europeans." Arch Neurol. 64, 425-430, 2007.

(Continued)

Primary Examiner — John Ulm
(74) Attorney, Agent, or Firm — K&L Gates LLP; Louis C. Cullman; Michelle Glasky Bergman

(57) ABSTRACT

A method for assessing the effect of a test compound on LRRK2 in a cell-based system, the method comprising the steps of a) assessing the effect of exposing the cell-based system comprising LRRK2 to the test compound on the phosphorylation state of Ser910 and/or Ser935 of the LRRK2; and/or b) assessing the effect of exposing the cell-based system comprising LRRK2 to the test compound on the binding of the LRRK2 to a 14-3-3 polypeptide. The method may comprise or further comprise the step of assessing the effect of exposing the cell-based system comprising LRRK2 to the test compound on the subcellular location of LRRK2. The method is considered to be useful in assessing the effect of putative LRRK2 inhibitors in cell based systems, including in vivo systems.

14 Claims, 24 Drawing Sheets

OTHER PUBLICATIONS

Mackintosh "Dynamic interactions between 14-3-3 proteins and phosphoproteins regulate diverse cellular processes." Biochem J. vol. 381, p. 329-342, 2004.

Mata et al. "LRRK2 in Parkinson's disease: protein domains and functional insights." Trends Neurosci. 29, 286-293, 2006.

Moorhead et al. "Phosphorylation-dependent interactions between enzymes of plant metabolism and 14-3-3 proteins." Plant J. 18, 1-12, 1999.

Nichols et al. "Substrate specificity and inhibitors of LRRK2, a protein kinase mutated in Parkinson's disease." Biochem J. 424, 47-60, 2009.

Nichols et al. "14-3-3 binding to LRRK2 is disrupted by multiple Parkinson's disease associated mutations and regulates cytoplasmic localisation." Biochem J manuscript BJ20100483, Jul. 19, 2010.

Paisan-Ruiz et al. "Cloning of the gene containing mutations that cause PARK8-linked Parkinson's disease." Neuron. 44, 595-600, 2004.

Paisan-Ruiz et al. "Comprehensive analysis of LRRK2 in publicly available Parkinson's disease cases and neurologically normal controls." Hum Mutat. 29, 485-490, 2008.

Smith et al. "Leucine-rich repeat kinase 2 (LRRK2) interacts with parkin, and mutant LRRK2 induces neuronal degeneration." Proc Natl Acad Sci U S A. 102, 18676-18681, 2005.

Tong et al. "R1441C mutation in LRRK2 impairs dopaminergic neurotransmission in mice." Proc Natl Acad Sci U S A. 106, 14622-14627, 2009.

Yaffe et al. "The structural basis for 14-3-3:phosphopeptide binding specificity." Cell. 91, 961-971, 1997.

Zanivan et al. "Solid tumor proteome and phosphoproteome analysis by high resolution mass spectrometry." J Proteome Res. 7, 5314-5326, 2008.

Zimprich et al. "Mutations in LRRK2 cause autosomal-dominant parkinsonism with pleomorphic pathology." Neuron. 44, 601-607, 2004.

Deng et al. "Characterization of a selective inhibitor of the Parkinson's disease kinase LRR K2." Nature Chemical Biology, vol. 7, Mar. 6, 2011, p. 203-205.

Moore et al. "The biology and pathobiology of LRRK2: Implications for Parkinson's disease." Parkinsonism and Related Disorders, vol. 14, Jul. 1, 2008, p. S92-S98.

International Search Report for PCT/GB2011/050776.

* cited by examiner

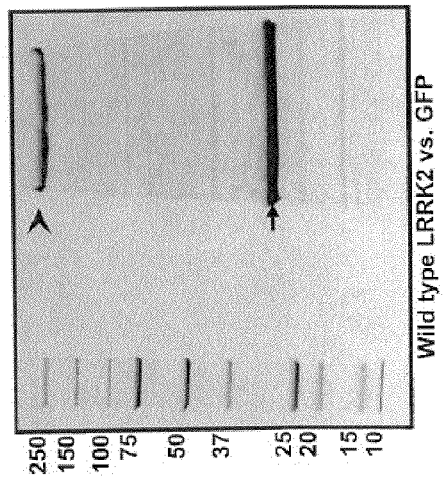
Figure 1A
Figure 1C
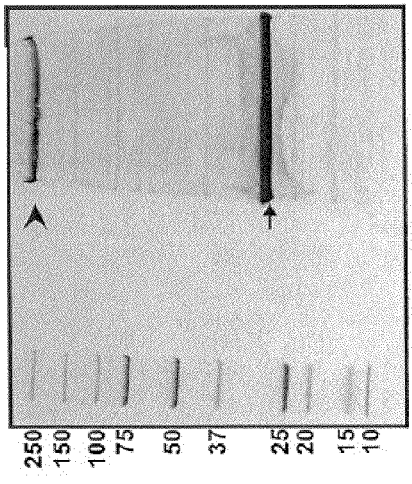
Figure 1B
Figure 1D

```
         910                     935
DSEGSEGSFLVKKKSNSISVGEFY-RDAVLQRCSPNLQRHSNSLGPIFDHEDL Homo sapiens
DSEGSEGSFLVKRKSNSISVGEFY-RDAVLQRCSPNLQRHSNSLGPIFDHEDL Pan troglodytes
DSEGSESSFLVKRKSNSISVGEVY-RDLALQRYSPNAQRHSNSLGPVFDHEDL Mus musculus
DSEGSESSFLVKKKSNSVSVGEVY-RDLALQRCSPNAQRHSSSLGPVFDHEDL Rattus norvegicus
DSEGSEGSFLVKTKSNSISVGEFY-QDPALQRCSPNLQRHSSSLGPIFDHEDL Bos taurus
DSEGSEGSFLVKRKSNSISVGEFY-HDRALQRCSPNLQRHGNSLGPIFDHEDF Canis l. familiaris
DSEGSEGSVFRKKKSNSIAVADLHCRELAFQRGSPTLPRHSYSVGPGSDYEPL Gallus gallus
```

Figure 3

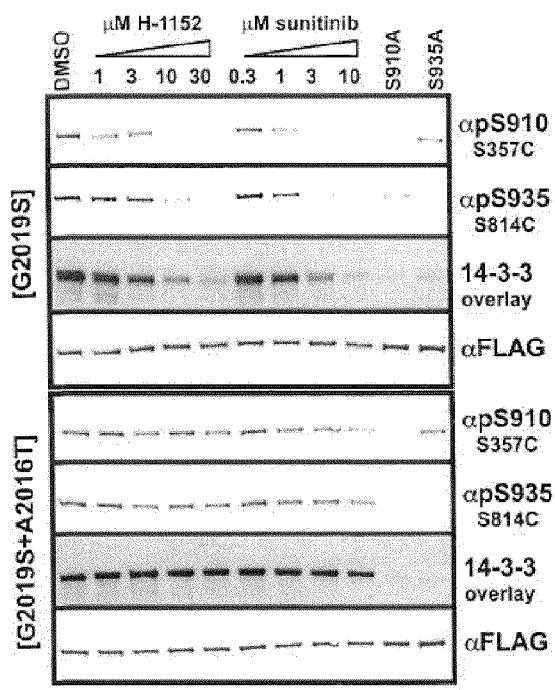
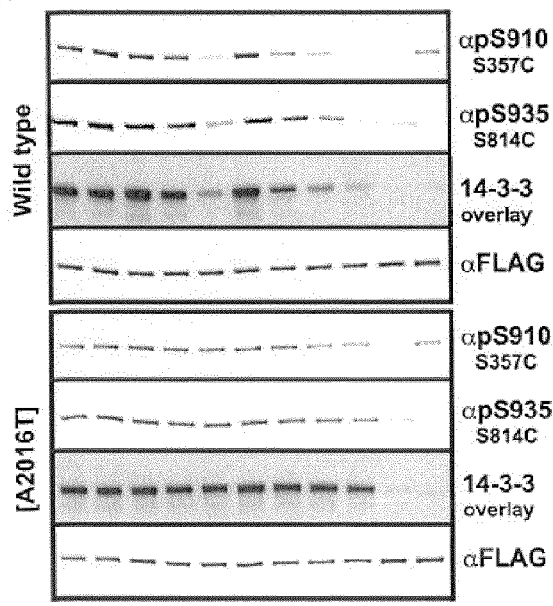
Figure 5

A.
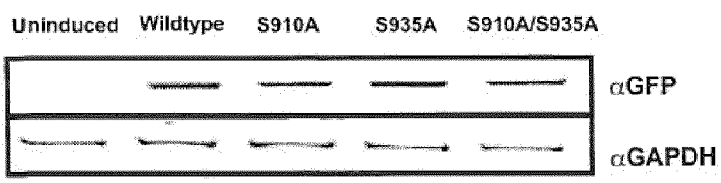
B.
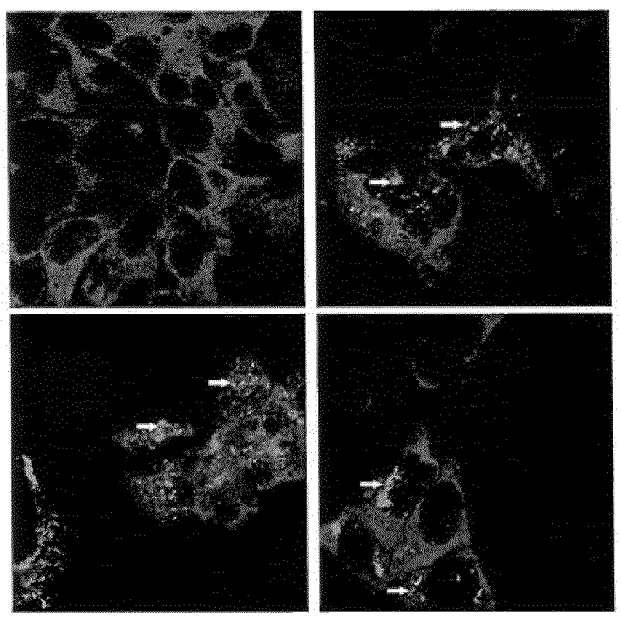
Figure 8

| Mutant | Kinase activity | pSer910/pSer935 | 14-3-3 binding | Localization | Group | |
|---|---|---|---|---|---|---|
| WT | + | ++ | ++ | Diffuse | | |
| D2017A | 0 | ++ | ++ | Diffuse | | |
| E10K | + | ++ | ++ | Diffuse | 6 | |
| A211V | + | ++ | ++ | Diffuse | 6 | |
| E334K | + | ++ | ++ | Diffuse | 6 | |
| K544E | + | ++ | ++ | Diffuse | 6 | |
| M712V | + | + | + | Diffuse | 3 | *** |
| P755L | + | ++ | ++ | Diffuse | 6 | |
| R793M | + | ++ | ++ | Diffuse | 6 | |
| Q930R | + | ++ | ++ | Diffuse | 6 | |
| S973N | + | ++ | ++ | Diffuse | 6 | |
| R1067Q | + | ++ | ++ | aggregate | 4 | **** |
| S1096C | + | ++ | ++ | Diffuse | 6 | |
| Q1111H | + | ++ | ++ | Diffuse | 6 | |
| I1122V | + | ++ | ++ | Diffuse | 6 | |
| A1151T | + | ++ | ++ | Diffuse | 6 | |
| I1192V | + | ++ | ++ | Diffuse | 6 | |
| S1228T | + | ++ | ++ | Diffuse | 6 | |
| I1371V | + | ++ | ++ | Diffuse | 6 | |
| R1441C | + | + | + | aggregate | 2 | ** |
| R1441G | + | - | - | aggregate | 2 | ** |
| R1441H | + | + | + | aggregate | 2 | ** |
| A1442P | + | + | + | aggregate | 2 | ** |
| R1514Q | + | ++ | ++ | Diffuse | 6 | |
| V1613A | + | ++ | ++ | Diffuse | 6 | |
| R1628P | + | ++ | ++ | Diffuse | 6 | |
| Y1699C | + | - | - | aggregate | 2 | ** |
| R1728H | ++ | ++ | ++ | Diffuse | 1 | * |
| R1728L | + | ++ | ++ | Diffuse | 6 | |
| L1795F | + | + | - | aggregate | 2 | ** |
| M1869T | + | ++ | ++ | Diffuse | 6 | |
| S1874stp | - | - | - | Diffuse | 5 | ***** |
| R1941H | + | ++ | ++ | Diffuse | 6 | |
| Y2006H | + | ++ | ++ | Diffuse | 6 | |
| I2012T | + | ++ | ++ | Diffuse | 6 | |
| G2019S | +++ | ++ | ++ | Diffuse | 1 | * |
| I2020T | + | - | - | aggregate | 2 | ** |
| T2031S | ++++ | ++ | ++ | Diffuse | 1 | * |
| T2141M | + | ++ | ++ | Diffuse | 6 | |
| R2143H | + | ++ | ++ | Diffuse | 6 | |
| T2356I | + | ++ | ++ | Diffuse | 6 | |
| G2385R | + | + | + | Diffuse | 3 | *** |
| L2466H | + | ++ | ++ | Diffuse | 6 | |
| 910/935 | + | - | - | aggregate | | |

Figure 12

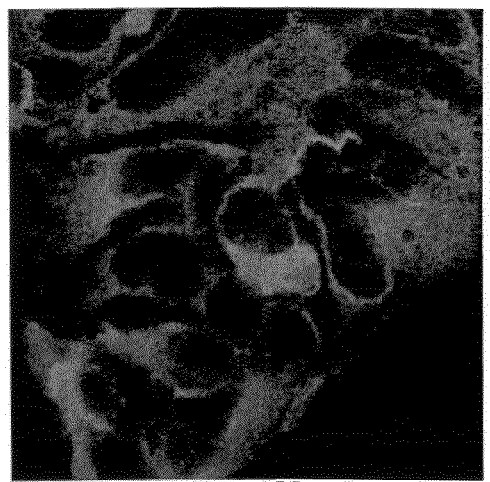
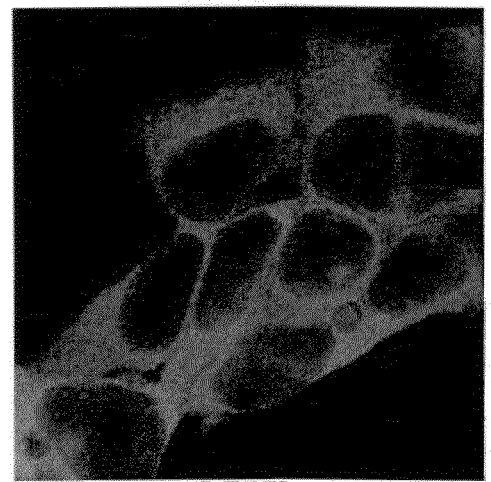
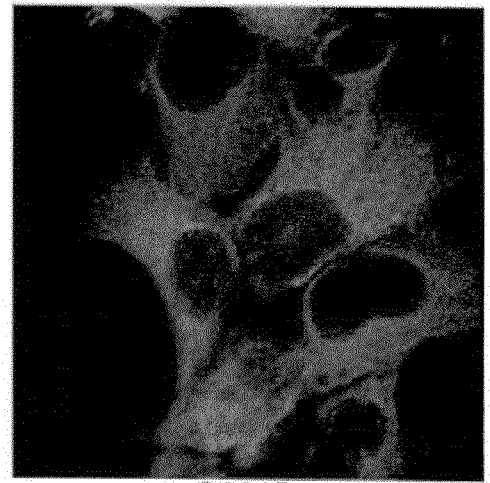
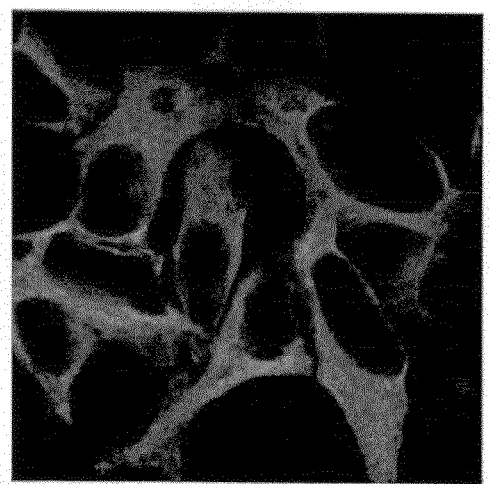
Figure 13 B

   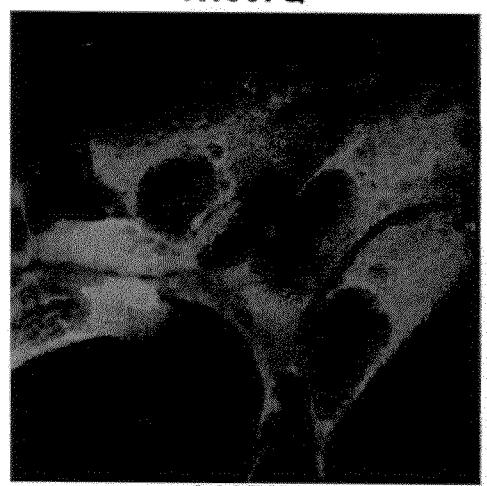  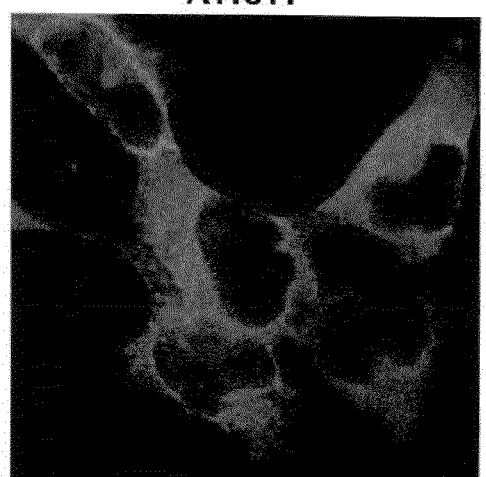
Figure 13 C

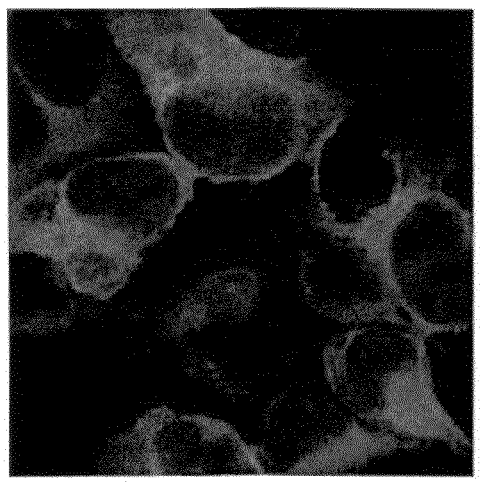 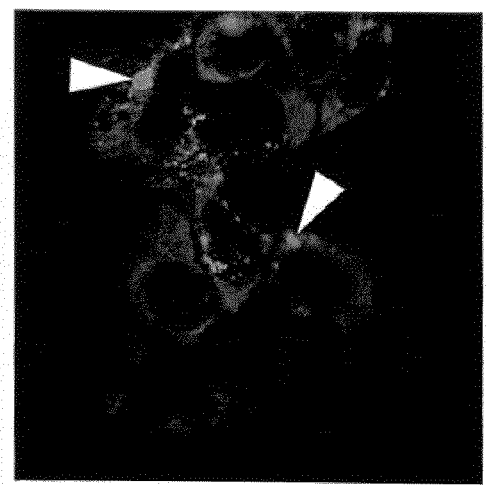
Figure 13 H

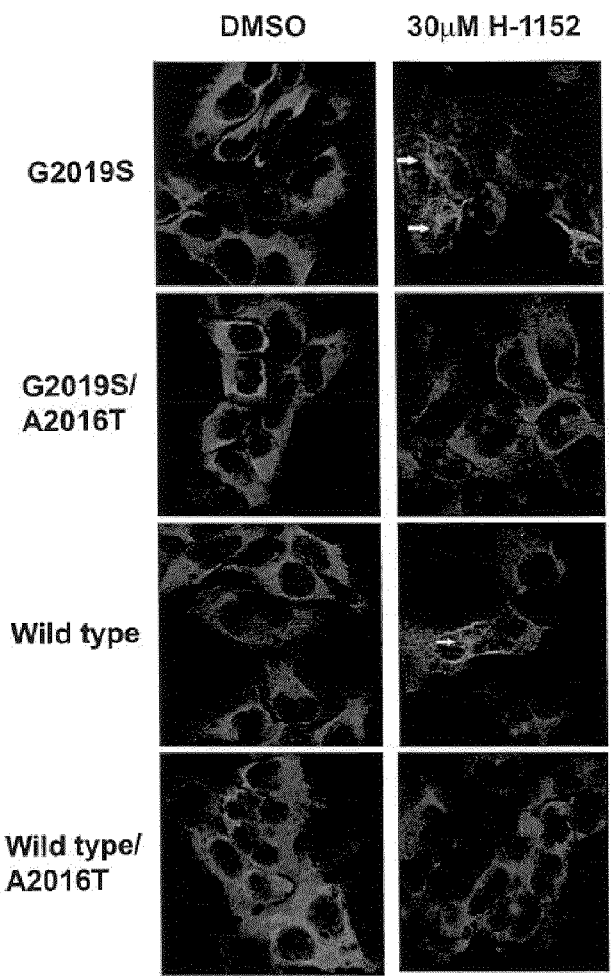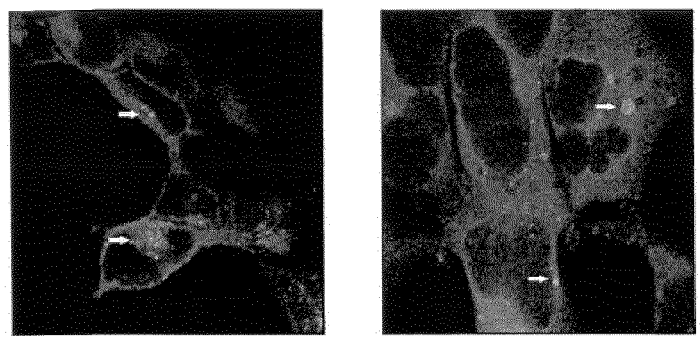
Figure 14

Figure 16

SEQUENCE LISTING

```
<160> NUMBER OF SEQ ID NOS: 45

<210> SEQ ID NO 1
<211> LENGTH: 246
<212> TYPE: PRT
<213> ORGANISM: Homo sapiens

<400> SEQUENCE: 1

Met Thr Met Asp Lys Ser Glu Leu Val Gln Lys Ala Lys Leu Ala Glu
1               5                   10                  15

Gln Ala Glu Arg Tyr Asp Asp Met Ala Ala Ala Met Lys Ala Val Thr
            20                  25                  30

Glu Gln Gly His Glu Leu Ser Asn Glu Glu Arg Asn Leu Leu Ser Val
```

Ala Tyr Lys Asn Val Val Gly Ala Arg Arg Ser Ser Trp Arg Val Ile
            50                  55                  60

Ser Ser Ile Glu Gln Lys Thr Glu Arg Asn Glu Lys Lys Gln Gln Met
 65                  70                  75                  80

Gly Lys Glu Tyr Arg Glu Lys Ile Glu Ala Glu Leu Gln Asp Ile Cys
                 85                  90                  95

Asn Asp Val Leu Glu Leu Leu Asp Lys Tyr Leu Ile Pro Asn Ala Thr
            100                 105                 110

Gln Pro Glu Ser Lys Val Phe Tyr Leu Lys Met Lys Gly Asp Tyr Phe
        115                 120                 125

Arg Tyr Leu Ser Glu Val Ala Ser Gly Asp Asn Lys Gln Thr Thr Val
    130                 135                 140

Ser Asn Ser Gln Gln Ala Tyr Gln Glu Ala Phe Glu Ile Ser Lys Lys
145                 150                 155                 160

Glu Met Gln Pro Thr His Pro Ile Arg Leu Gly Leu Ala Leu Asn Phe
                165                 170                 175

Ser Val Phe Tyr Tyr Glu Ile Leu Asn Ser Pro Glu Lys Ala Cys Ser
            180                 185                 190

Leu Ala Lys Thr Ala Phe Asp Glu Ala Ile Ala Glu Leu Asp Thr Leu
        195                 200                 205

Asn Glu Glu Ser Tyr Lys Asp Ser Thr Leu Ile Met Gln Leu Leu Arg
    210                 215                 220

Asp Asn Leu Thr Leu Trp Thr Ser Glu Asn Gln Gly Asp Glu Gly Asp
225                 230                 235                 240

Ala Gly Glu Gly Glu Asn
                245

<210> SEQ ID NO 2
<211> LENGTH: 246
<212> TYPE: PRT
<213> ORGANISM: Mus musculus

<400> SEQUENCE: 2

Met Thr Met Asp Lys Ser Glu Leu Val Gln Lys Ala Lys Leu Ala Glu
 1               5                  10                  15

Gln Ala Glu Arg Tyr Asp Asp Met Ala Ala Ala Met Lys Ala Val Thr
            20                  25                  30

Glu Gln Gly His Glu Leu Ser Asn Glu Glu Arg Asn Leu Leu Ser Val
        35                  40                  45

Ala Tyr Lys Asn Val Val Gly Ala Arg Arg Ser Ser Trp Arg Val Ile
    50                  55                  60

Ser Ser Ile Glu Gln Lys Thr Glu Arg Asn Glu Lys Lys Gln Gln Met
 65                  70                  75                  80

Gly Lys Glu Tyr Arg Glu Lys Ile Glu Ala Glu Leu Gln Asp Ile Cys
                 85                  90                  95

Asn Asp Val Leu Glu Leu Leu Asp Lys Tyr Leu Ile Leu Asn Ala Thr
            100                 105                 110

Gln Ala Glu Ser Lys Val Phe Tyr Leu Lys Met Lys Gly Asp Tyr Phe
        115                 120                 125

Arg Tyr Leu Ser Glu Val Ala Ser Gly Glu Asn Lys Gln Thr Thr Val
    130                 135                 140

Ser Asn Ser Gln Gln Ala Tyr Gln Glu Ala Phe Glu Ile Ser Lys Lys
145                 150                 155                 160

Glu Met Gln Pro Thr His Pro Ile Arg Leu Gly Leu Ala Leu Asn Phe

```
                    165                 170                 175

Ser Val Phe Tyr Tyr Glu Ile Leu Asn Ser Pro Glu Lys Ala Cys Ser
            180                 185                 190

Leu Ala Lys Thr Ala Phe Asp Glu Ala Ile Ala Glu Leu Asp Thr Leu
        195                 200                 205

Asn Glu Glu Ser Tyr Lys Asp Ser Thr Leu Ile Met Gln Leu Leu Arg
    210                 215                 220

Asp Asn Leu Thr Leu Trp Thr Ser Glu Asn Gln Gly Asp Glu Gly Asp
225                 230                 235                 240

Ala Gly Glu Gly Glu Asn
                245

<210> SEQ ID NO 3
<211> LENGTH: 255
<212> TYPE: PRT
<213> ORGANISM: Homo sapiens

<400> SEQUENCE: 3

Met Asp Asp Arg Glu Asp Leu Val Tyr Gln Ala Lys Leu Ala Glu Gln
1               5                   10                  15

Ala Glu Arg Tyr Asp Glu Met Val Glu Ser Met Lys Lys Val Ala Gly
            20                  25                  30

Met Asp Val Glu Leu Thr Val Glu Glu Arg Asn Leu Leu Ser Val Ala
        35                  40                  45

Tyr Lys Asn Val Ile Gly Ala Arg Arg Ala Ser Trp Arg Ile Ile Ser
    50                  55                  60

Ser Ile Glu Gln Lys Glu Glu Asn Lys Gly Gly Glu Asp Lys Leu Lys
65                  70                  75                  80

Met Ile Arg Glu Tyr Arg Gln Met Val Glu Thr Glu Leu Lys Leu Ile
                85                  90                  95

Cys Cys Asp Ile Leu Asp Val Leu Asp Lys His Leu Ile Pro Ala Ala
            100                 105                 110

Asn Thr Gly Glu Ser Lys Val Phe Tyr Tyr Lys Met Lys Gly Asp Tyr
        115                 120                 125

His Arg Tyr Leu Ala Glu Phe Ala Thr Gly Asn Asp Arg Lys Glu Ala
    130                 135                 140

Ala Glu Asn Ser Leu Val Ala Tyr Lys Ala Ala Ser Asp Ile Ala Met
145                 150                 155                 160

Thr Glu Leu Pro Pro Thr His Pro Ile Arg Leu Gly Leu Ala Leu Asn
                165                 170                 175

Phe Ser Val Phe Tyr Tyr Glu Ile Leu Asn Ser Pro Asp Arg Ala Cys
            180                 185                 190

Arg Leu Ala Lys Ala Ala Phe Asp Asp Ala Ile Ala Glu Leu Asp Thr
        195                 200                 205

Leu Ser Glu Glu Ser Tyr Lys Asp Ser Thr Leu Ile Met Gln Leu Leu
    210                 215                 220

Arg Asp Asn Leu Thr Leu Trp Thr Ser Asp Met Gln Gly Asp Gly Glu
225                 230                 235                 240

Glu Gln Asn Lys Glu Ala Leu Gln Asp Val Glu Asp Glu Asn Gln
                245                 250                 255

<210> SEQ ID NO 4
<211> LENGTH: 255
<212> TYPE: PRT
<213> ORGANISM: Mus musculus

<400> SEQUENCE: 4
```

```
Met Asp Asp Arg Glu Asp Leu Val Tyr Gln Ala Lys Leu Ala Glu Gln
1               5                   10                  15

Ala Glu Arg Tyr Asp Glu Met Val Glu Ser Met Lys Lys Val Ala Gly
            20                  25                  30

Met Asp Val Glu Leu Thr Val Glu Arg Asn Leu Leu Ser Val Ala
        35                  40                  45

Tyr Lys Asn Val Ile Gly Ala Arg Arg Ala Ser Trp Arg Ile Ile Ser
50                  55                  60

Ser Ile Glu Gln Lys Glu Glu Asn Lys Gly Gly Glu Asp Lys Leu Lys
65                  70                  75                  80

Met Ile Arg Glu Tyr Arg Gln Met Val Glu Thr Glu Leu Lys Leu Ile
                85                  90                  95

Cys Cys Asp Ile Leu Asp Val Gln Asp Lys His Leu Ile Pro Ala Ala
                100                 105                 110

Asn Thr Gly Glu Ser Lys Val Phe Tyr Tyr Lys Met Lys Gly Asp Tyr
                115                 120                 125

His Arg Tyr Leu Ala Glu Phe Ala Thr Gly Asn Asp Arg Lys Glu Ala
        130                 135                 140

Ala Glu Asn Ser Leu Val Ala Tyr Lys Ala Ala Ser Asp Ile Ala Met
145                 150                 155                 160

Thr Glu Leu Pro Pro Thr His Pro Ile Arg Leu Gly Leu Ala Leu Asn
                165                 170                 175

Phe Ser Val Phe Tyr Tyr Glu Ile Leu Asn Ser Pro Asp Arg Ala Cys
                180                 185                 190

Arg Leu Ala Lys Ala Ala Phe Asp Asp Ala Ile Ala Glu Leu Asp Thr
                195                 200                 205

Leu Ser Glu Glu Ser Tyr Lys Asp Ser Thr Leu Ile Met Gln Leu Leu
        210                 215                 220

Arg Asp Asn Leu Thr Leu Trp Thr Ser Asp Met Gln Gly Asp Gly Glu
225                 230                 235                 240

Glu Gln Asn Lys Glu Ala Leu Gln Asp Val Glu Asp Glu Asn Gln
                245                 250                 255

<210> SEQ ID NO 5
<211> LENGTH: 246
<212> TYPE: PRT
<213> ORGANISM: Homo sapiens

<400> SEQUENCE: 5

Met Gly Asp Arg Glu Gln Leu Leu Gln Arg Ala Arg Leu Ala Glu Gln
1               5                   10                  15

Ala Glu Arg Tyr Asp Asp Met Ala Ser Ala Met Lys Ala Val Thr Glu
            20                  25                  30

Leu Asn Glu Pro Leu Ser Asn Glu Asp Arg Asn Leu Leu Ser Val Ala
        35                  40                  45

Tyr Lys Asn Val Val Gly Ala Arg Arg Ser Ser Trp Arg Val Ile Ser
50                  55                  60

Ser Ile Glu Gln Lys Thr Met Ala Asp Gly Asn Glu Lys Lys Leu Glu
65                  70                  75                  80

Lys Val Lys Ala Tyr Arg Glu Lys Ile Glu Lys Glu Leu Glu Thr Val
                85                  90                  95

Cys Asn Asp Val Leu Ser Leu Leu Asp Lys Phe Leu Ile Lys Asn Cys
                100                 105                 110

Asn Asp Phe Gln Tyr Glu Ser Lys Val Phe Tyr Leu Lys Met Lys Gly
                115                 120                 125
```

Asp Tyr Tyr Arg Tyr Leu Ala Glu Val Ala Ser Gly Glu Lys Lys Asn
            130                 135                 140

Ser Val Val Glu Ala Ser Glu Ala Ala Tyr Lys Glu Ala Phe Glu Ile
145                 150                 155                 160

Ser Lys Glu Gln Met Gln Pro Thr His Pro Ile Arg Leu Gly Leu Ala
                    165                 170                 175

Leu Asn Phe Ser Val Phe Tyr Tyr Glu Ile Gln Asn Ala Pro Glu Gln
                180                 185                 190

Ala Cys Leu Leu Ala Lys Gln Ala Phe Asp Asp Ala Ile Ala Glu Leu
            195                 200                 205

Asp Thr Leu Asn Glu Asp Ser Tyr Lys Asp Ser Thr Leu Ile Met Gln
        210                 215                 220

Leu Leu Arg Asp Asn Leu Thr Leu Trp Thr Ser Asp Gln Gln Asp Glu
225                 230                 235                 240

Glu Ala Gly Glu Gly Asn
                245

<210> SEQ ID NO 6
<211> LENGTH: 246
<212> TYPE: PRT
<213> ORGANISM: Mus musculus

<400> SEQUENCE: 6

Met Gly Asp Arg Glu Gln Leu Leu Gln Arg Ala Arg Leu Ala Glu Gln
1               5                   10                  15

Ala Glu Arg Tyr Asp Asp Met Ala Ser Ala Met Lys Ala Val Thr Glu
            20                  25                  30

Leu Asn Glu Pro Leu Ser Asn Glu Asp Arg Asn Leu Leu Ser Val Ala
        35                  40                  45

Tyr Lys Asn Val Val Gly Ala Arg Arg Ser Ser Trp Arg Val Ile Ser
    50                  55                  60

Ser Ile Glu Gln Lys Thr Met Ala Asp Gly Asn Glu Lys Lys Leu Glu
65                  70                  75                  80

Lys Val Lys Ala Tyr Arg Glu Lys Ile Glu Lys Glu Leu Glu Thr Val
                85                  90                  95

Cys Asn Asp Val Leu Ala Leu Leu Asp Lys Phe Leu Ile Lys Asn Cys
            100                 105                 110

Asn Asp Phe Gln Tyr Glu Ser Lys Val Phe Tyr Leu Lys Met Lys Gly
        115                 120                 125

Asp Tyr Tyr Arg Tyr Leu Ala Glu Val Ala Ser Gly Glu Lys Lys Asn
    130                 135                 140

Ser Val Val Glu Ala Ser Glu Ala Ala Tyr Lys Glu Ala Phe Glu Ile
145                 150                 155                 160

Ser Lys Glu His Met Gln Pro Thr His Pro Ile Arg Leu Gly Leu Ala
                165                 170                 175

Leu Asn Phe Ser Val Phe Tyr Tyr Glu Ile Gln Asn Ala Pro Glu Gln
            180                 185                 190

Ala Cys Leu Leu Ala Lys Gln Ala Phe Asp Asp Ala Ile Ala Glu Leu
        195                 200                 205

Asp Thr Leu Asn Glu Asp Ser Tyr Lys Asp Ser Thr Leu Ile Met Gln
    210                 215                 220

Leu Leu Arg Asp Asn Leu Thr Leu Trp Thr Ser Asp Gln Gln Asp Glu
225                 230                 235                 240

Glu Ala Gly Glu Gly Asn
                245

-continued

<210> SEQ ID NO 7
<211> LENGTH: 247
<212> TYPE: PRT
<213> ORGANISM: Homo sapiens

<400> SEQUENCE: 7

Met Val Asp Arg Glu Gln Leu Val Gln Lys Ala Arg Leu Ala Glu Gln
1               5                   10                  15

Ala Glu Arg Tyr Asp Asp Met Ala Ala Ala Met Lys Asn Val Thr Glu
                20                  25                  30

Leu Asn Glu Pro Leu Ser Asn Glu Glu Arg Asn Leu Leu Ser Val Ala
            35                  40                  45

Tyr Lys Asn Val Val Gly Ala Arg Arg Ser Ser Trp Arg Val Ile Ser
    50                  55                  60

Ser Ile Glu Gln Lys Thr Ser Ala Asp Gly Asn Glu Lys Lys Ile Glu
65                  70                  75                  80

Met Val Arg Ala Tyr Arg Glu Lys Ile Glu Lys Glu Leu Glu Ala Val
                85                  90                  95

Cys Gln Asp Val Leu Ser Leu Leu Asp Asn Tyr Leu Ile Lys Asn Cys
            100                 105                 110

Ser Glu Thr Gln Tyr Glu Ser Lys Val Phe Tyr Leu Lys Met Lys Gly
        115                 120                 125

Asp Tyr Tyr Arg Tyr Leu Ala Glu Val Ala Thr Gly Glu Lys Arg Ala
130                 135                 140

Thr Val Val Glu Ser Ser Glu Lys Ala Tyr Ser Glu Ala His Glu Ile
145                 150                 155                 160

Ser Lys Glu His Met Gln Pro Thr His Pro Ile Arg Leu Gly Leu Ala
                165                 170                 175

Leu Asn Tyr Ser Val Phe Tyr Tyr Glu Ile Gln Asn Ala Pro Glu Gln
            180                 185                 190

Ala Cys His Leu Ala Lys Thr Ala Phe Asp Asp Ala Ile Ala Glu Leu
        195                 200                 205

Asp Thr Leu Asn Glu Asp Ser Tyr Lys Asp Ser Thr Leu Ile Met Gln
210                 215                 220

Leu Leu Arg Asp Asn Leu Thr Leu Trp Thr Ser Asp Gln Gln Asp Asp
225                 230                 235                 240

Asp Gly Gly Glu Gly Asn Asn
                245

<210> SEQ ID NO 8
<211> LENGTH: 247
<212> TYPE: PRT
<213> ORGANISM: Mus musculus

<400> SEQUENCE: 8

Met Val Asp Arg Glu Gln Leu Val Gln Lys Ala Arg Leu Ala Glu Gln
1               5                   10                  15

Ala Glu Arg Tyr Asp Asp Met Ala Ala Ala Met Lys Asn Val Thr Glu
                20                  25                  30

Leu Asn Glu Pro Leu Ser Asn Glu Glu Arg Asn Leu Leu Ser Val Ala
            35                  40                  45

Tyr Lys Asn Val Val Gly Ala Arg Arg Ser Ser Trp Arg Val Ile Ser
    50                  55                  60

Ser Ile Glu Gln Lys Thr Ser Ala Asp Gly Asn Glu Lys Lys Ile Glu
65                  70                  75                  80

```
Met Val Arg Ala Tyr Arg Glu Lys Ile Glu Lys Leu Glu Ala Val
                85                  90                  95

Cys Gln Asp Val Leu Ser Leu Leu Asp Asn Tyr Leu Ile Lys Asn Cys
               100                 105                 110

Ser Glu Thr Gln Tyr Glu Ser Lys Val Phe Tyr Leu Lys Met Lys Gly
           115                 120                 125

Asp Tyr Tyr Arg Tyr Leu Ala Glu Val Ala Thr Gly Glu Lys Arg Ala
       130                 135                 140

Thr Val Val Glu Ser Ser Glu Lys Ala Tyr Ser Glu Ala His Glu Ile
145                 150                 155                 160

Ser Lys Glu His Met Gln Pro Thr His Pro Ile Arg Leu Gly Leu Ala
                165                 170                 175

Leu Asn Tyr Ser Val Phe Tyr Tyr Glu Ile Gln Asn Ala Pro Glu Gln
               180                 185                 190

Ala Cys His Leu Ala Lys Thr Ala Phe Asp Asp Ala Ile Ala Glu Leu
           195                 200                 205

Asp Thr Leu Asn Glu Asp Ser Tyr Lys Asp Ser Thr Leu Ile Met Gln
       210                 215                 220

Leu Leu Arg Asp Asn Leu Thr Leu Trp Thr Ser Asp Gln Gln Asp Asp
225                 230                 235                 240

Asp Gly Gly Glu Gly Asn Asn
                245

<210> SEQ ID NO 9
<211> LENGTH: 245
<212> TYPE: PRT
<213> ORGANISM: Homo sapien

<400> SEQUENCE: 9

Met Glu Lys Thr Glu Leu Ile Gln Lys Ala Lys Leu Ala Glu Gln Ala
1               5                   10                  15

Glu Arg Tyr Asp Asp Met Ala Thr Cys Met Lys Ala Val Thr Glu Gln
                20                  25                  30

Gly Ala Glu Leu Ser Asn Glu Glu Arg Asn Leu Leu Ser Val Ala Tyr
            35                  40                  45

Lys Asn Val Val Gly Gly Arg Arg Ser Ala Trp Arg Val Ile Ser Ser
50                  55                  60

Ile Glu Gln Lys Thr Asp Thr Ser Asp Lys Lys Leu Gln Leu Ile Lys
65                  70                  75                  80

Asp Tyr Arg Glu Lys Val Glu Ser Glu Leu Arg Ser Ile Cys Thr Thr
                85                  90                  95

Val Leu Glu Leu Leu Asp Lys Tyr Leu Ile Ala Asn Ala Thr Asn Pro
            100                 105                 110

Glu Ser Lys Val Phe Tyr Leu Lys Met Lys Gly Asp Tyr Phe Arg Tyr
        115                 120                 125

Leu Ala Glu Val Ala Cys Gly Asp Asp Arg Lys Gln Thr Ile Asp Asn
    130                 135                 140

Ser Gln Gly Ala Tyr Gln Glu Ala Phe Asp Ile Ser Lys Lys Glu Met
145                 150                 155                 160

Gln Pro Thr His Pro Ile Arg Leu Gly Leu Ala Leu Asn Phe Ser Val
                165                 170                 175

Phe Tyr Tyr Glu Ile Leu Asn Asn Pro Glu Leu Ala Cys Thr Leu Ala
            180                 185                 190

Lys Thr Ala Phe Asp Glu Ala Ile Ala Glu Leu Asp Thr Leu Asn Glu
        195                 200                 205
```

```
Asp Ser Tyr Lys Asp Ser Thr Leu Ile Met Gln Leu Leu Arg Asp Asn
        210                 215                 220

Leu Thr Leu Trp Thr Ser Asp Ser Ala Gly Glu Glu Cys Asp Ala Ala
225                 230                 235                 240

Glu Gly Ala Glu Asn
            245

<210> SEQ ID NO 10
<211> LENGTH: 245
<212> TYPE: PRT
<213> ORGANISM: Mus musculus

<400> SEQUENCE: 10

Met Glu Lys Thr Glu Leu Ile Gln Lys Ala Lys Leu Ala Glu Gln Ala
1               5                   10                  15

Glu Arg Tyr Asp Asp Met Ala Thr Cys Met Lys Ala Val Thr Glu Gln
            20                  25                  30

Gly Ala Glu Leu Ser Asn Glu Glu Arg Asn Leu Leu Ser Val Ala Tyr
        35                  40                  45

Lys Asn Val Val Gly Arg Arg Ser Ala Trp Arg Val Ile Ser Ser
50                  55                  60

Ile Glu Gln Lys Thr Asp Thr Ser Asp Lys Lys Leu Gln Leu Ile Lys
65                  70                  75                  80

Asp Tyr Arg Glu Lys Val Glu Ser Glu Leu Arg Ser Ile Cys Thr Thr
                85                  90                  95

Val Leu Glu Leu Leu Asp Lys Tyr Leu Ile Ala Asn Ala Thr Asn Pro
            100                 105                 110

Glu Ser Lys Val Phe Tyr Leu Lys Met Lys Gly Asp Tyr Phe Arg Tyr
        115                 120                 125

Leu Ala Glu Val Ala Cys Gly Asp Asp Arg Lys Gln Thr Ile Glu Asn
130                 135                 140

Ser Gln Gly Ala Tyr Gln Glu Ala Phe Asp Ile Ser Lys Lys Glu Met
145                 150                 155                 160

Gln Pro Thr His Pro Ile Arg Leu Gly Leu Ala Leu Asn Phe Ser Val
                165                 170                 175

Phe Tyr Tyr Glu Ile Leu Asn Asn Pro Glu Leu Ala Cys Thr Leu Ala
            180                 185                 190

Lys Thr Ala Phe Asp Glu Ala Ile Ala Glu Leu Asp Thr Leu Asn Glu
        195                 200                 205

Asp Ser Tyr Lys Asp Ser Thr Leu Ile Met Gln Leu Leu Arg Asp Asn
210                 215                 220

Leu Thr Leu Trp Thr Ser Asp Ser Ala Gly Glu Glu Cys Asp Ala Ala
225                 230                 235                 240

Glu Gly Ala Glu Asn
            245

<210> SEQ ID NO 11
<211> LENGTH: 245
<212> TYPE: PRT
<213> ORGANISM: Homo sapiens

<400> SEQUENCE: 11

Met Asp Lys Asn Glu Leu Val Gln Lys Ala Lys Leu Ala Glu Gln Ala
1               5                   10                  15

Glu Arg Tyr Asp Asp Met Ala Ala Cys Met Lys Ser Val Thr Glu Gln
            20                  25                  30

Gly Ala Glu Leu Ser Asn Glu Glu Arg Asn Leu Leu Ser Val Ala Tyr
```

```
                35                  40                  45
Lys Asn Val Val Gly Ala Arg Arg Ser Ser Trp Arg Val Val Ser Ser
 50                  55                  60
Ile Glu Gln Lys Thr Glu Gly Ala Glu Lys Lys Gln Gln Met Ala Arg
 65                  70                  75                  80
Glu Tyr Arg Glu Lys Ile Glu Thr Glu Leu Arg Asp Ile Cys Asn Asp
                 85                  90                  95
Val Leu Ser Leu Leu Glu Lys Phe Leu Ile Pro Asn Ala Ser Gln Ala
             100                 105                 110
Glu Ser Lys Val Phe Tyr Leu Lys Met Lys Gly Asp Tyr Tyr Arg Tyr
             115                 120                 125
Leu Ala Glu Val Ala Ala Gly Asp Asp Lys Lys Gly Ile Val Asp Gln
             130                 135                 140
Ser Gln Gln Ala Tyr Gln Glu Ala Phe Glu Ile Ser Lys Lys Glu Met
145                 150                 155                 160
Gln Pro Thr His Pro Ile Arg Leu Gly Leu Ala Leu Asn Phe Ser Val
                165                 170                 175
Phe Tyr Tyr Glu Ile Leu Asn Ser Pro Glu Lys Ala Cys Ser Leu Ala
                180                 185                 190
Lys Thr Ala Phe Asp Glu Ala Ile Ala Glu Leu Asp Thr Leu Ser Glu
            195                 200                 205
Glu Ser Tyr Lys Asp Ser Thr Leu Ile Met Gln Leu Leu Arg Asp Asn
            210                 215                 220
Leu Thr Leu Trp Thr Ser Asp Thr Gln Gly Asp Glu Ala Glu Ala Gly
225                 230                 235                 240
Glu Gly Gly Glu Asn
                245

<210> SEQ ID NO 12
<211> LENGTH: 245
<212> TYPE: PRT
<213> ORGANISM: Mus musculus

<400> SEQUENCE: 12

Met Asp Lys Asn Glu Leu Val Gln Lys Ala Lys Leu Ala Glu Gln Ala
 1               5                  10                  15
Glu Arg Tyr Asp Asp Met Ala Ala Cys Met Lys Ser Val Thr Glu Gln
             20                  25                  30
Gly Ala Glu Leu Ser Asn Glu Glu Arg Asn Leu Leu Ser Val Ala Tyr
             35                  40                  45
Lys Asn Val Val Gly Ala Arg Arg Ser Ser Trp Arg Val Val Ser Ser
 50                  55                  60
Ile Glu Gln Lys Thr Glu Gly Ala Glu Lys Lys Gln Gln Met Ala Arg
 65                  70                  75                  80
Glu Tyr Arg Glu Lys Ile Glu Thr Glu Leu Arg Asp Ile Cys Asn Asp
                 85                  90                  95
Val Leu Ser Leu Leu Glu Lys Phe Leu Ile Pro Asn Ala Ser Gln Pro
             100                 105                 110
Glu Ser Lys Val Phe Tyr Leu Lys Met Lys Gly Asp Tyr Tyr Arg Tyr
             115                 120                 125
Leu Ala Glu Val Ala Ala Gly Asp Asp Lys Lys Gly Ile Val Asp Gln
             130                 135                 140
Ser Gln Gln Ala Tyr Gln Glu Ala Phe Glu Ile Ser Lys Lys Glu Met
145                 150                 155                 160
Gln Pro Thr His Pro Ile Arg Leu Gly Leu Ala Leu Asn Phe Ser Val
```

```
                165                 170                 175
Phe Tyr Tyr Glu Ile Leu Asn Ser Pro Glu Lys Ala Cys Ser Leu Ala
            180                 185                 190

Lys Thr Ala Phe Asp Glu Ala Ile Ala Glu Leu Asp Thr Leu Ser Glu
                195                 200                 205

Glu Ser Tyr Lys Asp Ser Thr Leu Ile Met Gln Leu Leu Arg Asp Asn
210                 215                 220

Leu Thr Leu Trp Thr Ser Asp Thr Gln Gly Asp Glu Ala Glu Ala Gly
225                 230                 235                 240

Glu Gly Gly Glu Asn
            245

<210> SEQ ID NO 13
<211> LENGTH: 248
<212> TYPE: PRT
<213> ORGANISM: Homo sapiens

<400> SEQUENCE: 13

Met Glu Arg Ala Ser Leu Ile Gln Lys Ala Lys Leu Ala Glu Gln Ala
1               5                   10                  15

Glu Arg Tyr Glu Asp Met Ala Ala Phe Met Lys Gly Ala Val Glu Lys
            20                  25                  30

Gly Glu Glu Leu Ser Cys Glu Glu Arg Asn Leu Leu Ser Val Ala Tyr
        35                  40                  45

Lys Asn Val Val Gly Gly Gln Arg Ala Ala Trp Arg Val Leu Ser Ser
    50                  55                  60

Ile Glu Gln Lys Ser Asn Glu Glu Gly Ser Glu Glu Lys Gly Pro Glu
65                  70                  75                  80

Val Arg Glu Tyr Arg Glu Lys Val Glu Thr Glu Leu Gln Gly Val Cys
                85                  90                  95

Asp Thr Val Leu Gly Leu Leu Asp Ser His Leu Ile Lys Glu Ala Gly
            100                 105                 110

Asp Ala Glu Ser Arg Val Phe Tyr Leu Lys Met Lys Gly Asp Tyr Tyr
        115                 120                 125

Arg Tyr Leu Ala Glu Val Ala Thr Gly Asp Asp Lys Lys Arg Ile Ile
    130                 135                 140

Asp Ser Ala Arg Ser Ala Tyr Gln Glu Ala Met Asp Ile Ser Lys Lys
145                 150                 155                 160

Glu Met Pro Pro Thr Asn Pro Ile Arg Leu Gly Leu Ala Leu Asn Phe
                165                 170                 175

Ser Val Phe His Tyr Glu Ile Ala Asn Ser Pro Glu Glu Ala Ile Ser
            180                 185                 190

Leu Ala Lys Thr Thr Phe Asp Glu Ala Met Ala Asp Leu His Thr Leu
        195                 200                 205

Ser Glu Asp Ser Tyr Lys Asp Ser Thr Leu Ile Met Gln Leu Leu Arg
    210                 215                 220

Asp Asn Leu Thr Leu Trp Thr Ala Asp Asn Ala Gly Glu Glu Gly Gly
225                 230                 235                 240

Glu Ala Pro Gln Glu Pro Gln Ser
                245

<210> SEQ ID NO 14
<211> LENGTH: 248
<212> TYPE: PRT
<213> ORGANISM: Mus musculus

<400> SEQUENCE: 14
```

Met Glu Arg Ala Ser Leu Ile Gln Lys Ala Lys Leu Ala Glu Gln Ala
1               5                   10                  15

Glu Arg Tyr Glu Asp Met Ala Ala Phe Met Lys Ser Ala Val Glu Lys
            20                  25                  30

Gly Glu Glu Leu Ser Cys Glu Glu Arg Asn Leu Leu Ser Val Ala Tyr
                35                  40                  45

Lys Asn Val Val Gly Gly Gln Arg Ala Ala Trp Arg Val Leu Ser Ser
50                  55                  60

Ile Glu Gln Lys Ser Asn Glu Glu Gly Ser Glu Glu Lys Gly Pro Glu
65                  70                  75                  80

Val Lys Glu Tyr Arg Glu Lys Val Glu Thr Glu Leu Arg Gly Val Cys
                85                  90                  95

Asp Thr Val Leu Gly Leu Leu Asp Ser His Leu Ile Lys Gly Ala Gly
            100                 105                 110

Asp Ala Glu Ser Arg Val Phe Tyr Leu Lys Met Lys Gly Asp Tyr Tyr
        115                 120                 125

Arg Tyr Leu Ala Glu Val Ala Thr Gly Asp Asp Lys Lys Arg Ile Ile
    130                 135                 140

Asp Ser Ala Arg Ser Ala Tyr Gln Glu Ala Met Asp Ile Ser Lys Lys
145                 150                 155                 160

Glu Met Pro Pro Thr Asn Pro Ile Arg Leu Gly Leu Ala Leu Asn Phe
                165                 170                 175

Ser Val Phe His Tyr Glu Ile Ala Asn Ser Pro Glu Glu Ala Ile Ser
            180                 185                 190

Leu Ala Lys Thr Thr Phe Asp Glu Ala Met Ala Asp Leu His Thr Leu
        195                 200                 205

Ser Glu Asp Ser Tyr Lys Asp Ser Thr Leu Ile Met Gln Leu Leu Arg
    210                 215                 220

Asp Asn Leu Thr Leu Trp Thr Ala Asp Ser Ala Gly Glu Glu Gly Gly
225                 230                 235                 240

Glu Ala Pro Glu Glu Pro Gln Ser
                245

<210> SEQ ID NO 15
<211> LENGTH: 15
<212> TYPE: PRT
<213> ORGANISM: Homo sapiens

<400> SEQUENCE: 15

Arg Leu Gly Arg Asp Lys Tyr Lys Thr Leu Arg Gln Ile Arg Gln
1               5                   10                  15

<210> SEQ ID NO 16
<211> LENGTH: 21
<212> TYPE: PRT
<213> ORGANISM: Homo sapiens

<400> SEQUENCE: 16

Arg Leu Gly Arg Asp Lys Tyr Lys Thr Leu Arg Gln Ile Arg Gln Gly
1               5                   10                  15

Asn Thr Lys Gln Arg
            20

<210> SEQ ID NO 17
<211> LENGTH: 21
<212> TYPE: PRT
<213> ORGANISM: Homo sapiens

```
<400> SEQUENCE: 17

Arg Leu Gly Trp Trp Arg Phe Tyr Thr Leu Arg Arg Ala Arg Gln Gly
1               5                   10                  15

Asn Thr Lys Gln Arg
            20

<210> SEQ ID NO 18
<211> LENGTH: 14
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION

<400> SEQUENCE: 18

Val Lys Lys Lys Ser Asn Ser Ile Ser Val Gly Glu Phe Tyr
1               5                   10

<210> SEQ ID NO 19
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION

<400> SEQUENCE: 19

Asn Leu Gln Arg His Ser Asn Ser Leu Gly Pro Ile Phe Asp His
1               5                   10                  15

<210> SEQ ID NO 20
<211> LENGTH: 22
<212> TYPE: PRT
<213> ORGANISM: Mus musculus
<220> FEATURE:
<221> NAME/KEY: MOD_RES
<222> LOCATION: (11)..(11)
<223> OTHER INFORMATION: PHOSPHORYLATION

<400> SEQUENCE: 20

Asn Thr Leu Gln Glu Gly Val Ala Ser Gly Ser Asp Gly Asn Phe Ser
1               5                   10                  15

Glu Asp Ala Leu Ala Lys
            20

<210> SEQ ID NO 21
<211> LENGTH: 11
<212> TYPE: PRT
<213> ORGANISM: Mus musculus
<220> FEATURE:
<221> NAME/KEY: MOD_RES
<222> LOCATION: (3)..(3)
<223> OTHER INFORMATION: PHOSPHORYLATION

<400> SEQUENCE: 21

Ser Asn Ser Ile Ser Val Gly Glu Val Tyr Arg
1               5                   10

<210> SEQ ID NO 22
<211> LENGTH: 12
<212> TYPE: PRT
<213> ORGANISM: Mus musculus
<220> FEATURE:
<221> NAME/KEY: MOD_RES
<222> LOCATION: (4)..(4)
<223> OTHER INFORMATION: PHOSPHORYLATION
```

<400> SEQUENCE: 22

Lys Ser Asn Ser Ile Ser Val Gly Glu Val Tyr Arg
 1               5                  10

<210> SEQ ID NO 23
<211> LENGTH: 16
<212> TYPE: PRT
<213> ORGANISM: Mus musculus
<220> FEATURE:
<221> NAME/KEY: MOD_RES
<222> LOCATION: (4)..(4)
<223> OTHER INFORMATION: PHOSPHORYLATION

<400> SEQUENCE: 23

His Ser Asn Ser Leu Gly Pro Val Phe Asp His Glu Asp Leu Leu Arg
 1               5                  10                  15

<210> SEQ ID NO 24
<211> LENGTH: 22
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: PHOSPHORYLATION

<400> SEQUENCE: 24

Ser Ala Val Glu Glu Gly Thr Ala Ser Gly Ser Asp Gly Asn Phe Ser
 1               5                  10                  15

Glu Asp Val Leu Ser Lys
            20

<210> SEQ ID NO 25
<211> LENGTH: 11
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION

<400> SEQUENCE: 25

Ser Asn Ser Ile Ser Val Gly Glu Phe Tyr Arg
 1               5                  10

<210> SEQ ID NO 26
<211> LENGTH: 12
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION

<400> SEQUENCE: 26

Lys Ser Asn Ser Ile Ser Val Gly Glu Phe Tyr Arg
 1               5                  10

<210> SEQ ID NO 27
<211> LENGTH: 17
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION

<400> SEQUENCE: 27

His Ser Asn Ser Leu Gly Pro Ile Phe Asp His Glu Asp Leu Leu Lys
1               5                   10                  15

Arg

<210> SEQ ID NO 28
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION

<400> SEQUENCE: 28

Ile Leu Ser Ser Asp Asp Ser Leu Arg
1               5

<210> SEQ ID NO 29
<211> LENGTH: 12
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION

<400> SEQUENCE: 29

His Ser Asp Ser Ile Ser Ser Leu Ala Ser Glu Arg
1               5                   10

<210> SEQ ID NO 30
<211> LENGTH: 12
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION
<220> FEATURE:
<221> NAME/KEY: MOD_RES
<222> LOCATION: (7)..(7)
<223> OTHER INFORMATION: PHOSPHORYLATION

<400> SEQUENCE: 30

His Ser Asp Ser Ile Ser Ser Leu Ala Ser Glu Arg
1               5                   10

<210> SEQ ID NO 31
<211> LENGTH: 37
<212> TYPE: PRT
<213> ORGANISM: Homo sapiens

<400> SEQUENCE: 31

Lys Lys Lys Ser Asn Ser Ile Ser Val Gly Glu Phe Tyr Arg Asp Ala
1               5                   10                  15

Val Leu Gln Arg Cys Ser Pro Asn Leu Gln Arg His Ser Asn Ser Leu
            20                  25                  30

Gly Pro Ile Phe Asp
        35

<210> SEQ ID NO 32
<211> LENGTH: 37
<212> TYPE: PRT
<213> ORGANISM: Mus musculus

<400> SEQUENCE: 32

```
Lys Arg Lys Ser Asn Ser Ile Ser Val Gly Glu Val Tyr Arg Asp Leu
1               5                   10                  15

Ala Leu Gln Arg Tyr Ser Pro Asn Ala Gln Arg His Ser Asn Ser Leu
            20                  25                  30

Gly Pro Val Phe Asp
            35

<210> SEQ ID NO 33
<211> LENGTH: 37
<212> TYPE: PRT
<213> ORGANISM: Rattus norvegicus

<400> SEQUENCE: 33

Lys Lys Lys Ser Asn Ser Val Ser Val Gly Glu Val Tyr Arg Asp Leu
1               5                   10                  15

Ala Leu Gln Arg Cys Ser Pro Asn Ala Gln Arg His Ser Ser Ser Leu
            20                  25                  30

Gly Pro Val Phe Asp
            35

<210> SEQ ID NO 34
<211> LENGTH: 37
<212> TYPE: PRT
<213> ORGANISM: Bos taurus

<400> SEQUENCE: 34

Lys Thr Lys Ser Asn Ser Ile Ser Val Gly Glu Phe Tyr Gln Asp Pro
1               5                   10                  15

Ala Leu Gln Arg Cys Ser Pro Asn Leu Gln Arg His Ser Ser Ser Leu
            20                  25                  30

Gly Pro Ile Phe Asp
            35

<210> SEQ ID NO 35
<211> LENGTH: 37
<212> TYPE: PRT
<213> ORGANISM: Canis familiaris

<400> SEQUENCE: 35

Lys Arg Lys Ser Asn Ser Ile Ser Val Gly Glu Phe Tyr His Asp Arg
1               5                   10                  15

Ala Leu Gln Arg Cys Ser Pro Asn Leu Gln Arg His Ser Asn Ser Leu
            20                  25                  30

Gly Pro Ile Phe Asp
            35

<210> SEQ ID NO 36
<211> LENGTH: 38
<212> TYPE: PRT
<213> ORGANISM: Gallus gallus

<400> SEQUENCE: 36

Lys Lys Lys Ser Asn Ser Ile Ala Val Ala Asp Leu His Cys Arg Glu
1               5                   10                  15

Leu Ala Phe Gln Arg Gly Ser Pro Thr Leu Pro Arg His Ser Tyr Ser
            20                  25                  30

Val Gly Pro Gly Ser Asp
            35

<210> SEQ ID NO 37
<211> LENGTH: 13
```

```
<212> TYPE: PRT
<213> ORGANISM: Homo sapiens

<400> SEQUENCE: 37

Val Lys Lys Lys Ser Asn Ser Ile Ser Val Gly Glu Phe
1               5                   10

<210> SEQ ID NO 38
<211> LENGTH: 13
<212> TYPE: PRT
<213> ORGANISM: Homo sapiens

<400> SEQUENCE: 38

Leu Gln Arg His Ser Asn Ser Leu Gly Pro Ile Phe Asp
1               5                   10

<210> SEQ ID NO 39
<211> LENGTH: 52
<212> TYPE: PRT
<213> ORGANISM: Homo sapiens

<400> SEQUENCE: 39

Asp Ser Glu Gly Ser Glu Gly Ser Phe Leu Val Lys Lys Lys Ser Asn
1               5                   10                  15

Ser Ile Ser Val Gly Glu Phe Tyr Arg Asp Ala Val Leu Gln Arg Cys
            20                  25                  30

Ser Pro Asn Leu Gln Arg His Ser Asn Ser Leu Gly Pro Ile Phe Asp
        35                  40                  45

His Glu Asp Leu
    50

<210> SEQ ID NO 40
<211> LENGTH: 52
<212> TYPE: PRT
<213> ORGANISM: Pan troglodytes

<400> SEQUENCE: 40

Asp Ser Glu Gly Ser Glu Gly Ser Phe Leu Val Lys Arg Lys Ser Asn
1               5                   10                  15

Ser Ile Ser Val Gly Glu Phe Tyr Arg Asp Ala Val Leu Gln Arg Cys
            20                  25                  30

Ser Pro Asn Leu Gln Arg His Ser Asn Ser Leu Gly Pro Ile Phe Asp
        35                  40                  45

His Glu Asp Leu
    50

<210> SEQ ID NO 41
<211> LENGTH: 52
<212> TYPE: PRT
<213> ORGANISM: Mus musculus

<400> SEQUENCE: 41

Asp Ser Glu Gly Ser Glu Ser Ser Phe Leu Val Lys Arg Lys Ser Asn
1               5                   10                  15

Ser Ile Ser Val Gly Glu Val Tyr Arg Asp Leu Ala Leu Gln Arg Tyr
            20                  25                  30

Ser Pro Asn Ala Gln Arg His Ser Asn Ser Leu Gly Pro Val Phe Asp
        35                  40                  45

His Glu Asp Leu
    50
```

```
<210> SEQ ID NO 42
<211> LENGTH: 52
<212> TYPE: PRT
<213> ORGANISM: Rattus norvegicus

<400> SEQUENCE: 42

Asp Ser Glu Gly Ser Glu Ser Ser Phe Leu Val Lys Lys Lys Ser Asn
1               5                   10                  15

Ser Val Ser Val Gly Glu Val Tyr Arg Asp Leu Ala Leu Gln Arg Cys
            20                  25                  30

Ser Pro Asn Ala Gln Arg His Ser Ser Leu Gly Pro Val Phe Asp
        35                  40                  45

His Glu Asp Leu
    50

<210> SEQ ID NO 43
<211> LENGTH: 52
<212> TYPE: PRT
<213> ORGANISM: Bos taurus

<400> SEQUENCE: 43

Asp Ser Glu Gly Ser Glu Gly Ser Phe Leu Val Lys Thr Lys Ser Asn
1               5                   10                  15

Ser Ile Ser Val Gly Glu Phe Tyr Gln Asp Pro Ala Leu Gln Arg Cys
            20                  25                  30

Ser Pro Asn Leu Gln Arg His Ser Ser Leu Gly Pro Ile Phe Asp
        35                  40                  45

His Glu Asp Leu
    50

<210> SEQ ID NO 44
<211> LENGTH: 52
<212> TYPE: PRT
<213> ORGANISM: Canis familiaris

<400> SEQUENCE: 44

Asp Ser Glu Gly Ser Glu Gly Ser Phe Leu Val Lys Arg Lys Ser Asn
1               5                   10                  15

Ser Ile Ser Val Gly Glu Phe Tyr His Asp Arg Ala Leu Gln Arg Cys
            20                  25                  30

Ser Pro Asn Leu Gln Arg His Ser Asn Ser Leu Gly Pro Ile Phe Asp
        35                  40                  45

His Glu Asp Phe
    50

<210> SEQ ID NO 45
<211> LENGTH: 53
<212> TYPE: PRT
<213> ORGANISM: Gallus gallus

<400> SEQUENCE: 45

Asp Ser Glu Gly Ser Glu Gly Ser Val Phe Arg Lys Lys Lys Ser Asn
1               5                   10                  15

Ser Ile Ala Val Ala Asp Leu His Cys Arg Glu Leu Ala Phe Gln Arg
            20                  25                  30

Gly Ser Pro Thr Leu Pro Arg His Ser Tyr Ser Val Gly Pro Gly Ser
        35                  40                  45

Asp Tyr Glu Pro Leu
    50
```

METHODS FOR IDENTIFYING MODULATORS OF LRRK2

The present invention relates to an assay for assessing LRRK2 inhibitors.

Autosomal dominant missense mutations within the gene encoding for the Leucine Rich Repeat protein Kinase-2 (LRRK2) predispose humans to Parkinson's disease [1, 2]. Patients with LRRK2 mutations generally develop Parkinson's disease with clinical appearance and symptoms indistinguishable from idiopathic Parkinson's disease at around 60-70 years of age [3]. Mutations in LRRK2 account for 4% of familial Parkinson's disease, and are observed in 1% of sporadic Parkinson's disease patients [3].

LRRK2 is a large enzyme (2527 residues), consisting of leucine rich repeats (residues 1010-1287), GTPase domain (residues 1335-1504), COR domain (residues 1517-1843), serine/threonine protein kinase domain (residues 1875-2132) and a WD40 repeat (residues 2231-2276) [4]. Over 40 missense mutations have been reported [5]. The activity as well as localisation of a subset of mutant forms of LRRK2 has been analysed in previous work using various forms of recombinant LRRK2 expressed and assayed using diverse approaches [4, 32]. The most frequent mutation comprises an amino acid substitution of the highly conserved Gly2019 located within the subdomain VII-DFG motif of the kinase domain to a Ser residue [5], which enhances the protein kinase activity of LRRK2 around two-fold [6]. This finding suggests that inhibitors of LRRK2 may have utility for the treatment of Parkinson's disease. It was also reported that various mutants such as LRRK2[R1441C] and LRRK2[Y1699C] accumulated within discrete cytosolic pools that were suggested to consist of aggregates of misfolded protein [6].

The intrinsic protein kinase catalytic activity of LRRK2 is readily measured in vitro in assays employing peptide substrates such as LRRKtide [7] or Nictide [8]; see also WO 2008/122789 and PCT/GB2009/002047. This has made it possible to undertake screens to identify inhibitors. Recent work has shown that a widely deployed Rho-kinase (ROCK) inhibitor termed H-1152 also inhibited LRRK2 with similar potency ($IC_{50}$ of 150 nM) [8]. The multi-target tyrosine kinase inhibitor sunitinib (marketed as Sutent and also known as SU11248), used for the treatment of renal cell carcinoma and other cancers, has recently been demonstrated to inhibit LRRK2 ($IC_{50}$ of 20 nM) [8-10]. We have also found that H-1152 and sunitinib inhibit the LRRK2[G2019S] mutant two to four-fold more potently than wild type LRRK2 [8]. Based on molecular modelling of the LRRK2 kinase domain we have designed a drug resistant LRRK2[Ala2016Thr] mutant that was normally active, but 32-fold less sensitive to H-1152 and 12-fold less sensitive to sunitinib [8].

A bottleneck in the development of LRRK2 inhibitors is how to assess the relative effectiveness of these compounds in vivo, as little is known about how LRRK2 is regulated and what its substrates are. We provide methods that can be used to assess LRRK2 inhibitors in a cell-based system. We demonstrate that LRRK2 kinase activity regulates phosphorylation of two N-terminal residues adjacent to the leucine rich repeat domain (Ser910 and Ser935), which mediate binding to the phospho-adapter 14-3-3 proteins [11]. Consistent with this, H-1152 and sunitinib induced dephosphorylation of Ser910 and Ser935 thereby disrupting 14-3-3-interaction with wild type LRRK2 and LRRK2[G2019S], but not with the drug resistant LRRK2[Ala2016Thr] mutant. We provide evidence that disruption of 14-3-3-binding induces LRRK2 to accumulate within cytoplasmic pools, similar in appearance to those reported previously for the LRRK2[R1441C] and LRRK2[Y1699C] mutants. Phosphorylation of Ser910 and Ser935 or 14-3-3 binding, or subcellular location of LRRK2, can be used to monitor the efficacy of LRRK2 inhibitors.

A first aspect of the invention provides a method for assessing the effect of a test compound on LRRK2 in a cell-based system, the method comprising the steps of
a) assessing the effect of exposing the cell-based system comprising LRRK2 to the test compound on the phosphorylation state of Ser910 and/or Ser935 of the LRRK2; and/or
b) assessing the effect of exposing the cell-based system comprising LRRK2 to the test compound on the binding of the LRRK2 to a 14-3-3 polypeptide.

In some embodiments, the method may comprise, or further comprise the step of assessing the effect of exposing the cell-based system comprising LRRK2 to the test compound on the subcellular location of LRRK2.

The method may yet further comprise the step of selecting a compound as being considered to have an inhibitory effect on LRRK2 in a cell-based system, wherein a test compound is so selected if the phosphorylation of Ser910 and/or Ser935 of the LRRK2 is reduced following the exposure; and/or the binding of the LRRK2 to a 14-3-3 polypeptide is reduced following the exposure.

The test compound may typically be a compound that has already been selected as a possible inhibitor of LRRK2, for example using an in vitro assay, for example an assay using LRRKtide or Nictide as an LRRK2 substrate polypeptide. Examples of assays suitable for selecting a compound as a possible inhibitor of LRRK2 are described in, for example, WO 2008/122789 and PCT/GB2009/002047.

Typically phosphorylation of Ser910 is assessed using an antibody that binds specifically to LRRK2 phosphorylated at Ser910 or an antibody that binds specifically to LRRK2 that is not phosphorylated at Ser910.

Typically phosphorylation of Ser935 is assessed using an antibody that binds specifically to LRRK2 phosphorylated at Ser935 or an antibody that binds specifically to LRRK2 that is not phosphorylated at Ser935.

By an antibody that binds specifically to LRRK2 phosphorylated at Ser910 is meant an antibody that binds to LRRK2 phosphorylated at Ser910, but not to LRRK2 that is not phosphorylated at Ser910, or to other phosphorylated serine residues. Similarly an antibody that binds specifically to LRRK2 phosphorylated at Ser935 does not bind to LRRK2 that is not phosphorylated at Ser935, or to other phosphorylated serine residues. An antibody that binds generally to phosphorylated serine residues is not an antibody that binds specifically to LRRK2 phosphorylated at Ser910 or an antibody that binds specifically to LRRK2 phosphorylated at Ser935.

Similar considerations apply in relation to an antibody that binds specifically to LRRK2 that is not phosphorylated at Ser910 or an antibody that binds specifically to LRRK2 that is not phosphorylated at Ser935. An antibody that binds specifically to LRRK2 that is not phosphorylated at Ser910 does not bind to LRRK2 that is phosphorylated at Ser910. An antibody that binds specifically to LRRK2 that is not phosphorylated at Ser935 does not bind to LRRK2 that is phosphorylated at Ser935.

Methods of generating and using such antibodies will be apparent to those skilled in the art. Examples of such antibodies and methods of generating and using them are described in the Examples. The antibodies may be polyclonal or monoclonal.

As an example an ELISA type assay may be particularly useful, as will be well known to those skilled in the art.

Binding of the LRRK2 to a 14-3-3 polypeptide may be assessed by any suitable technique for assessing protein:protein interaction. Typically a FRET (fluorescence resonance energy transfer) technique may be used, as discussed further below. Other techniques that may be useful may make use of immunoprecipitation techniques. For example, immunoprecipitation may be with an antibody that binds specifically to LRRK2; or may be with an antibody that binds specifically to a 14-3-3 polypeptide, as will be apparent to the skilled person. Antibodies that bind specifically to a 14-3-3 polypeptide will be well known to those skilled in the art and are commercially available. Alternatively, immunoprecipitation may be with an antibody that binds specifically to a tag present on recombinant LRRK2; or with an antibody that binds specifically to a tag present on recombinant 14-3-3 polypeptide, as will also be apparent to the skilled person.

As an example, it is considered that detection of phospho/dephospho-LRRK coupled with either 14-3-3 co-pull down or an anti-LRRK2 antibody (not phosphorylation state dependent) can be carried out using Invitrogen's Alpha-Elisa technologies, which would be useful in achieving a high throughput screening system. Multiplex assays using Luminex beads or plate based electrochemiluminescence (MSD; meso scale discovery) detection could also be used.

Details of Alpha screen technology (Perkin Elmer) applicable to both protein:protein and phosphoprotein detection (Sure fire kits developed and sold for MAPK, JAK/STAT and AKT pathways) can be found at, for example, http://las.perkinelmer.co.uk/Catalog/
   CategoryPage.htm?CategoryID=AlphaTech&M=BIO Details of Luminex technology applicable to phospho protein detection and protein:protein and total protein quantitation can be found at, for example,
http://www.luminexcorp.com/applications/cellular_signaling.html An example of the use of such technology is described in reference Khan I H, Zhao J., Ghosh, P. Ziman, M., Sweeney C, Kung H J and Luciw P A (2010) Assay Drug Dev technology 8, 27-36.

In MSD technology the principles of capture onto surface of plate and antibody detection are the same as any ELISA but the mode of detection uses electrochemiluminescence via Ruthenium tagged probes, and the technology allows multiplexing in the well through an array format.
http://www.mesoscale.com/CatalogSystemWeb/WebRoot/
   literature/brochures/pdf/techBrochure.pdf Quantitative Stable Isotope Labelling with Amino acids in Cell culture (SILAC)-based mass spectrometry may be used to identify and quantitate proteins associated with immunoprecipitates of LRRK2 (or of a 14-3-3 polypeptide). Other immunoprecipitate methods may be used, as will be well known to those skilled in the art. For example digoxygenin labeled 14-3-3 polypeptide may be used. Some examples of such methods are described in the Examples. As noted above, other techniques for assessing protein:protein interactions in cells or cell extracts may also be used. For example, a fluorescence resonance energy transfer (FRET) based system may be used if the interaction of a recombinant LRRK2 and recombinant 14-3-3 polypeptide is being assessed, for example if both LRRK2 and 14-3-3 polypeptide are both tagged with a fluorescent polypeptide.

Thus, the molecular interaction between LRRK2 and 14-3-3 proteins (and the effects of test compounds) could be investigated using a FRET-based method such as FLIM-FRET on a microscope such as a multiphoton microscope. As an example, a construct for expressing Cherry-tagged wild type 14-3-3 isoform or (as a control) an inactive mutant of Cherry-tagged 14-3-3 isoform such as 14-3-3 zeta [E180K] that does not bind phospho targets may be transfected into a cell line stably expressing wild type GFP-LRRK2 or (as controls) GFP-LRRK2[S910A/S935A]. FRET (fluorescence resonance energy transfer) can occur when the GFP and mCherry fluorophores are brought together by virtue of the binding of LRRK2 to 14-3-3 which will in turn affect their fluorescence lifetime, which can be detected. Using FLIM (fluorescence lifetime imaging microscopy) we can generate a spatial distribution of the cell where sites of strong protein-protein interaction (and therefore FRET) and weak interaction or no interaction can be recognised (by colour coding: see, for example, Lières et al. 2009 Quantitative analysis of chromatin compaction in living cells using FLIM-FRET. J. Cell Biol. 2009 Nov. 16; 187(4):481-96). No FLIM-FRET should be observed between GFP-LRRK2[S910A/S935A] and mCherry-14-3-3 or between wild type GFP-LRRK2 and inactive 14-3-3 polypeptide.

Commonly used FRET pairs include CFP (donor) and YFP (acceptor) as well as GFP (donor) and Cherry (acceptor). In cases where the donor and acceptor fluorophores are both excited with the same excitation light wavelength, e.g. in case of the FRET pair GFP-YFP, a special kind of FRET termed enhanced acceptor fluorescence (EAF) can be detected. Examples of further references concerning FRET techniques include Wallrabe & Periasamy (2005) Current Opinion in Biotechnology Volume 16, Issue 1, February 2005, Pages 19-27; Imaging protein molecules using FRET and FLIM microscopy; Ai et al (2008) *Nature Methods* 5, 401-403 Fluorescent protein FRET pairs for ratiometric imaging of dual biosensors; Shaner et al. (2004) Nat Biotechnol 22: 1567-1572 Improved monomeric red, orange and yellow fluorescent proteins derived from *Discosoma* sp. red fluorescent protein.

Assessing the effect of exposing the cell-based system comprising LRRK2 to the test compound on the phosphorylation state of Ser910 and/or Ser935 of the LRRK2; and/or assessing the effect of exposing the cell-based system comprising LRRK2 to the test compound on the binding of the LRRK2 to a 14-3-3 polypeptide may be done by (or further assessed by) assessing the subcellular localisation of LRRK2. It is considered that reducing the phosphorylation of Ser910 and/or Ser935 and/or reducing the binding of LRRK2 to a 14-3-3 polypeptide increases the amount of LRRK2 polypeptide present in cytoplasmic pools (as opposed to being diffusely located throughout the cytoplasm). The subcellular location of LRRK2 may be assessed using techniques well known to those skilled in the art, for example using immunohistochemistry or fluorescence microscopy, for example using a recombinant LRRK2 polypeptide with a fluorescent protein (for example GFP) tag. Examples of such techniques are given in the Examples.

In an embodiment, the method of the invention may comprise or further comprise the step of assessing the effect of exposing the cell-based system comprising LRRK2 to the test compound on the subcellular location of LRRK2.

The cell based system may be an in vitro cell system. For example, the assay may be performed on cell lines. Examples of suitable cell lines are considered to include Swiss 3T3 cells or HEK-293 cells. Other suitable cells include, for example, EBV transformed lymphoblastoid cells derived from a human subject expressing wild-type LRRK2, or from a human subject homozygous for LRRK2[G2019S] (or other LRRK2 mutant associated with Parkinsonism). A neuronal cell line may also be used. Suitable cell lines may also be cell lines that express a recombinant LRRK2 and/or recombinant 14-3-3 polypeptide. Suitable cells for such expression are considered to include T-Rex cells, as described in the Examples. The cells, for example T-Rex cells may express the recombinant LRRK2 or recombinant 14-3-3 polypeptide in an inducible manner, as will be well known to those skilled in the art. For example, cells may be induced to express the desired recombinant polypeptide by inclusion of doxycycline in the culture medium, for example as described in the Examples.

The 14-3-3 polypeptide may typically be or comprise the human beta, eta, theta, zeta, gamma or epsilon isoform. It is preferred that the 14-3-3 polypeptide is not solely the human sigma isoform. Examples of 14-3-3 polypeptide sequences are shown below. The skilled person will readily be able to identify other 14-3-3 polypeptide sequences from databases. For example, the Homologene feature of the NCBI database may be used.

```
Human 14-3-3 beta
                                    SEQ ID NO: 1
MTMDKSELVQKAKLAEQAERYDDMAAAMKAVTEQGHELSNEERNLLSV
AYKNVVGARRSSWRVISSIEQKTERNEKKQQMGKEYREKIEAELQDIC
NDVLELLDKYLIPNATQPESKVFYLKMKGDYFRYLSEVASGDNKQTTV
SNSQQAYQEAFEISKKEMQPTHPIRLGLALNFSVFYYEILNSPEKACS
LAKTAFDEAIAELDTLNEESYKDSTLIMQLLRDNLTLWTSENQGDEGD
AGEGEN Mouse 14-3-3 beta
                                    SEQ ID NO: 2
MTMDKSELVQKAKLAEQAERYDDMAAAMKAVTEQGHELSNEERNLLSV
AYKNVVGARRSSWRVISSIEQKTERNEKKQQMGKEYREKIEAELQDIC
NDVLELLDKYLILNATQAESKVFYLKMKGDYFRYLSEVASGENKQTTV
SNSQQAYQEAFEISKKEMQPTHPIRLGLALNFSVFYYEILNSPEKACS
LAKTAFDEAIAELDTLNEESYKDSTLIMQLLRDNLTLWTSENQGDEGD
AGEGEN Human 14-3-3 epsilon
                                    SEQ ID NO: 3
MDDREDLVYQAKLAEQAERYDEMVESMKKVAGMDVELTVEERNLLSVA
YKNVIGARRASWRIISSIEQKEENKGGEDKLKMIREYRQMVETELKLI
CCDILDVLDKHLIPAANTGESKVFYYKMKGDYHRYLAEFATGNDRKEA
AENSLVAYKAASDIAMTELPPTHPIRLGLALNFSVFYYEILNSPDRAC
RLAKAAFDDAIAELDTLSEESYKDSTLIMQLLRDNLTLWTSDMQGDGE
EQNKEALQDVEDENQ Mouse 14-3-3 epsilon
                                    SEQ ID NO: 4
MDDREDLVYQAKLAEQAERYDEMVESMKKVAGMDVELTVEERNLLSVA
YKNVIGARRASWRIISSIEQKEENKGGEDKLKMIREYRQMVETELKLI
CCDILDVQDKHLIPAANTGESKVFYYKMKGDYHRYLAEFATGNDRKEA
AENSLVAYKAASDIAMTELPPTHPIRLGLALNFSVFYYEILNSPDRAC
RLAKAAFDDAIAELDTLSEESYKDSTLIMQLLRDNLTLWTSDMQGDGE
EQNKEALQDVEDENQ Human 14-3-3 eta
                                    SEQ ID NO: 5
MGDREQLLQRARLAEQAERYDDMASAMKAVTELNEPLSNEDRNLLSVA
YKNVVGARRSSWRVISSIEQKTMADGNEKKLEKVKAYREKIEKELETV
CNDVLSLLDKFLIKNCNDFQYESKVFYLKMKGDYYRYLAEVASGEKKN
SVVEASEAAYKEAFEISKEQMQPTHPIRLGLALNFSVFYYEIQNAPEQ
ACLLAKQAFDDAIAELDTLNEDSYKDSTLIMQLLRDNLTLWTSDQQDE
EAGEGN Mouse 14-3-3 eta
                                    SEQ ID NO: 6
MGDREQLLQRARLAEQAERYDDMASAMKAVTELNEPLSNEDRNLLSVA
YKNVVGARRSSWRVISSIEQKTMADGNEKKLEKVKAYREKIEKELETV
CNDVLALLDKFLIKNCNDFQYESKVFYLKMKGDYYRYLAEVASGEKKN
SVVEASEAAYKEAFEISKEHMQPTHPIRLGLALNFSVFYYEIQNAPEQ
ACLLAKQAFDDAIAELDTLNEDSYKDSTLIMQLLRDNLTLWTSDQQDE
EAGEGN Human 14-3-3 gamma
                                    SEQ ID NO: 7
MVDREQLVQKARLAEQAERYDDMAAAMKNVTELNEPLSNEERNLLSVA
YKNVVGARRSSWRVISSIEQKTSADGNEKKIEMVRAYREKIEKELEAV
CQDVLSLLDNYLIKNCSETQYESKVFYLKMKGDYYRYLAEVATGEKRA
TVVESSEKAYSEAHEISKEHMQPTHPIRLGLALNYSVFYYEIQNAPEQ
ACHLAKTAFDDAIAELDTLNEDSYKDSTLIMQLLRDNLTLWTSDQQDD
DGGEGNN Mouse 14-3-3 gamma
                                    SEQ ID NO: 8
MVDREQLVQKARLAEQAERYDDMAAAMKNVTELNEPLSNEERNLLSVA
YKNVVGARRSSWRVISSIEQKTSADGNEKKIEMVRAYREKIEKELEAV
CQDVLSLLDNYLIKNCSETQYESKVFYLKMKGDYYRYLAEVATGEKRA
TVVESSEKAYSEAHEISKEHMQPTHPIRLGLALNYSVFYYEIQNAPEQ
ACHLAKTAFDDAIAELDTLNEDSYKDSTLIMQLLRDNLTLWTSDQQDD
DGGEGNN Human 14-3-3 theta
                                    SEQ ID NO: 9
MEKTELIQKAKLAEQAERYDDMATCMKAVTEQGAELSNEERNLLSVAY
KNVVGGRRSAWRVISSIEQKTDTSDKKLQLIKDYREKVESELRSICTT
VLELLDKYLIANATNPESKVFYLKMKGDYFRYLAEVACGDDRKQTIDN
SQGAYQEAFDISKKEMQPTHPIRLGLALNFSVFYYEILNNPELACTLA
KTAFDEAIAELDTLNEDSYKDSTLIMQLLRDNLTLWTSDSAGEECDAA
EGAEN Mouse 14-3-3 theta
                                    SEQ ID NO: 10
MEKTELIQKAKLAEQAERYDDMATCMKAVTEQGAELSNEERNLLSVAY
KNVVGGRRSAWRVISSIEQKTDTSDKKLQLIKDYREKVESELRSICTT
VLELLDKYLIANATNPESKVFYLKMKGDYFRYLAEVACGDDRKQTIEN
SQGAYQEAFDISKKEMQPTHPIRLGLALNFSVFYYEILNNPELACTLA
KTAFDEAIAELDTLNEDSYKDSTLIMQLLRDNLTLWTSDSAGEECDAA
EGAEN Human 14-3-3 zeta
                                    SEQ ID NO: 11
MDKNELVQKAKLAEQAERYDDMAACMKSVTEQGAELSNEERNLLSVAY
KNVVGARRSSWRVVSSIEQKTEGAEKKQQMAREYREKIETELRDICND
VLSLLEKFLIPNASQAESKVFYLKMKGDYYRYLAEVAAGDDKKGIVDQ
SQQAYQEAFEISKKEMQPTHPIRLGLALNFSVFYYEILNSPEKACSLA
KTAFDEAIAELDTLSEESYKDSTLIMQLLRDNLTLWTSDTQGDEAEAG
EGGEN Mouse 14-3-3 zeta
                                    SEQ ID NO: 12
MDKNELVQKAKLAEQAERYDDMAACMKSVTEQGAELSNEERNLLSVAY
KNVVGARRSSWRVVSSIEQKTEGAEKKQQMAREYREKIETELRDICND
VLSLLEKFLIPNASQPESKVFYLKMKGDYYRYLAEVAAGDDKKGIVDQ
SQQAYQEAFEISKKEMQPTHPIRLGLALNFSVFYYEILNSPEKACSLA
KTAFDEAIAELDTLSEESYKDSTLIMQLLRDNLTLWTSDTQGDEAEAG
EGGEN Human 14-3-3 sigma
                                    SEQ ID NO: 13
MERASLIQKAKLAEQAERYEDMAAFMKGAVEKGEELSCEERNLLSVAY
KNVVGGQRAAWRVLSSIEQKSNEEGSEEKGPEVREYREKVETELQGVC
DTVLGLLDSHLIKEAGDAESRVFYLKMKGDYYRYLAEVATGDDKKRII
DSARSAYQEAMDISKKEMPPTNPIRLGLALNFSVFHYEIANSPEEAIS
LAKTTFDEAMADLHTLSEDSYKDSTLIMQLLRDNLTLWTADNAGEEGG
EAPQEPQS Mouse 14-3-3 sigma
                                    SEQ ID NO: 14
MERASLIQKAKLAEQAERYEDMAAFMKSAVEKGEELSCEERNLLSVAY
KNVVGGQRAAWRVLSSIEQKSNEEGSEEKGPEVKEYREKVETELRGVC
DTVLGLLDSHLIKGAGDAESRVFYLKMKGDYYRYLAEVATGDDKKRII
DSARSAYQEAMDISKKEMPPTNPIRLGLALNFSVFHYEIANSPEEAIS
LAKTTFDEAMADLHTLSEDSYKDSTLIMQLLRDNLTLWTADSAGEEGG
EAPEEPQS
```

The 14-3-3 polypeptide may comprise a tag sequence, as will be well known to those skilled in the art. For example, a tag useful in a FRET system may be used. For example a fluorescent protein tag, for example a Cherry tag may be used. It is considered that the 14-3-3 polypeptide may be in the form of a dimer (typically a homodimer) when bound to the LRRK2 polypeptide, as is generally considered to be the case for binding of 14-3-3 polypeptide to a phosphorylated polypeptide. Typically the 14-3-3 polypeptide is a full length 14-3-3 polypeptide.

The recombinant LRRK2 may be an LRRK2 that is tagged, for example with a fluorescent polypeptide moiety, for example a GST moiety or Green Fluorescent Protein (GFP) moiety or a FLAG moiety, for example as described in the Examples. The LRRK2 polypeptide may be wild-type LRRK2 or may be an LRRK2 mutant, for example LRRK2 [G2019S]. Typically the LRRK2 does not have the drug-resistant A2016T mutation. Typically the LRRK2 is not a kinase inactive mutant. Typically the LRRK2 has Serine residues at positions 910 and 935 (numbering of full length wild type LRRK2). Typically the sequences surrounding these serine residues are also unchanged from wild-type LRKK2. In particular, residues identified in FIG. 3G typically are retained i.e. basic residues −3 and −4 positions, Ser residue at the −2 position, Asn at the −1 position and a large hydrophobic residue at the +1 position. Typically the LRRK2 is full length LRRK2.

Control cells in which the LRRK2 has the drug-resistant A2016T mutation may be useful. Control cells in which the LRRK2 has a mutation (for example to Alanine) at one or both of positions 910 and 935 (numbering of full length wild type LRRK2) may be useful. Control cells in which the LRRK2 is a kinase inactive mutant may also be useful.

Cell lines stably expressing FLAG or GST tagged LRRK2 may be particularly useful. Cell lines expressing LRRK2 and a 14-3-3 polypeptide tagged with fluorescent tags compatible for performing FRET may be useful. Examples of FRET donor-acceptor pairs will be well known to those skilled in the art and some examples are given above. For example the LRRK2 may be tagged with a GFP moiety whilst the 14-3-3 polypeptide may be tagged with a Cherry moiety.

Neuronal cell lines or blood cell lines may also be particularly useful. Any cell line where LRRK2 is endogenously expressed may also be useful.

The LRRK2 is typically human LRRK2, but may alternatively be another mammalian LRRK2, for example LRRK2 of a laboratory animal or of a tissue or organ assay system considered useful in assessing a potential inhibitor of LRRK2. Thus, the LRRK2 may be a laboratory rodent LRRK2 (for example mouse, rabbit or rat) or may be a laboratory primate LRRK2, for example a monkey LRRK2. An assay of the present invention may, for example, be useful in assessing the effect of a test compound on LRRK2 in brain tissue of a laboratory animal, for example a mouse or a monkey.

The LRRK2 polypeptide can be human LRRK2 having a naturally occurring mutation of wild type human LRRK2; or a fusion thereof. The naturally occurring mutation of human LRRK2 may be a mutation associated with Parkinson's Disease (PD). As noted above, the mutation, using the numbering of wild type human LRRK2, may be G2019S. This mutation is considered to enhance the protein kinase activity of LRRK2, as discussed further in Jaleel et al (2007) supra or in PCT/GB2008/001211, supra.

The mutation, using the numbering of wild type human LRRK2, may alternatively be R1441C, R1441G, Y1699C, R1914H, I2012T, I2020T, or G2385R. LRRK2 with mutations R1441C, R1441G, Y1699C or T2356I is considered to have similar protein kinase activity to wild-type LRRK2. LRRK2 with mutation R1914H or I2012T is considered to be nearly inactive. LRRK2 with mutation R1441C or Y1699C is considered to accumulate in cytoplasmic pools (rather than being diffusely present throughout the cytoplasm) to a greater extent than wild-type LRRK2. LRRK2 with mutation I2020T is considered to have activity intermediate between wild-type LRRK2 and LRRK2 with mutation R1914H or I2012T. LRRK2 with mutation G2385R is also considered to be nearly inactive. The activities of further mutants are shown in FIG. 17 of PCT/GB2008/001211, supra.

It may be helpful to test compounds against more than one LRRK2 polypeptide; for example against more than one mutant LRRK2 polypeptide. This may assist in deciding on further compounds to design and test.

It is particularly preferred, although not essential, that the LRRK2 polypeptide has at least 30% of the enzyme activity of full-length human LRRK2 with respect to the phosphorylation of full-length human moesin on residue Thr558 or Thr526; or the phosphorylation of a peptide substrate encompassing such a residue (for example RLGRDKYKTLRQIRQ or RLGRDKYKTLRQIRQGNTKQR or RLGWWRFYTL-RRARQGNTKQR. It is more preferred if the LRRK2 polypeptide has at least 50%, preferably at least 70% and more preferably at least 90% of the enzyme activity of full-length human LRRK2 with respect to the phosphorylation of full-length human moesin on residue Thr558 or Thr526; or the phosphorylation of a peptide substrate encompassing such a residue, as discussed above; or of RLGWWRFYTL-RRARQGNTKQR.

Accession numbers for mammalian LRRK2 sequences in the NCBI database include:
AAV63975.1 human
XP_001168494.1 *Pan troglodytes*, (chimpanzee)
XP_615760.3 *Bos Taurus* (domestic cow)
XP_543734.2 *Canis familiaris* (dog)
NP_080006.2 *Mus musculus* (mouse)
XP_235581.4 *Rattus norvegicus* (rat)

Numerous further examples of mammalian and non-mammalian LRRK2 polypeptide sequences can be accessed in the sequence databases accessible from the NCBI Medline™ service, as will be well known to the person skilled in the art.

By "variants" of a polypeptide we include insertions, deletions and substitutions, either conservative or non-conservative. In particular we include variants of the polypeptide where such changes do not substantially alter the protein kinase activity or ability to be phosphorylated, or the interaction between LRRK2 and 14-3-3 polypeptide, as appropriate. The skilled person will readily be able to design and test appropriate variants, based on, for example, comparison of sequences of examples of each polypeptide, for example from different species. The skilled person will readily be able to determine where insertions or deletions can be made; or which residues can appropriately be left unchanged; replaced by a conservative substitution; or replaced by a non-conservative substitution. The variant polypeptides can readily be tested, for example as described in the Examples.

By "conservative substitutions" is intended combinations such as Gly, Ala; Val, Ile, Leu; Asp, Glu; Asn, Gln; Ser, Thr; Lys, Arg; and Phe, Tyr.

The three-letter or one letter amino acid code of the IUPAC-IUB Biochemical Nomenclature Commission is used herein, with the exception of the symbol Zaa, defined above. In particular, Xaa represents any amino acid. It is preferred that at least the amino acids corresponding to the consensus sequences defined herein are L-amino acids.

It is particularly preferred if the polypeptide variant has an amino acid sequence which has at least 65% identity with the amino acid sequence of the relevant human polypeptide, more preferably at least 70%, 71%, 72%, 73% or 74%, still more preferably at least 75%, yet still more preferably at least 80%, in further preference at least 85%, in still further preference at least 90% and most preferably at least 95% or 97% identity with the amino acid sequence of the relevant human polypeptide.

It is still further preferred if a protein kinase variant has an amino acid sequence which has at least 65% identity with the amino acid sequence of the catalytic domain of the human polypeptide, more preferably at least 70%, 71%, 72%, 73% or 74%, still more preferably at least 75%, yet still more preferably at least 80%, in further preference at least 83 or 85%, in still further preference at least 90% and most preferably at least 95% or 97% identity with the relevant human amino acid sequence.

It will be appreciated that the catalytic domain of a protein kinase-related polypeptide may be readily identified by a person skilled in the art, for example using sequence comparisons as described below. Protein kinases show a conserved catalytic core, as reviewed in Johnson et al (1996) *Cell*, 85, 149-158 and Taylor & Radzio-Andzelm (1994) *Structure* 2, 345-355. This core folds into a small N-terminal lobe largely comprising anti-parallel β-sheet, and a large C-terminal lobe which is mostly α-helical.

The percent sequence identity between two polypeptides may be determined using suitable computer programs, for example the GAP program of the University of Wisconsin Genetic Computing Group and it will be appreciated that percent identity is calculated in relation to polypeptides whose sequence has been aligned optimally.

The alignment may alternatively be carried out using the Clustal W program (Thompson et al., 1994). The parameters used may be as follows:

Fast pairwise alignment parameters: K-tuple(word) size; 1, window size; 5, gap penalty; 3, number of top diagonals; 5. Scoring method: x percent.

Multiple alignment parameters: gap open penalty; 10, gap extension penalty; 0.05.

Scoring matrix: BLOSUM.

The alignment may alternatively be carried out using the program T-Coffee, or EMBOSS.

The residue corresponding (equivalent) to, for example, Ser910 of full-length human LRRK2 may be identified by alignment of the sequence of the polypeptide with that of full-length human LRRK2 in such a way as to maximise the match between the sequences. The alignment may be carried out by visual inspection and/or by the use of suitable computer programs, for example the GAP program of the University of Wisconsin Genetic Computing Group, which will also allow the percent identity of the polypeptides to be calculated. The Align program (Pearson (1994) in: Methods in Molecular Biology, Computer Analysis of Sequence Data, Part II (Griffin, A M and Griffin, H G eds) pp 365-389, Humana Press, Clifton). Thus, residues identified in this manner are also "corresponding residues".

It will be appreciated that in the case of truncated forms of (for example) LRRK2 or in forms where simple replacements of amino acids have occurred it is facile to identify the "corresponding residue".

It is preferred that the polypeptides used in the screen are mammalian, preferably human (or a species useful in agriculture or as a domesticated or companion animal, for example dog, cat, horse, cow), including naturally occurring allelic variants (including splice variants). The polypeptides used in the screen may comprise a GST portion or may be biotinylated or otherwise tagged, for example with a 6His, HA, myc or other epitope tag, as known to those skilled in the art, or as mentioned above or as described in the Examples. This may be useful in purifying and/or detecting the polypeptide(s).

The effect of the compound may be determined by comparing the phosphorylation of residues Ser910 or Ser935, or the binding of 14-3-3 polypeptide, or the subcellular localization of LRRK2 in the presence of different concentrations of the compound, for example in the absence and in the presence of the compound, for example at a concentration of about 100 µM, 30 µM, 10 µM, 3 µM, 1 µM, 0.1 µM, 0.01 µM and/or 0.001 µM.

It may be useful to compare the effect of the test compound with the effect of compounds considered to be inhibitors of LRRK2, for example H-1152 and/or sunitinib.

The cell based system may be an ex vivo cell system. The cells may be in the form of a sample of tissue or an organ. The sample may be a sample of blood, kidney, brain or spleen (or other tissue in which LRRK2 is highly expressed).

The cell based system may be an in vivo system. For example the cell-based system comprising LRRK2 may have been exposed to the test compound in a test animal. Suitable ways of exposing a test animal to the test compound will be well known to those skilled in the art. Typically the compound may be formulated for administration by injection or for oral administration but other administration routes may be used, as will be apparent to the skilled person. A sample for analysis may be obtained from the test animal by invasive, minimally invasive or non-invasive techniques. For example, a blood sample (minimally invasive) may be analysed; or a sample of brain tissue (invasive), which may require sacrifice of the animal.

The assessing of the phosphorylation state of Ser910 and/or Ser935 of the LRRK2; and/or the assessing of the binding of the LRRK2 to a 14-3-3 polypeptide and/or the assessing of the subcellular location of LRRK2 may be performed on cells obtained from the test animal. For example, the cells obtained from the test animal may be cells obtained in blood from the test animal.

The cell based system may be a lymphoblastoid cell-based system. Lymphoblastoid cells may be present in a blood sample from a test animal. A macrophage cell line (for example RAW cell line) system may be useful. A system making use of macrophages obtained from blood from human volunteers may also be useful.

The method is considered to be useful in identifying compounds that modulate, for example inhibit, the protein kinase activity of LRRK2 (or the phosphorylation of Ser910 and/or Ser935 or interaction between LRRK2 and a 14-3-3 polypeptide or accumulation of LRRK2 in cytoplasmic pools) in a cell-based system. A compound that modulates, for example inhibits, the protein kinase activity of LRRK2 (or the phosphorylation of Ser910 and/or Ser935 or interaction between LRRK2 and a 14-3-3 polypeptide or accumulation of LRRK2 in cytoplasmic pools) in a cell-based system may be useful in the treatment of Parkinson's Disease (for example idiopathic Parkinson's Disease or late-onset Parkinson's Disease) or Parkinsonism.

A compound that modulates, for example inhibits, the protein kinase activity of LRRK2 (or the phosphorylation of Ser910 and/or Ser935 or interaction between LRRK2 and a 14-3-3 polypeptide or accumulation of LRRK2 in cytoplasmic pools) in a cell-based system, may also be useful in other neurodegenerative conditions.

The compound may be one which binds to or near a region of contact between a LRRK2 polypeptide and a substrate polypeptide, or may be one which binds to another region and, for example, induces a conformational or allosteric change which stabilises (or destabilises) the complex; or promotes (or inhibits) its formation. The compound may bind to the LRRK2 polypeptide or to the substrate polypeptide so as to increase the LRRK2 polypeptide protein kinase activity by an allosteric effect. This allosteric effect may be an allosteric effect that is involved in the natural regulation of the LRRK2 polypeptide's activity.

The compounds identified in the methods may themselves be useful as a drug or they may represent lead compounds for the design and synthesis of more efficacious compounds.

The compound may be a drug-like compound or lead compound for the development of a drug-like compound for each of the above methods of identifying a compound. It will be appreciated that the said methods may be useful as screening assays in the development of pharmaceutical compounds or drugs, as well known to those skilled in the art.

The term "drug-like compound" is well known to those skilled in the art, and may include the meaning of a compound that has characteristics that may make it suitable for use in medicine, for example as the active ingredient in a medicament. Thus, for example, a drug-like compound may be a molecule that may be synthesised by the techniques of organic chemistry, less preferably by techniques of molecular biology or biochemistry, and is preferably a small molecule, which may be of less than 5000 daltons. A drug-like compound may additionally exhibit features of selective interaction with a particular protein or proteins and be bioavailable and/or able to penetrate cellular membranes, but it will be appreciated that these features are not essential.

The term "lead compound" is similarly well known to those skilled in the art, and may include the meaning that the compound, whilst not itself suitable for use as a drug (for example because it is only weakly potent against its intended target, non-selective in its action, unstable, difficult to synthesise or has poor bioavailability) may provide a starting-point for the design of other compounds that may have more desirable characteristics.

It will be understood that it will be desirable to identify compounds that may modulate the activity of the protein kinase in vivo. Thus it will be understood that reagents and conditions used in the method may be chosen such that the interactions between, for example, the LRRK2 polypeptide and a substrate polypeptide, are substantially the same as between the human LRRK2 and an endogenous human substrate polypeptide. Typically a method of the invention may be performed in a human cell-based system, optionally expressing human recombinant polypeptides. It will be appreciated that the compound may bind to the LRRK2 polypeptide, or may bind to the substrate polypeptide.

The compounds that are tested in the screening methods of the invention or in other assays in which the ability of a compound to modulate the protein kinase activity of an LRRK2 polypeptide, may be measured, may be (but do not have to be) compounds that have been selected and/or designed (including modified) using molecular modelling techniques, for example using computer techniques. The selected or designed compound may be synthesised (if not already synthesised) and tested for its effect on the LRRK2 polypeptide, for example its effect on the protein kinase activity. The compound may be tested in a screening method of the invention.

The compounds that are tested may be compounds that are already considered likely to be able to modulate the activity of a protein kinase; or may be compounds that have not been selected on the basis of being likely to modulate the activity of a protein kinase. Thus, the compounds tested may be compounds forming at least part of a general, unselected compound bank; or may alternatively be compounds forming at least part of a pre-selected compound bank, for example a bank of compounds pre-selected on the basis of being considered likely to modulate the activity of a protein kinase.

It will be appreciated that screening assays which are capable of high throughput operation will be particularly preferred.

As will be apparent to those skilled in the art, it may be desirable to assess what effect the compound has on other protein kinases. For example, it may be desirable to assess the effect of the compound on phosphorylation of substrates of other protein kinases, for example substrates of RockII, in order to distinguish between LRRK2 and ROCK inhibitors. For example, as shown in, for example, FIGS. 20 and 22 of PCT/GB2008/001211, supra or discussed in the legends thereto, the substrate preferences of LRRK2 and Rock-II are different. As an example, LRRK2 does not phosphorylate MYPT, while RockII does phosphorylate MYPT.

Information on PD models, biomarkers and assessment techniques, in/against which it may be appropriate further to test compounds identified using the screening methods described herein, can be found at, for example, the following links, which are representative of information available to those skilled in the art.
http://www.ninds.nih.gov/about_ninds/plans/nihparkinsons_agenda.htm#Models
http://www.sciencedaily.com/releases/2006/07/060729134653.htm (mouse model with mitochondrial disturbance)
http://www.sciencedaily.com/releases/2004/10/041005074846.htm (embryonic stem cell model)
http://en.wikipedia.org/wiki/Parkinson's_disease PD animal models include the 6-hydroxydopamine treated rodent and the MPTP treated primate. Both are based on toxic destruction of dopaminergic brain cells (and some other types), and usually employ young, otherwise healthy animals. Because these models reproduce some key features of Parkinson's disease, they are considered useful to test emerging new therapies.

Compounds may also be subjected to other tests, for example toxicology or metabolism tests, as is well known to those skilled in the art.

The screening method of the invention may comprise the step of synthesising, purifying and/or formulating the selected compound. The compound may be formulated for pharmaceutical use, for example for use in in vivo trials in animals or humans.

A further aspect of the invention provides an antibody that binds specifically to LRRK2 phosphorylated at Ser910; or an antibody that binds specifically to LRRK2 phosphorylated at Ser935; or an antibody that binds specifically to LRRK2 that is not phosphorylated at Ser910; or an antibody that binds specifically to LRRK2 that is not phosphorylated at Ser935.

A further aspect of the invention provides a kit of parts comprising two or more of: 1) an antibody that binds specifically to LRRK2 phosphorylated at Ser910 or an antibody that binds specifically to LRRK2 that is not phosphorylated at Ser910; 2) an antibody that binds specifically to LRRK2 phosphorylated at Ser935, or an antibody that binds specifically to LRRK2 that is not phosphorylated at Ser935; 3) a 14-3-3 polypeptide (which may, for example, be labeled, for example with digoxygenin), or an antibody that specifically binds to a 14-3-3 polypeptide; and 4) a fluorescently labeled LRRK2 polypeptide, or polynucleotide encoding a fluorescently labeled LRRK2.

A further aspect of the invention provides the use of: 1) an antibody that binds specifically to LRRK2 phosphorylated at Ser910; 2) an antibody that binds specifically to LRRK2 phosphorylated at Ser935; 3) a 14-3-3 polypeptide, or an antibody that specifically binds to a 14-3-3 polypeptide; and/or 4) a fluorescently labeled LRRK2 polypeptide, or polynucleotide encoding a fluorescently labeled LRRK2, in a method for assessing the effect of a test compound on LRRK2 in a cell-based system.

A further aspect of the invention provides a purified preparation or kit of parts comprising an LRRK2 polypeptide or polynucleotide (i.e. a polynucleotide encoding an LRRK2 polypeptide) or antibody binding specifically to LRRK2; and a 14-3-3 polypeptide or polynucleotide (i.e. a polynucleotide encoding a 14-3-3 polypeptide) or antibody binding specifically to a 14-3-3 polypeptide. The preparation or kit may, for example, comprise a recombinant LRRK2 polynucleotide or polypeptide and a recombinant 14-3-3 polypeptide or polynucleotide. The LRRK2 and 14-3-3 may comprise fluorescent tags suitable for use in a FRET system, as discussed above. The preparation or kit may comprise immunoprecipitated LRRK2 polypeptide and 14-3-3 polypeptide. The preparation or kit may comprise an antibody that specifically binds to LRRK2 and a 14-3-3 polypeptide (which may, for example, be labeled, for example with digoxygenin) or an antibody that specifically binds to a 14-3-3 polypeptide.

The preparation or kit may be useful in an assay of the invention.

By the term "antibody" is included synthetic antibodies and fragments and variants (for example as discussed above) of whole antibodies which retain the antigen binding site. The antibody may be a monoclonal antibody, but may also be a polyclonal antibody preparation, a part or parts thereof (for example an $F_{ab}$ fragment or $F(ab')_2$) or a synthetic antibody or part thereof. Fab, Fv, ScFv and dAb antibody fragments can all be expressed in and secreted from *E. coli*, thus allowing the facile production of large amounts of the said fragments. By "ScFv molecules" is meant molecules wherein the $V_H$ and $V_L$ partner domains are linked via a flexible oligopeptide. IgG class antibodies are preferred.

Suitable monoclonal antibodies to selected antigens may be prepared by known techniques, for example those disclosed in "Monoclonal Antibodies: A manual of techniques", H. Zola (CRC Press, 1988) and in "Monoclonal Hybridoma Antibodies: techniques and Applications", J G R Hurrell (CRC Press, 1982), modified as indicated above. Bispecific antibodies may be prepared by cell fusion, by reassociation of monovalent fragments or by chemical cross-linking of whole antibodies. Methods for preparing bispecific antibodies are disclosed in Corvalen et al, (1987) *Cancer Immunol. Immunother.* 24, 127-132 and 133-137 and 138-143.

A general review of the techniques involved in the synthesis of antibody fragments which retain their specific binding sites is to be found in Winter & Milstein (1991) *Nature* 349, 293-299.

By "purified" is meant that the preparation has been at least partially separated from other components in the presence of which it has been formed, for example other components of a recombinant cell. Examples of methods of purification that may be used are described in the Examples.

The preparation may be substantially pure. By "substantially pure" we mean that the said polypeptide(s) are substantially free of other proteins. Thus, we include any composition that includes at least 2, 3, 4, 5, 10, 15, 20 or 30% of the protein content by weight as the said polypeptides, preferably at least 50%, more preferably at least 70%, still more preferably at least 90% and most preferably at least 95% of the protein content is the said polypeptides.

Thus, the invention also includes compositions comprising the said polypeptides and a contaminant wherein the contaminant comprises less than 96, 95, 94, 90, 85, 80 or 70% of the composition by weight, preferably less than 50% of the composition, more preferably less than 30% of the composition, still more preferably less than 10% of the composition and most preferably less than 5% of the composition by weight.

The invention also includes the substantially pure said polypeptides when combined with other components ex vivo, said other components not being all of the components found in the cell in which said polypeptides are found.

A further aspect of the invention includes a method of characterising an LRRK2 mutant, for example an LRRK2 mutant found in a patient with Parkinson's Disease, the method comprising the steps of: a) assessing the phosphorylation state of Ser910 and/or Ser935 of the LRRK2 mutant; and/or b) assessing the ability of the LRRK2 mutant to bind a 14-3-3 polypeptide. The method may comprise, or further comprise, the step of assessing the subcellular location of the LRRK2 mutant, when expressed in a cell-based system. The assessing steps may be performed using the antibodies, reagents and cell-based systems described above.

All documents referred to herein are hereby incorporated by reference. For the avoidance of doubt Jaleel et al (2007) Biochem J 405(2), 307-317, PCT/GB2008/001211 and PCT/GB2009/002047 are hereby incorporated by reference.

The listing or discussion of an apparently prior-published document in this specification should not necessarily be taken as an acknowledgement that the document is part of the state of the art or is common general knowledge.

The invention is now described in more detail by reference to the following, non-limiting, Figures and Examples.

BRIEF DESCRIPTION OF THE FIGURES

FIG. 1. Quantitative mass spectrometry identifies 14-3-3 as a major LRRK2-interactor. 293-HEK cells stably expressing GFP, wild type full-length GFP-LRRK2 or full-length GFP-LRRK2[G2019S] mutant were cultured for multiple passages in either R6K4 SILAC media (GFP-LRRK2 or GFP-LRRK2[G2019S]) or normal R0K0 SILAC media (GFP). Cells were lysed and equal amounts of lysates from GFP and GFP-LRRK2 (A & C) or GFP and GFP-LRRK2[G2019S] (B & D) were mixed. Immunoprecipitations were undertaken employing an anti-GFP antibody and electrophoresed on a SDS-polyacrylamide gel, which was stained with colloidal blue (A & B). Migration of LRRK2 band is indicated with an arrowhead and GFP band is indicated with an arrow. Molecular weights of markers are indicated on the left and right of the gels. The entire lane from each gel was excised, digested with trypsin and processed for mass spectrometry. Each sample was analyzed by Orbitrap mass spectrometry and quantitated using MaxQuant (version 13.13.10) [28] and a summary of results are presented in tabular format. The number of peptides and percent of sequence coverage corresponding to the indicated protein which were quantitated are shown along with the ratios of enrichment for labeled versus unlabeled peptides for each comparison of GFP vs. wild type LRRK2 (C) and GFP vs. LRRK2 [G2019S] (D). The posterior error probability PEP is shown, which measures the accuracy of MaxQuant quantitation where the closer to zero the higher the probability of specific interaction [28].

FIG. 5. Evidence that LRRK2 kinase activity controls Ser910 and Ser935 phosphorylation as well as 14-3-3 binding. A & B) HEK-293 cells transiently expressing the indicated forms of Flag-LRRK2 were treated with DMSO vehicle control or indicated concentrations of H1152 or sunitinib for 90 minutes. Cells were lysed in lysis buffer supplemented with 0.5% NP40 and 150 mM and subjected to anti-FLAG immunoprecipitation. Immunoprecipitates were resolved on 4-12% Novex SDS-polyacrylamide gels and subjected to immunoblot with FLAG (total LRRK2), anti-pS910, anti-pS935 as well as a 14-3-3 overlay assay. Similar results were obtained in 2 separate experiments.

FIG. 8. 14-3-3 binding influences LRRK2 cytoplasmic localisation A.) Stable-inducible T-REx cells lines harbouring the indicated forms of LRRK2 were induced for 24 hours with 0.1 µg/ml doxycycline to induce expression of GFP-LRRK2. Equal amount of cell lysate from induced cells of each mutant was subjected to immunoblot analysis with anti-GFP antibodies to detect the fusion protein or anti-GAPDH as a loading control. B.) Fluorescent micrographs representative of cultures of the indicated forms GFP-LRRK2 are shown. Cytoplasmic pools of GFP-LRRK2 observed in the non-14-3-3 binding mutants are indicated with white arrowheads.

Figure 9:
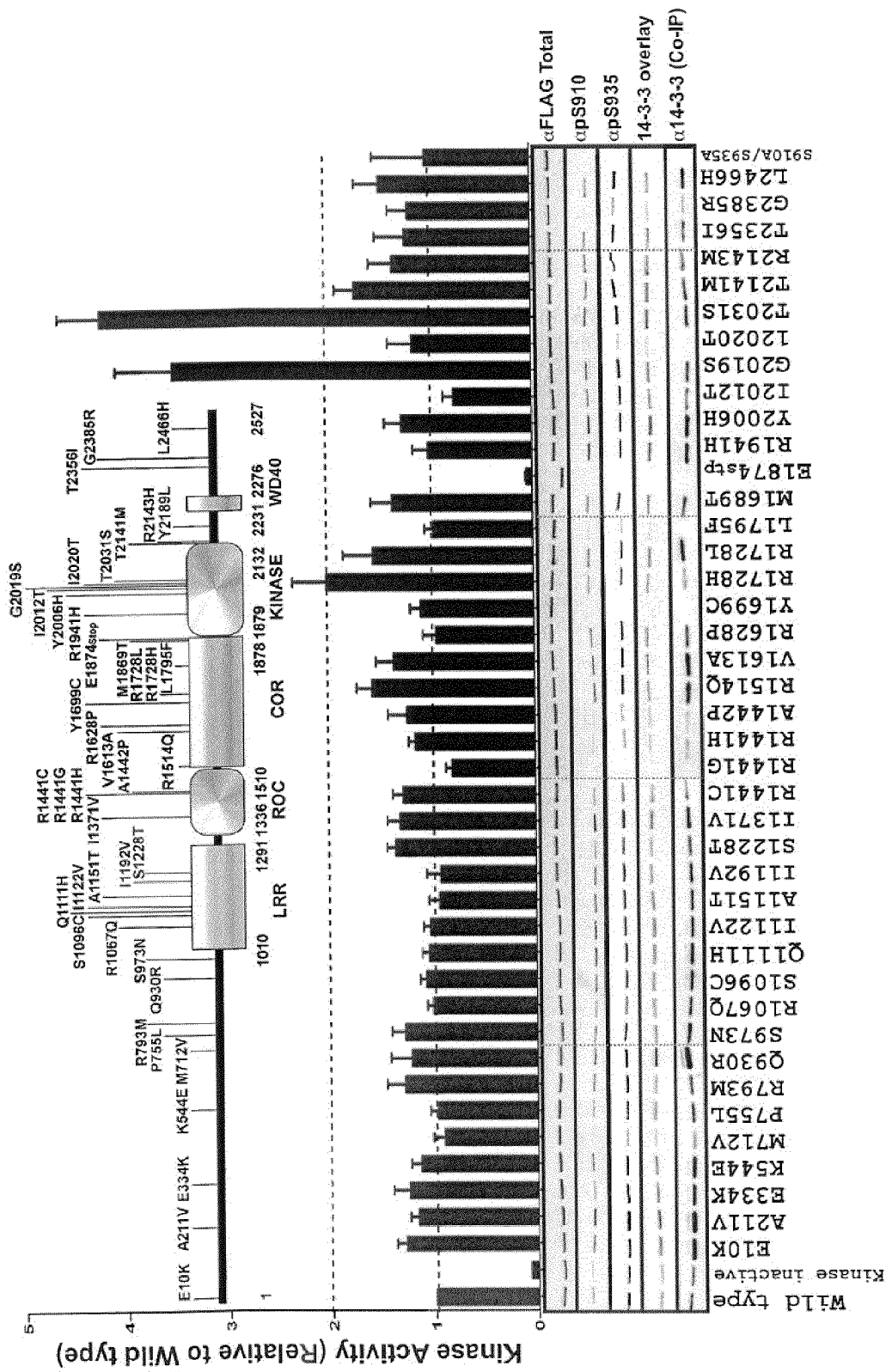

FIG. 9. Activity and 14-3-3 Binding of 41 Parkinson's disease associated LRRK2 mutants. The inset illustrates the domain structure of LRRK2 with the Leucine-Rich Repeats (LRR), Ras of Complex GTPase domain (ROC), Carboxy terminal of Roc (COR), and Kinase catalytic domain (Kinase) and the minimal WD40 repeat domain (WD40) annotated. Positions of the PD associated mutations are shown. The amino acid boundaries of the domains are indicated. The indicated variants of full length FLAG tagged LRRK2 were transiently expressed in HEK 293 cells and subjected to immunoprecipitation analysis. Kinase activity of immunoprecipitates was assessed against LRRKtide and specific activity was determined by quantitative anti-FLAG immunoblot analysis of LRRK2 using LICOR technology and was defined as cpm/LICOR. Wild type LRRK2 activity was set to 1 and the mutant activities are relative to wild type. Assays were performed in duplicate, for three experiments, bars are s.e.m. FLAG-LRRK2 immunoprecipitates were also subjected to immunoblot analysis with anti-FLAG, anti-pSer910 and anti-pSer935 antibodies. 14-3-3 binding to the LRRK2 variants was assessed by 14-3-3 far western analyses and 14-3-3 immunoblotting for co-precipitating 14-3-3.

Figure 10:
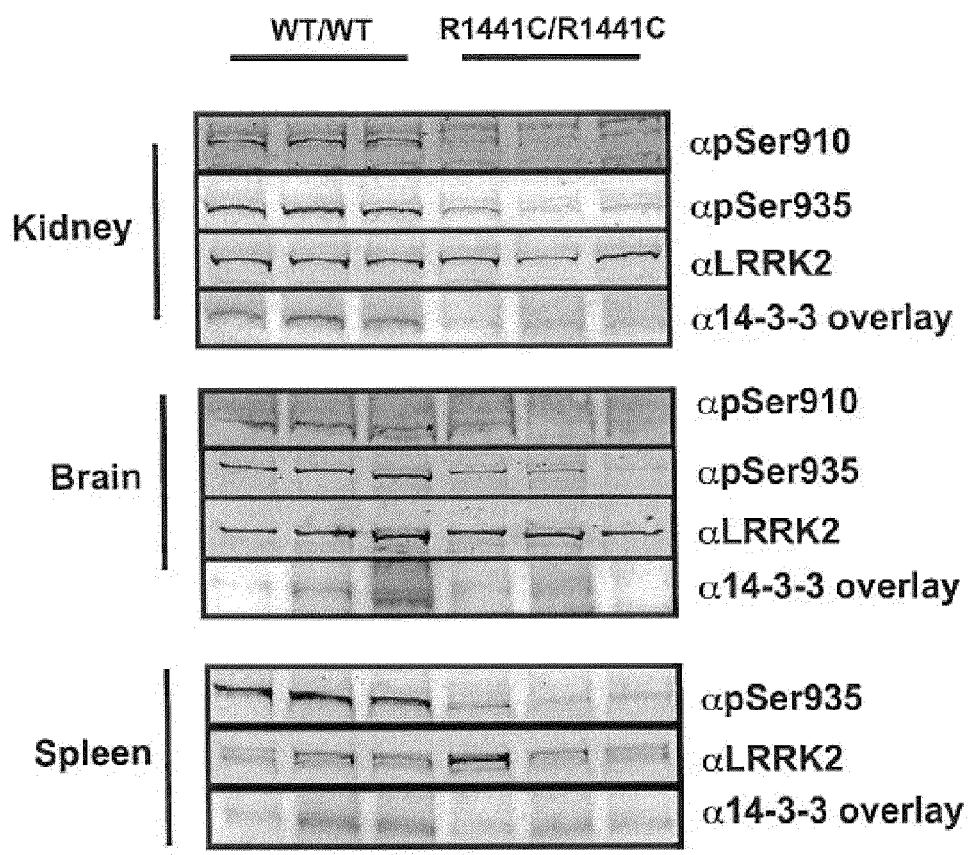

FIG. 10. Disruption of Ser910/Ser935 phosphorylation and 14-3-3 binding in LRRK2[R1441C] knockin mice. Brain, kidney and spleen tissue was rapidly excised from three homozygous LRRK2[R1441C] knockin mice and three wild type littermate controls and snap-frozen in liquid nitrogen. LRRK2 was immunoprecipitated from whole tissue lysate of brain, kidney or spleen. Immunoprecipitates were immunoblotted for phosphorylation of LRRK2 at Ser910 and Ser935 and for total LRRK2. Ability to interact with 14-3-3 binding was assessed by 14-3-3 far western analysis. Note insufficient sample from Spleen was available for measuring Ser910 phosphorylation.

FIG. 11. Localisation of 41 PD associated LRRK2 mutants. Parallel cultures of stable inducible T-REx cells lines harboring the indicated mutations were induced for 24 hours with 1 µg/ml doxycycline to induce expression of GFP-LRRK2. A.) Equal amount of cell lysate from induced cells of each mutant was subjected to immunoblot analysis with anti-GFP antibodies to detect the fusion protein or anti-ERK1 as a loading control. B.) Fluorescent micrographs representative of cultures of each PD associated mutant (panels 1-43) are shown. Cytoplasmic pools of GFP-LRRK2 are indicated with white arrowheads. Localization analyses were performed in duplicate, on two independently generated stable cell lines. Larger panels of each of the micrographs shown are presented in FIG. 12.

FIG. 12. Summary of the effects of 41 PD associated LRRK2 mutations. Kinase activity relative to wild type, where − indicates no detectable activity, + equals approximately no change and each fold increase represented by and additional +. Effects of phosphoserine 910 and 935 phosphorylation and direct 14-3-3 binding, where no change is represented by ++, + indicates a decrease in Ser910/Ser935 phosphorylation or 14-3-3 binding and − indicates no detectable Ser910/Ser935 phosphorylation or 14-3-3 binding. Localization is denoted as diffuse for diffuse cytoplasmic staining. Aggregate denotes the appearance of cytoplasmic pools. We have divided LRRK2 mutants into six groups. Group1 mutants display >2-fold increase in kinase activity, but normal 14-3-3 binding and diffuse localisation (green shading—*). Group 2 mutants display normal kinase activity but reduced Ser910/Ser935 phosphorylation as well as 14-3-3 binding and accumulate within cytoplasmic pools (peach shading—). Group 3 mutants display normal kinase activity but reduced Ser910/Ser935 phosphorylation as well as 14-3-3 binding and exhibit diffuse cytoplasmic localisation (blue shading—*). The Group 4 mutant displayed normal kinase activity, Ser910/Ser935 phosphorylation as well as 14-3-3 binding but accumulate within cytoplasmic pools (yellow shading—**). The Group 5 mutant displays no kinase activity, Ser910/Ser935 phosphorylation or 14-3-3 binding and localize diffusely (red shading—***). Group 6 mutants display properties similar to wild type LRRK2 (non-shaded).

Figure 13:
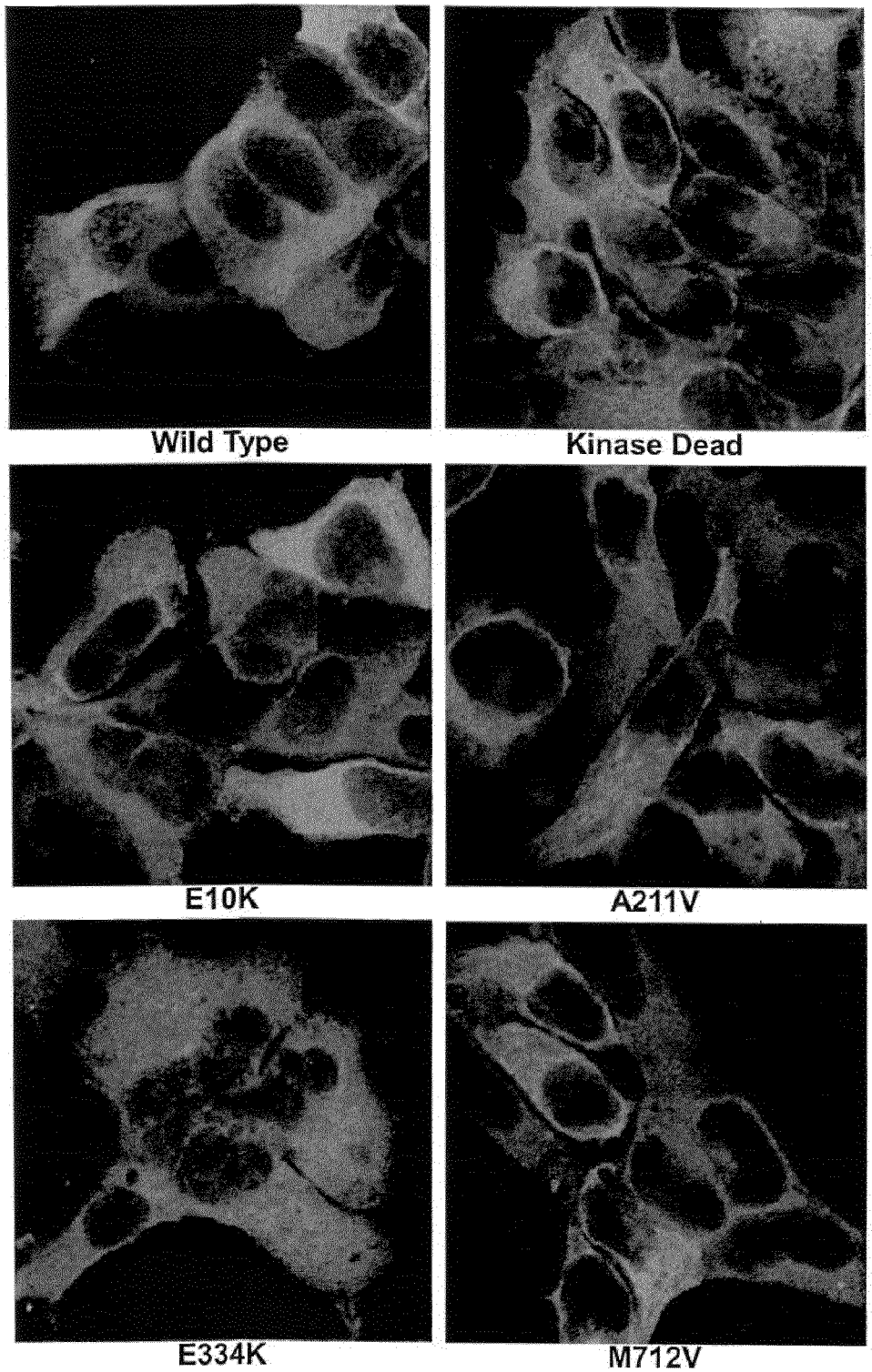
Figure 13:
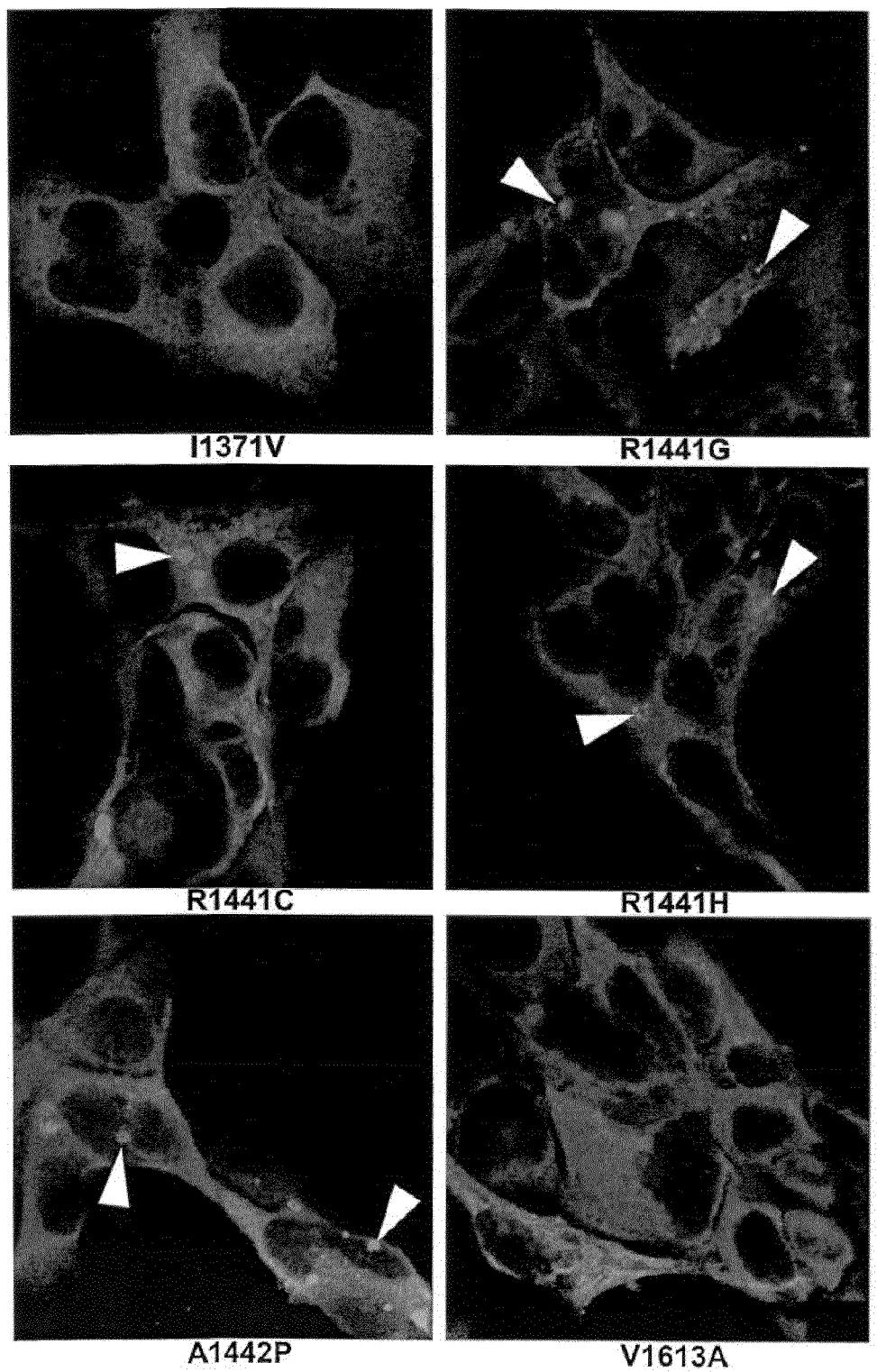
Figure 13:
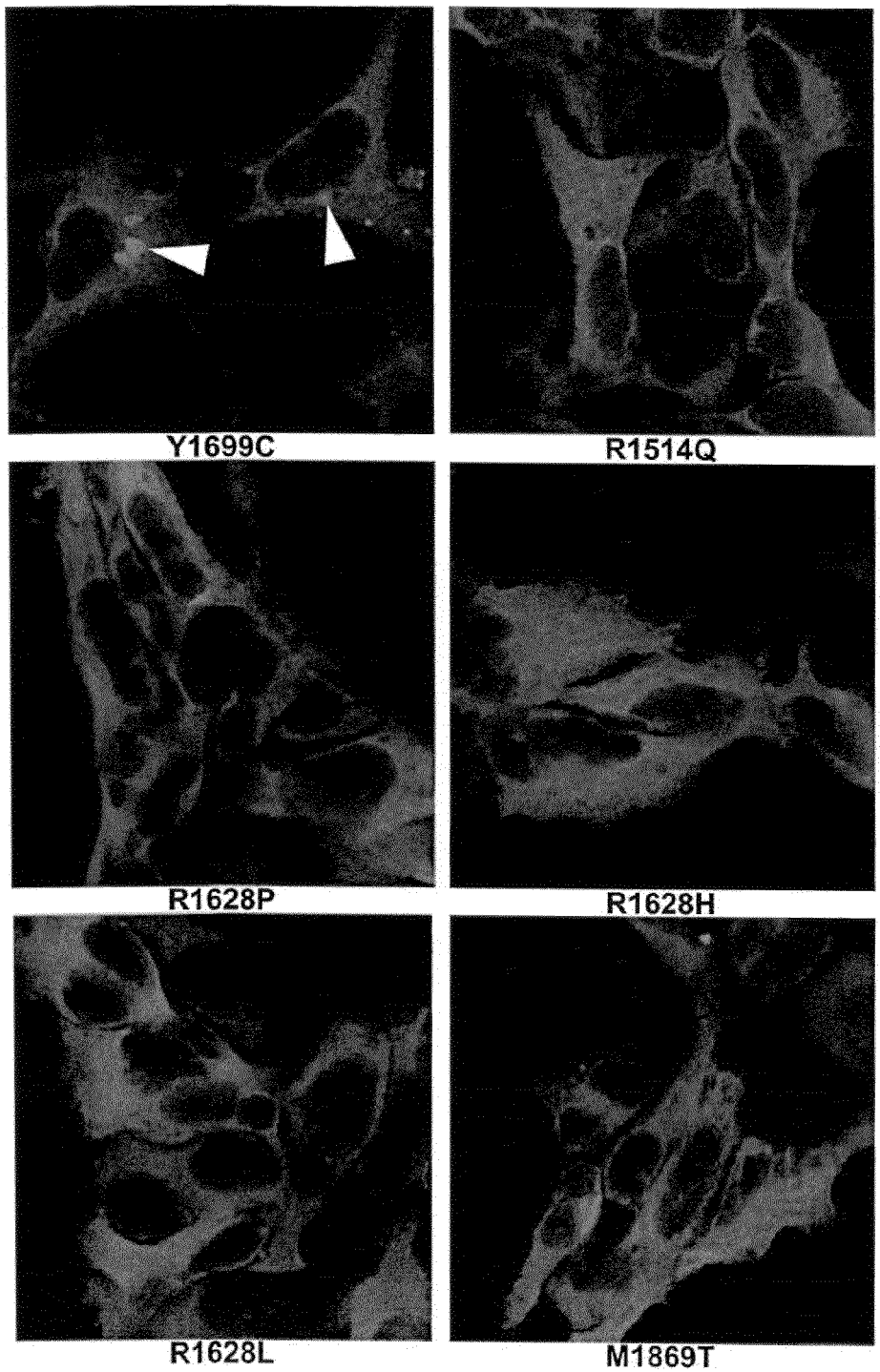
Figure 13:
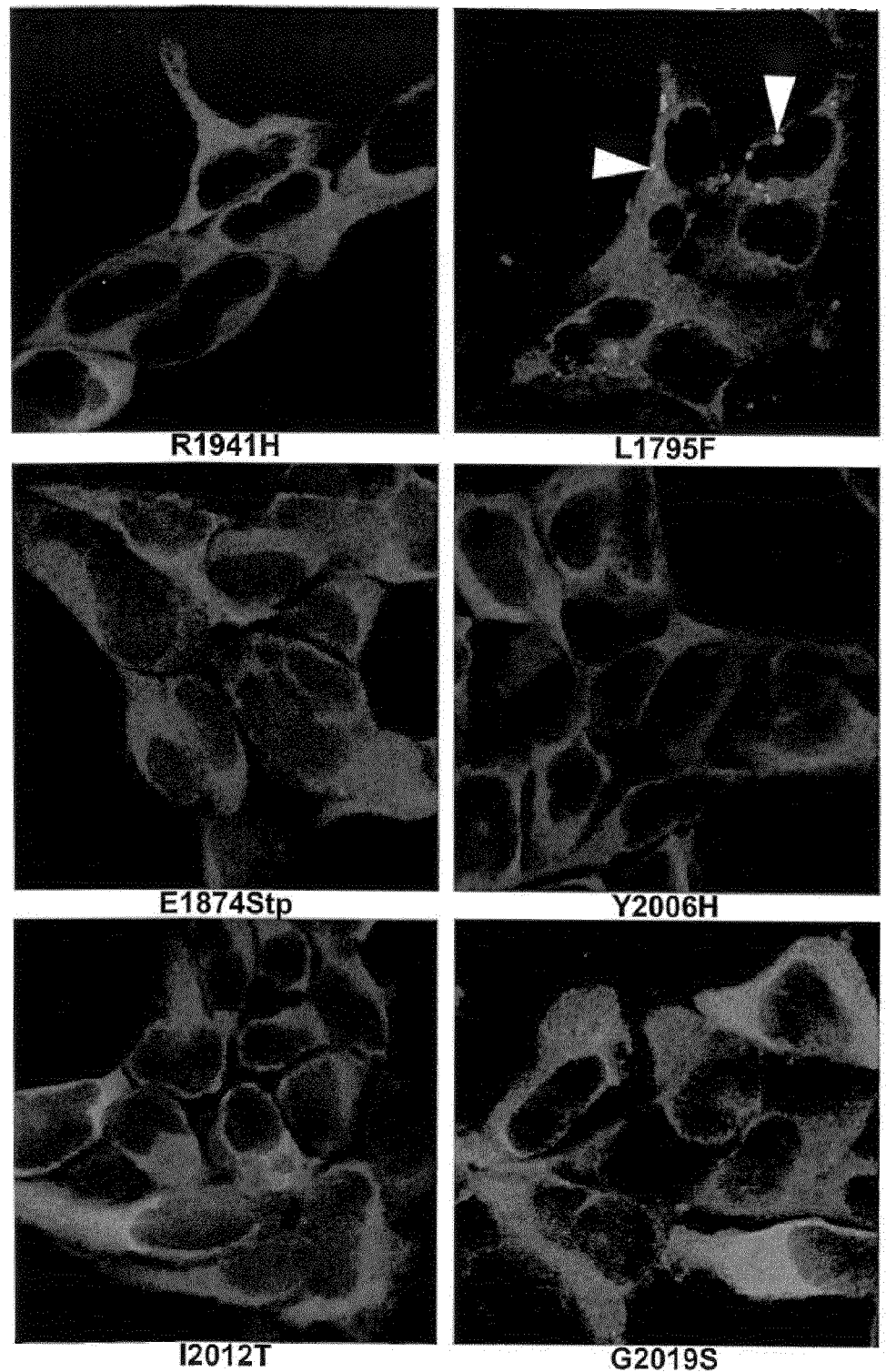
Figure 13:
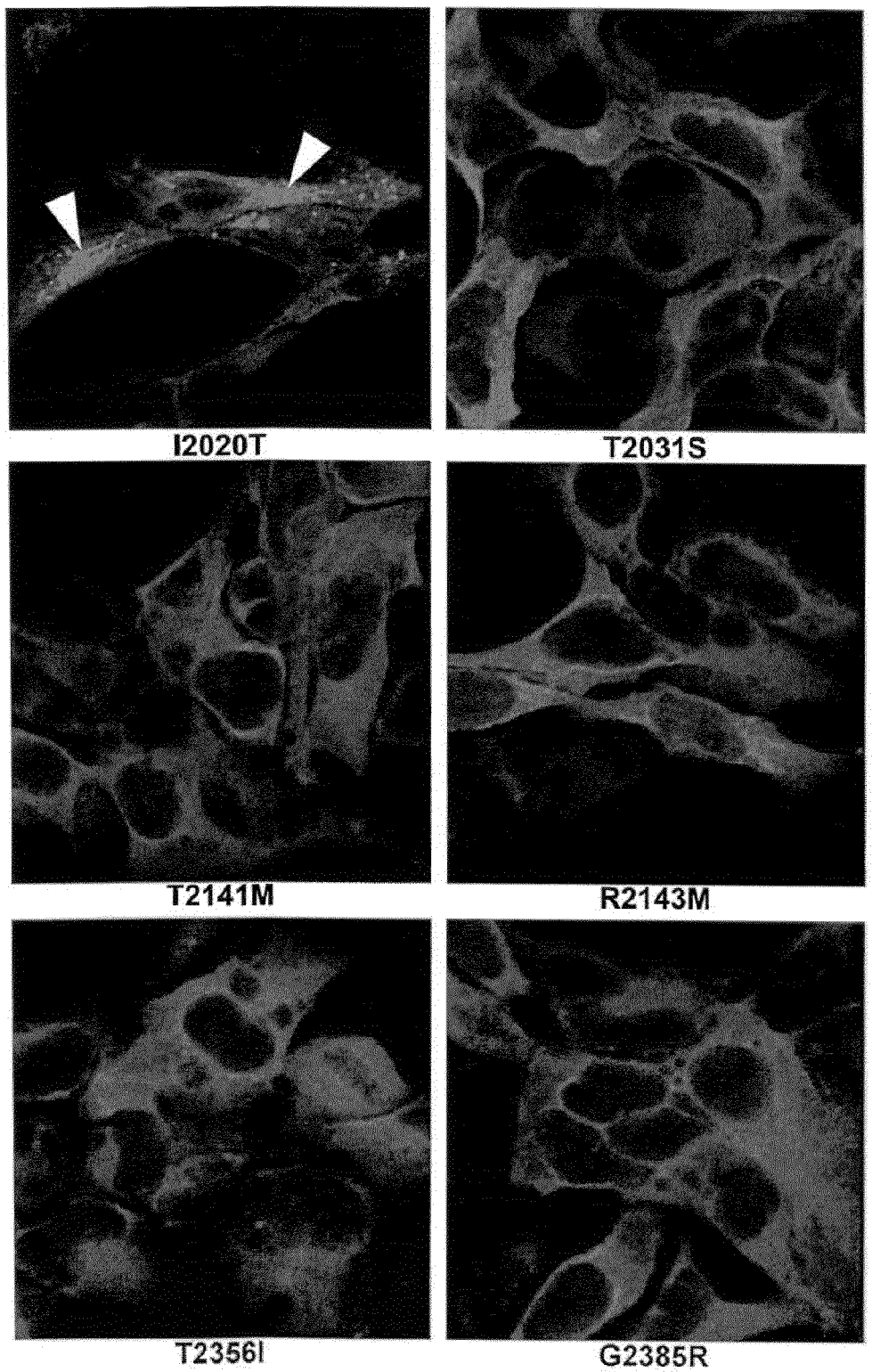

FIG. 13. Localization of 41 PD associated LRRK2 mutants. Same localisation data as presented in FIG. 11 except that larger panels of each of the micrographs is presented to improve clarity.

FIG. 14. Disruption of 14-3-3 binding induces accumulation of LRRK2 within cytoplasmic aggregates. A.) Stable-inducible T-REx cells lines harboring the indicated forms of LRRK2 were induced for 24 hours with 0.1 µg/ml doxycycline to induce expression of GFP-LRRK2. The indicated cell lines were treated in the absence or presence of the indicated dose of H-1152 for 90 min prior to fixation. Representative fluorescent micrographs of GFP-LRRK2 localisation are shown. Cytoplasmic aggregates of GFP-LRRK2 are indicated with white arrowheads. B.) Fluorescent micrographs representative of cultures of the indicated forms GFP-LRRK2 are shown. Cytoplasmic aggregates of GFP-LRRK2 are indicated with white arrowheads. Localisation analyses were performed in duplicate, and similar results observed in two independent experiments.

Figure 15:
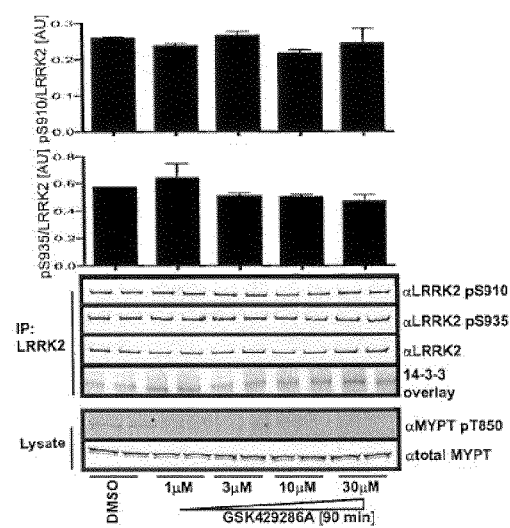

FIG. 15. Endogenous LRRK2 was immunoprecipitated with anti-LRRK2 100-500 (S348C) from Swiss 3T3 cells treated with DMSO vehicle control or the indicated concentrations of the potent ROCK inhibitor GSK429286A for 90 minutes. Immunoprecipitates were subjected to immunoblot analysis with the indicated antibody as well as 14-3-3 overlay far western analysis. Immunoblot analysis was quantified by Odyssey LICOR analysis and the amount of LRRK2 phosphorylation is presented as a ratio of phosphospecific antibody/total LICOR absorbance units (pS910/LRRK2 [AU]).

Figure 16:
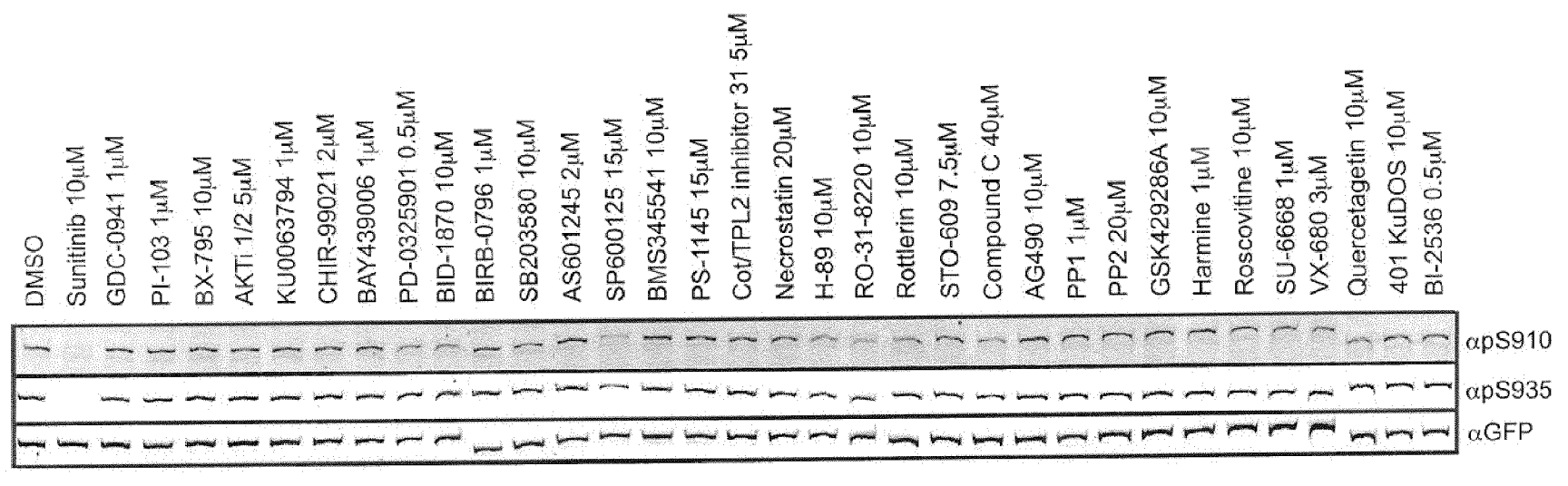

FIG. 16. HEK-293 stably expressing GFP-LRRK2 were treated with DMSO, or the following inhibitors dissolved in DMSO, at the indicated concentration for 90 minutes. Sunitinib (LRRK2 inhibitor [40]), GDC-0941 (PI3K inhibitor [41]), PI-103 (Dual mTOR/PI3K inhibitor [42]), BX-795 (Dual MARK/PDK1 inhibitor [43], AKTi1/2 (PKB inhibitor [44]), KU0063794 (mTOR inhibitor [45]), CHIR-99021 (GSK3 inhibitor [46]), BAY439006 (Raf inhibitor [47]), PD-0325901 (MEK1 inhibitor [48]), BID-1870 (RSK inhibitor [49]), BIRB-0796 (p38 MAPK inhibitor [50]), SB203580 (p38 MAPK inhibitor [51]), AS601245 (JNK inhibitor [52]), SP600125 (JNK inhibitor [53]), BMS345541 (IKK inhibitor [54]), PS-1145 (IKK inhibitor [55]), TPL2 inhibitor 31 (Cot/TPL2 inhibitor [56]), Necrostatin (RIPK inhibitor [57]), H-89 (Dual PKA/ROCK inhibitor [58]), RO-31-8220 (PKC inhibitor [59]), Rottlerin (PKC inhibitor [60]), STO-609 (CaMKK inhibitor [61]), Compound C (AMPK inhibitor [62]), AG490 (JAK inhibitor [63]), PP1 (Src inhibitor [64]), PP2 (Src inhibitor [65]), GSK429286A (ROCK inhibitor [40]), Harmine (Dual CDK/DYRK inhibitor [66]), Roscovitine (CDK inhibitor [67]), SU-6668 (Dual Src/Aurora kinase inhibitor [68]), VX-680 (Aurora kinase inhibitor [69]), Quercetagetin (PIMK inhibitor [70]), 401 KuDOS (DNAPK inhibitor [71]), BI-2536 (PLK1 inhibitor [72]). Following lysis 30 μg of lysate was resolved by SDS-PAGE and immunoblotted for LRRK2 phosphorylation at Ser910 and Ser935. Total LRRK2 was assessed by GFP immunoblot. The immunoblots shown are representative of 2 independent experiments.

EXAMPLE 1

Inhibition of Kinase Activity Leads to Dephosphorylation of LRRK2 at Ser910/Ser935 and Disruption of 14-3-3 Binding. Development of a Cell-Based Assay to Assess LRRK2 Inhibitors The Leucine Rich Repeat Protein Kinase-2 (LRRK2) is mutated in a significant number of Parkinson's disease patients. Since a common mutation changing Gly2019 to Ser enhances kinase catalytic activity, small molecule LRRK2 inhibitors might have utility in treating Parkinson's disease. However, the effectiveness of inhibitors is difficult to assess, as no physiological substrates or downstream effectors of LRRK2 have been identified that could be exploited to develop a robust cell-based assay. Here we demonstrate that endogenous LRRK2 interacts with endogenous 14-3-3 isoforms. This interaction is mediated by phosphorylation of conserved Ser910 and Ser935 residues located before the leucine rich repeat domain. Strikingly, treatment of Swiss 3T3 cells with two structurally unrelated inhibitors of LRRK2 (H-1152 or sunitinib), induced dephosphorylation of endogenous LRRK2 at Ser910 and Ser935, thereby disrupting 14-3-3 interaction. We suggest that H-1152 and sunitinib induce dephosphorylation of Ser910 and Ser935 by inhibiting LRRK2 kinase activity; these compounds failed to induce significant dephosphorylation of a drug resistant LRRK2 [A2016T] mutant. Moreover, consistent with the finding that non-14-3-3 binding mutants of LRRK2 accumulate within discrete cytoplasmic pools rather than diffusely localising throughout the cytoplasm, H-1152 causes LRRK2 to accumulate within cytoplasmic pools. These data indicate that dephosphorylation of Ser910, Ser935 or disruption of 14-3-3 binding and/or monitoring LRRK2 cytoplasmic localisation can be used as a marker to assess relative efficacy of LRRK2 kinase inhibitors in vivo. These findings will aid the development of LRRK2 kinase inhibitors. They will also stimulate further research to understand how phosphorylation of Ser910 and Ser935 is controlled by LRRK2 and establish any relationship to development of Parkinson's disease.

Materials and Methods

Reagents and General methods. Tissue-culture reagents were from Life Technologies. Glutathione Sepharose 4B was from Amersham Biosciences and [γ-$^{32}$P]-ATP was from Perkin Elmer. P81 phosphocellulose paper was from Whatman. Pepceuticals synthesized Nictide. The Flp-in T-REx system was from Invitrogen and stable cell lines, generated per manufacturer instructions by selection with hygromycin, have been described previously [8]. Restriction enzyme digests, DNA ligations and other recombinant DNA procedures were performed using standard protocols. All mutagenesis was carried out using the Quick-Change site-directed-mutagenesis kit (Stratagene). DNA constructs used for transfection were purified from *Escherichia coli* DH5α using Qiagen or Invitrogen plasmid Maxi kits according to the manufacturer's protocol. All DNA constructs were verified by DNA sequencing, which was performed by The Sequencing Service, School of Life Sciences, University of Dundee, Scotland, U.K., using DYEnamic ET terminator chemistry (Amersham Biosciences) on Applied Biosystems automated DNA sequencers. H1152 was purchased from Calbiochem and Sunitinib from LC Laboratories.

Buffers. Lysis Buffer contained 50 mM Tris/HCl, pH 7.5, 1 mM EGTA, 1 mM EDTA, 1% (w/v) 1 mM sodium orthovanadate, 10 mM sodium β-glycerophosphate, 50 mM NaF, 5 mM sodium pyrophosphate, 0.27 M sucrose, 1 mM Benzamidine and 2 mM phenylmethanesulphonylfluoride (PMSF) and was supplemented with either 1% (v/v) Triton X-100 or 0.5% (v/v) NP-40 with 150 mM NaCl as indicated. Buffer A contained 50 mM Tris/HCl, pH 7.5, 50 mM NaCl, 0.1 mM EGTA and 0.1% (v/v) 2-mercaptoethanol, and 0.27 M sucrose. Lambda phosphatase reactions were carried out in buffer A supplemented with 1 mM MNCl$_2$ and 2 mM DTT.

Cell culture, treatments and cell lysis. HEK-293 and Swiss 3T3 cells were cultured in Dulbecco's Modified Eagle's medium (DMEM) supplemented with 10% FBS, 2 mM glutamine and 1× antimycotic/antibiotic solution. T-REx cell lines were cultured in DMEM supplemented with 10% FBS and 2 mM glutamine, 1× antimycotic/antibiotic [pen/strep], and 15 μg/ml blastocidin and 100 μg/ml hygromycin. Cultures were induced to express the indicated protein by inclusion of 1 μg/ml doxycycline in the culture medium for the indicated times or 24 hours.

Cell transfections were performed by the polyethylenimine method [12]. Where inhibitors are utilized, they were dissolved in DMSO and used at the indicated concentrations with an equivalent volume of DMSO used as a control. The final concentration of DMSO in the culture medium was never more than 0.1% (v/v). Inhibitors were added to the culture medium for the indicated times before lysis. Per 15 cm dish, HEK 293 cells were lysed with 1.0 ml and 3T3 cells were lysed with 0.6 ml of lysis buffer supplemented with the indicated detergent and clarified by centrifugation at 16,000×g at 4° C. for 10 minutes. After induction and inhibitor treatment, T-REx-GFP expressing cells were lysed at room temperature with SDS lysis buffer after washing with PBS. SDS lysates were boiled and sonicated to reduce viscosity. When not used immediately, all lysate supernatants were snap frozen in liquid nitrogen and stored at −80° C. until use. Protein concentrations were determined using the Bradford method with BSA as the standard.

Antibodies. Anti-LRRK2 100-500 (S348C and S406C) and Anti-LRRK2 2498-2514 (S374C) were described previously [8]. Antibody against LRRK2 phosphoserine 910 (S357C) was generated by injection of the KLH conjugated phosphopeptide VKKKSNpSISVGEFY (where pS is phosphoserine) into sheep and was affinity purified by positive and negative selection against the phospho and de-phospho peptides respectively. Antibody against LRRK2 phosphoserine 935 (S814C) was generated by injection of the KLH conjugated phosphopeptide NLQRHSNpSLGPIFDH (where pS is phosphoserine) into sheep and was affinity purified by positive and negative selection against the phospho and de-phospho peptides respectively. Sheep polyclonal antibody S662B was raised against MBP-MYPT chicken amino acids (714-1004). Rabbit polyclonal antibody against MYPT phosphothreonine 850 was from Upstate (# 36-003). Anti GFP antibody (S268B) was raised against recombinant GFP protein and affinity purified against the antigen. Anti-FLAG M2 antibody and affinity matrix were from Sigma (A2220). Nanotrap GFP binder affinity matrix was from ChromoTek. Rabbit polyclonal antibody recognizing 14-3-3 (K-19, SC-629) and control rabbit IgG (SC-2027) antibody were from SantaCruz biotechnology. HSP90 antibody was from Cell signalling technology (#4877). Anti-MARK3 was from Upstate (#05-680).

Immunological procedures. Cell lysates (10-30 µg) were resolved by electrophoresis on SDS polyacrylamide gels or Novex 4-12% gradient gels, and electroblotted to nitrocellulose membranes. Membranes were blocked with 5% skimmed milk (w/v) in 50 mM Tris/HCl, pH 7.5, 0.15 M NaCl and 0.1% (v/v) Tween (TBST Buffer). For phospho-antibodies, primary antibody was used at a concentration of 1 µg/ml, diluted in 5% skimmed milk in TBST with the inclusion of 10 µg/ml dephosphorylated-peptide. All other antibodies were used at 1 µg/ml in 5% (w/v) milk in TBST. Detection of immune-complexes was performed using either fluorophore conjugated secondary antibodies (Molecular Probes) followed by visualisation using an Odyssey LICOR or by horseradish-peroxidase-conjugated secondary antibodies (Pierce) and an enhanced-chemiluminescence reagent. For immunoprecipitations, antibody was non-covalently coupled to protein G-Sepharose at a ratio of 1 µg antibody/µl of beads, or anti-FLAG M2-agarose was utilized. Cell lysate was incubated with coupled antibody for 1 hour. Immune complexes were washed twice with lysis buffer supplemented with 0.3 M NaCl and twice with Buffer A. Precipitates were either used as a source of kinase or immediately analyzed by immunoblot. Digoxigenen (DIG) labelled 14-3-3 for use in overlay far western analysis was prepared as described in [13]. To directly assess 14-3-3 interaction with LRRK2, immunoprecipitates were electroblotted to nitrocellulose membranes and blocked with 5% skimmed milk for 30 minutes. After washing with TBST, membranes were incubated with DIG labelled 14-3-3 diluted to 1 µg/ml in 5% BSA in TBST overnight at 4° C. DIG 14-3-3 was detected with HRP labelled anti-DIG Fab fragments (Roche).

SILAC media. SILAC DMEM (high glucose without $NaHCO_3$, L-glutamine, arginine, lysine and methionine Biosera #A0347) was prepared with 10% dialyzed FBS (Hyclone) and supplemented with methionine, glutamine, $NaHCO_3$, labeled or unlabeled arginine and lysine. Cells harboring GFP tagged proteins were cultured in SILAC DMEM for three passages at a 1:10 ratio with the following isotopic labeling. For GFP versus wild type LRRK2, L-arginine (84 µg/ml; Sigma-Aldrich) and L-lysine (146 µg/ml lysine; Sigma-Aldrich) were added to the GFP "light" media, while L-arginine $^{13}C$ and L-lysine $^{13}C$ (Cambridge Isotope Laboratory) were added to the GFP-LRRK2 wild type "heavy" media at the same concentrations. For GFP versus LRRK2 G2019S experiments, L-arginine and L-lysine were added to the GFP "light" media and L-arginine $^{13}C/^{15}N$ and L-lysine $^{13}C/^{15}N$ (Cambridge Isotope Laboratory) to the GFP-LRRK2 G2019S "heavy" media. The amino acid concentrations are based on the formula for normal DMEM (Invitrogen). Once prepared, the SILAC media was mixed well, filtered through a 0.22-µm filter (Millipore). Metabolically labeled cells were induced to express GFP or the GFP-LRRK2 fusion protein for 24 hours by inclusion of doxycycline in the culture media.

SILAC Mass spectrometry. Cells metabolically labeled and induced to express either GFP or LRRK2-wild type or G2019S were lysed in lysis buffer supplemented with 1% Triton X-100 at 0.5 ml per 10 cm dish. For each condition individually, 9 mg of cell lysate was subjected to individual immunoprecipitation with a 20 µl bed volume of GFP binder agarose beads for 1 hour at 4° C. Beads were washed once with 5 ml and then with 10 ml of lysis buffer supplemented with 1% Triton-X 100 and 300 mM NaCl. Beads were then washed once with 5 ml and then once with 10 ml storage buffer. Bead associated proteins were eluted with 1×LDS sample buffer for 10 min at 70° C. then passed through a 0.22 µm spin-X column. Control GFP eluates were combined with either eluates of wild type LRRK2 or LRRK2 G2019S in equal amounts and reduced and alkylated as above. Samples were resolved on a 12% Novex gel for only one half of the gel. Gels were stained with colloidal blue overnight and destained for 3 hours. The entire lane was excised in 9 total bands and digested with trypsin as described previously [30].

Mass spectrometry analysis of peptides. The digests were separated on a Biosphere $C_{18}$ trap column (0.1 mm id×2 mm, Nanoseparations, Holland) connected to a PepMap C18 nano column (75 µm×15 cm, Dionex Corporation) fitted to a Proxeon Easy-LC nanoflow LC-system (Proxeon, Denmark) with solvent A (2% acetonitrile/0.1% formic acid/98% water) and solvent B (90% acetonitrile/10% water/0.09% formic acid). 10 µl of sample (a total of 2 µg of protein) was loaded with a constant flow of 7 µl/min onto the trap column in solvent A and washed for 3 min at the same flow rate. After trap enrichment, peptides were eluted with a linear gradient of 5-50% solvent B over 90 min with a constant flow of 300 nl/min. The HPLC system was coupled to a linear ion trap-orbitrap hybrid mass spectrometer (LTQ-Orbitrap XL, Thermo Fisher Scientific Inc) via a nanoelectrospray ion source (Proxeon Biosystems) fitted with a 5 cm Picotip FS360-20-10 emitter. The spray voltage was set to 1.2 kV and the temperature of the heated capillary was set to 200° C. Full scan MS survey spectra (m/z 350-1800) in profile mode were acquired in the Orbitrap with a resolution of 60,000 after accumulation of 500,000 ions. The five most intense peptide ions from the preview scan in the Orbitrap were fragmented by collision-induced dissociation (normalized collision energy 35%, activation Q 0.250 and activation time 30 ms) in the LTQ after the accumulation of 10,000 ions. Maximal filling times were 1,000 ms for the full scans and 150 ms for the MS/MS scans. Precursor ion charge state screening was enabled and all unassigned charge states as well as singly charged species were rejected. The lock mass option was enabled for survey scans to improve mass accuracy. Data were acquired using the Xcalibur software.

Mass Spectrometry Data MaxQuant Analysis. The raw mass spectrometric data files obtained for each experiment was collated into a single quantitated dataset using MaxQuant (version 1.0.13.13) (http://www.maxquant.org) and the Mascot search engine (Matrix Science, version 2.2.2) software. Enzyme specificity was set to that of trypsin, allowing for cleavage N-terminal to proline residues and between aspartic acid and proline residues. Other parameters used within the software: Variable modifications—Methionine Oxidation; Database—target-decoy human MaxQuant (ipi.HUMAN.v3.52.decoy) (containing 148,380 database entries); Labels—R6K4 [for GFP versus wild type LRRK2] or R10K8 [for GFP versus LRRK2 G20195]; MS/MS tolerance—0.5 Da; (e) Top MS/MS peaks per 100 Da—5; Maximum missed cleavages—2; Maximum of labeled amino-acids: 3; False Discovery Rate (FDR): 1%.

LRRK2 Immunoprecipitation Kinase assays. Peptide Kinase Assays were set up in a total volume of 50 µl with immunoprecipitated LRRK2 as a source of kinase, in 50 mM Tris pH 7.5, 0.1 mM EGTA, 10 mM $MgCl_2$ and 0.1 mM [γ-$^{32}$P]ATP (~500-1000 cpm/pmol) in the presence of 30 µM Nictide peptide substrate. Reactions were terminated by applying 30 µl of the reaction mixture on to P81 phosphocellulose paper and immersion in 50 mM phosphoric acid. After extensive washing, reaction products were quantitated by Cerenkov counting. One half of the remaining reaction was subjected to immunoblot analysis using the Odyssey LICOR system and specific activity is represented as cpm/LICOR independent density values.

500 μg of transfected cell lysates was subjected to immunoprecipitation with 5 μl bed volume of anti-FLAG agarose for 1 hr. Beads were washed twice with Lysis Buffer supplemented with 300 mM NaCl, the twice with Buffer A. Peptide Kinase Assays were set up in a total volume of 50 μl with immunoprecipitated LRRK2 in 50 mM Tris pH 7.5, 0.1 mM EGTA, 10 mM $MgCl_2$ and 0.1 mM [$\lambda$-$^{32}$P]ATP (~300-500 cpm/pmol) in the presence of 200 μM long variant of the LRRKtide peptide substrate (RLGRDKYKTLRQIRQGNT-KQR) [9, 10] or the Nictide peptide substrate (RLGWWR-FTLRRARQGNTKQR) [10]. Reactions were terminated by applying 30 μl of the reaction mixture on to P81 phosphocellulose paper and immersion in 50 mM phosphoric acid. After extensive washing, reaction products were quantitated by Cerenkov counting. One half of the remaining reaction was subjected to immunoblot analysis using the Odyssey LICOR system and specific activity is represented as cpm/LICOR independent density values Phosphorylation site identification by mass spectrometry. Endogenous and recombinant LRRK2 was immunoprecipitated from 50 mg of Swiss 3T3 lysate or T-Rex cells induced to express FLAG-LRRK2 cell lysate using anti-LRRK2 (100-500) or anti-FLAG agarose, respectively. Immunoprecipitates were eluted from the affinity matrices using 2×LDS sample buffer or 200 μg/ml FLAG peptide then filtered through a 0.2 μm Spin-X column (Corning) before reduction with 10 mM dithiothreitol and alkylation with 50 mM iodoacetamide. Samples were heated for 10 min at 70° C. and resolved on 4-12% Novex gels before staining with colloidal blue (Invitrogen). Bands corresponding to LRRK2 were excised and digested with trypsin as described previously [30]. Samples were analyzed on an LTQ Orbitrap XL mass spectrometer (Thermo) as described above, except the top 5 ions were fragmented in the linear ion trap using multistage activation of the neutral loss of phosphoric acid from the parent ion (neutral loss masses=49, 32.33 and 24.5 for z=2, 3 and 4). Mascot generic files were created from the raw files using raw2 msm (gift from M. Mann) and were searched on a local Mascot server (matrixscience.com) using the International Protein Index (IPI) mouse database for endogenous LRRK2 or the IPI human database for recombinant LRRK2.

Fluorescence Microscopy. HEK-293 Flp-in T-REx were purchased from Invitrogen and stable cells harbouring GFP tagged wild type and mutant forms of LRRK2 were generated using standard protocols. Cells were plated in 4-well glass bottom, CC2 coated chamber slides (Nunc). One day after plating, cells were induced with 0.1 μg/ml doxycycline and 24 hr later, cells were fixed in 4% paraformaldehyde buffered in phosphate buffered saline (purchased from USB, # 19943). Cells were mounted in ProLong Gold (Invitrogen) and imaged under the same settings for each mutant, on a Zeiss LSM 700 confocal microscope using an a Plan-Apochromat ×100 objective.

Results

Association of LRRK2 with 14-3-3. We employed quantitative Stable Isotope Labelling with Amino acids in Cell culture (SILAC)-based mass spectrometry to identify proteins associated with immunoprecipitates of stably expressed full length GFP-LRRK2 (FIGS. 1A & 1B) as well as the GFP-LRRK2[G2019S] mutant (FIGS. 1C & 1D) derived from HEK-293 cells. The top hit, that was enriched at 10 to 30-fold higher levels with GFP-LRRK2 or GFP-LRRK2 [G2019S] compared to GFP alone, comprised beta, eta, theta, zeta and epsilon isoforms of 14-3-3 for wild type LRRK2 (FIG. 1B) and beta, theta, zeta, gamma and epsilon isoforms for LRRK2 [G2019S] (FIG. 1D). The two other major interactors that were observed comprised two isoforms of the heat shock protein-90 (Hsp90) chaperone-associated with their kinase-specific targeting CDC37 subunit (enriched 5 to 15-fold). Hsp90 and CDC37 associated with both wild type LRRK2 as well as LRRK2[G2019S] mutant and have previously been reported to interact with LRRK2 [14]. No other significant interactors of LRRK2 were observed in our interactor screens.

Figure 2:
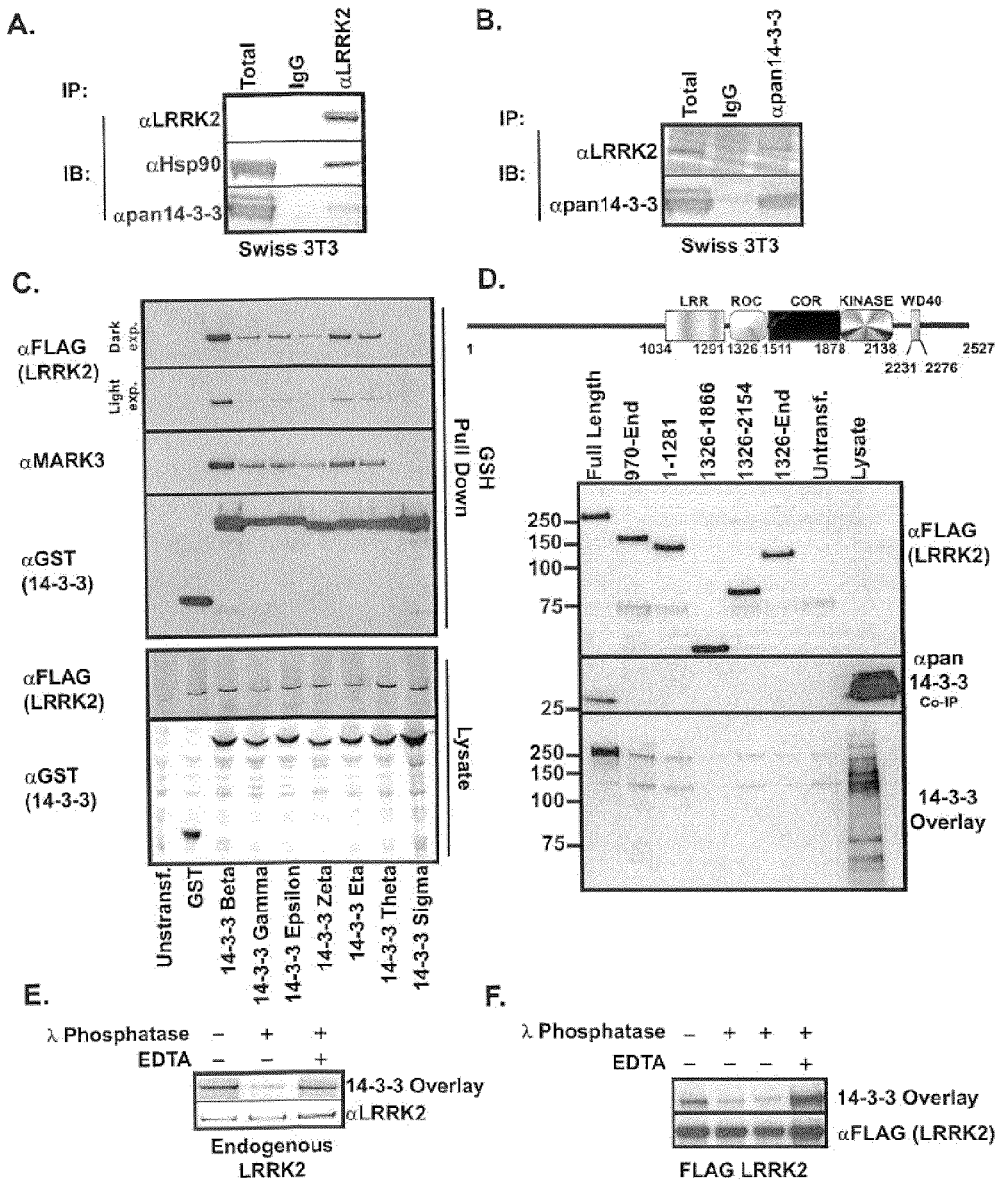
FIG. 2. Characterisation of LRRK2 interaction with 14-3-3. A.) 5 mg of Swiss 3T3 lysate was subjected to immunoprecipitation with control IgG or anti-LRRK2 (S348C) antibody. Immunoprecipitates were resolved on 4-12% Novex SDS-polyacrylamide gel and immunoblotted with antibodies against LRRK2 (S374C), Hsp90 and pan 14-3-3. B.) 5 mg of Swiss 3T3 lysate was subjected to immunoprecipitation with anti-pan 14-3-3 antibodies and immunoprecipitates were resolved on 4-12% Novex SDS-polyacrylamide gels and immunoblotted with antibodies against pan-14-3-3 and LRRK2 (S374C). C.) Lysates of T-Rex HEK 293 FLAG-LRRK2 cells transfected with pEBG plasmids encoding GST or GST tagged 14-3-3 isoforms and induced to express LRRK2 by inclusion of 1 μg/ml of doxycycline in the culture medium. 36 hours post transfection cells were lysed and glutathione-Sepharose affinity purified proteins immunoblotted with anti-GST or anti-FLAG antibodies. D.) Fragments encoding the indicated domains of LRRK2 were transiently expressed in HEK-293 cells and immunoprecipitated with anti-FLAG antibodies. The immunoprecipitates were resolved on 4-12% Novex SDS-polyacrylamide gels and probed with either anti-FLAG antibodies or 14-3-3 overlay with digoxigenin labeled 14-3-3 in a far western assay. Co-immunoprecipitated 14-3-3 was detected with anti-pan 14-3-3 antibody. E.) Endogenous LRRK2 was immunoprecipitated from Swiss 3T3 cells with anti-LRRK2 (S348C) and subsequently treated with λ-phosphatase in the absence or presence of EDTA prior to immunoblot analysis with indicated antibodies or a 14-3-3 overlay assay. F.) As in E, except experiment undertaken with immunoprecipitated FLAG-LRRK2 obtained following transient transfection in HEK-293 cells.

We found that endogenous 14-3-3 as well as Hsp90 was co-immunoprecipitated with endogenous LRRK2 from Swiss 3T3 cells (FIG. 2A). We also observed that endogenous LRRK2 was co-immunoprecipitated with an antibody that recognises endogenous 14-3-3 isoforms from Swiss 3T3 cells (FIG. 2B). Plasmids encoding for the expression of all seven isoforms of human 14-3-3 were transfected into previously generated HEK-293 cells stably expressing full length FLAG-LRRK2 [8]. Following affinity purification, apart from atypical sigma isoform, all other forms of 14-3-3 interacted with FLAG-LRRK2 (FIG. 1C). We also observed that whilst full length LRRK2 associated with endogenous 14-3-3 in 293 cells, in parallel experiments, various isolated domains of LRRK2 tested, failed to bind 14-3-3 (FIG. 1D). This observation was confirmed employing a 14-3-3 overlay-far western binding assay, where full length LRRK2, but not isolated domains bound to digoxoxigenin-labelled 14-3-3 (FIG. 1D—lower panel).

14-3-3 isoforms mostly interact with specific phosphorylated residues on their binding partners [11, 15]. To verify whether association of 14-3-3 with LRRK2 was dependent upon phosphorylation, we incubated endogenous LRRK2 (FIG. 2E) or overexpressed FLAG-LRRK2 (FIG. 2F) in the presence or absence of lambda phosphatase. Treatment of endogenous or overexpressed LRRK2 with lambda phosphatase markedly reduced interaction of 14-3-3 assessed using the overlay assay. Inclusion of EDTA in the assay, which inhibits the lambda phosphatase, prevented lambda phosphatase from suppressing 14-3-3 binding to LRRK2 (FIGS. 2E & 2F). Residual binding of 14-3-3 to LRRk2 following lambda phosphatase treatment is presumably due to incomplete dephosphorylation of LRRK2.

Mapping of major phosphorylation sites on endogenous LRRK2. To determine which phosphorylated residue(s) mediate binding to 14-3-3, we performed detailed phosphopeptide orbitrap mass spectrometry analysis of endogenous LRRK2 immunoprecipitated from mouse Swiss 3T3 cells (FIG. 3A). This revealed three clear phosphorylation sites namely Ser860, Ser910 and Ser935 (FIG. 3B). These residues lie in the N-terminal non-catalytic region of LRRK2 just prior to the leucine rich repeats (FIG. 3C). We also analysed phosphorylation of overexpressed full length human FLAG-LRRK2 expressed in HEK-293 cells, which confirmed that Ser860, Ser910 and Ser935 were major sites of phosphorylation (FIGS. 3A & 3B). In addition, we found three other phosphorylation sites in the overexpressed human FLAG-LRRK2 preparation namely Ser955, Ser973 and Ser976 (FIGS. 3B & 3C). The phospho-peptides encompassing Ser955, Ser973 and Ser976 were also detected in our analysis of endogenous LRRK2 but due to the lower abundance of these peptides we were unable to assign the exact phosphorylation sites (data not shown).

Phosphorylation of Ser910 and Ser935 mediates 14-3-3 binding, but does not control kinase activity. We observed that mutation to Ala of Ser860, Ser955, Ser973, Ser976 or both Ser973+976 phosphorylation sites, did not affect binding of 14-3-3 to full length FLAG-LRRK2 (FIG. 3D). Strikingly however, mutation of Ser910 and/or Ser935 to Ala, ablated interaction, indicating that phosphorylation of these residues mediates binding of LRRK2 to 14-3-3 isoforms (FIG. 3D). Mutations of the identified phosphorylation sites did not affect protein kinase activity of LRRK2 as measured against the Nictide substrate peptide (FIG. 3D).

We next generated phosphospecific antibodies recognising LRRK2 phosphorylated at Ser910 or Ser935. These antibodies were specific, as mutation of Ser910 to Ala ablated recognition of LRRK2 with phospho-Ser910 antibody and similarly, mutation of Ser935 abolished recognition with the phospho-Ser935 antibody (FIG. 3E). We consistently observed that mutation of Ser910 to Ala reduced phosphorylation of Ser935 about two-fold and vice versa mutation of Ser935 reduced phosphorylation of Ser910 around two-fold as quantitated by LICOR (FIG. 3E). Utilising these antibodies, we demonstrate that endogenous LRRK2 immunoprecipitated from mouse brain, kidney and spleen was phosphorylated at Ser910 as well as Ser935 and also bound 14-3-3 (FIG. 3F).

Figure 3:
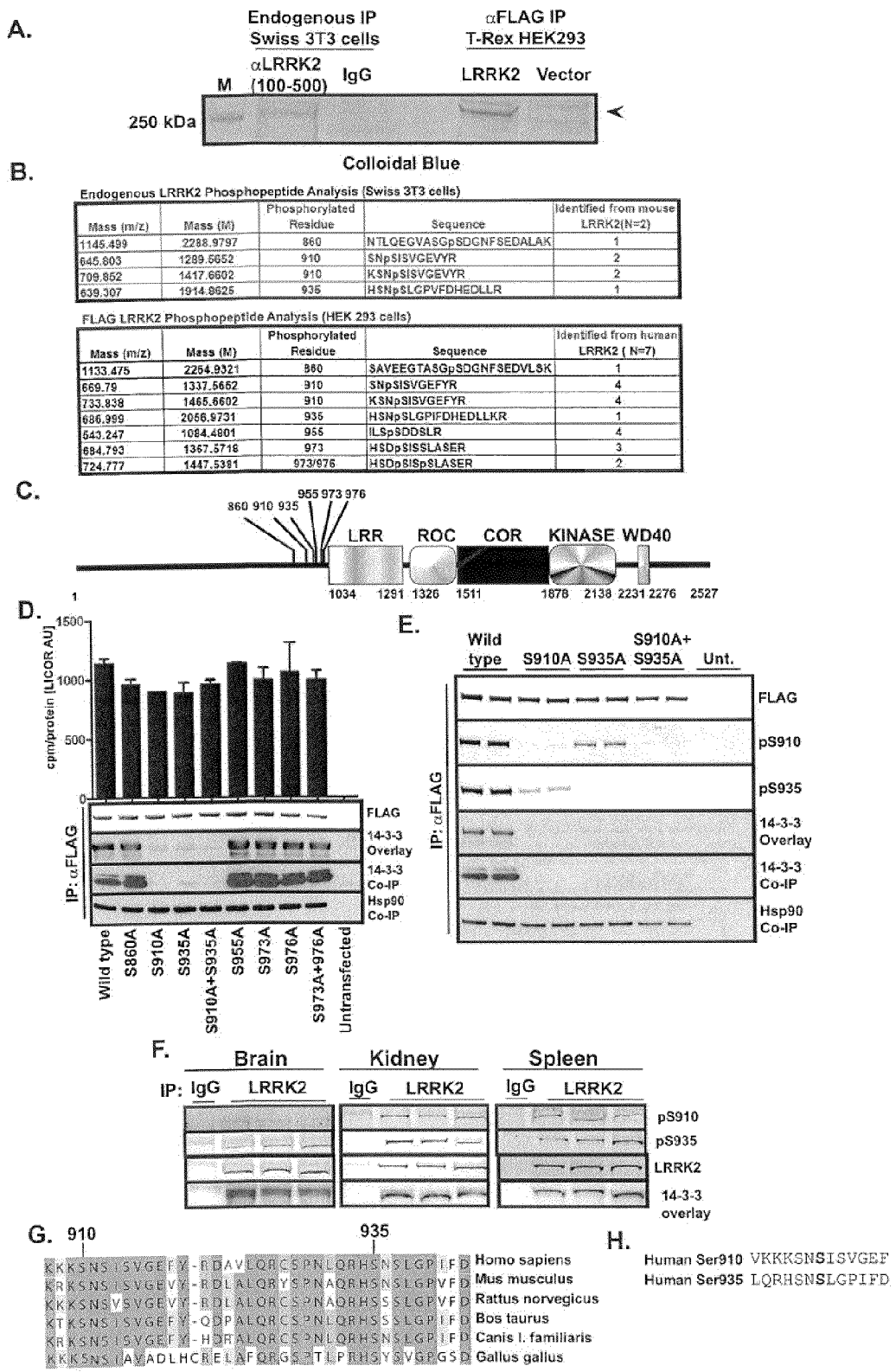
FIG. 3. Identification of LRRK2 phosphorylation sites, the sites of 14-3-3 binding and characterization of anti-pS910 and anti-pS935. A.) Endogenous LRRK2 was immunoprecipitated with anti-LRRK2 100-500 (S348C) from Swiss 3T3 cells and FLAG-LRRK2 was immunoprecipitated with anti-FLAG agarose from stable, inducible T-Rex HEK 293 cells and was resolved on a 4-12% Novex SDS-polyacrylamide gel and stained with colloidal blue. Gel is representative of several experiments. LRRK2 tryptic peptides were subjected to LC-MSMS on an LTQ-Orbitrap mass spectrometer. B.) Phosphopeptides identified by LTQ-Orbitrap mass spectrometry shown in tabular format. Observed mass (m/z) and predicted mass (M) are shown, along with the site of phosphorylation and peptide sequence identified. The number of experiments evaluated (N) is indicated at the top of the column and the number of times, in total, the phosphorylated peptide was identified is indicated. C.) Domain structure of LRRK2 is presented to scale, with amino acid residues indicating domain boundaries indicated. Position of identified phosphorylation sites is shown. D.) The indicated phosphorylation sites identified in A and B were mutated to Ala and transiently expressed in HEK-293 cells. LRRK2 was immunoprecipitated with FLAG agarose and equal amounts of each protein were probed with FLAG (total) and ability to directly bind 14-3-3 was assessed in an overlay assay. 14-3-3 and Hsp90 co-immunoprecipitation (Co-IP) was determined by immunoblotting the immunoprecipitates with pan-14-3-3 and Hsp90 antibodies. Kinase activity was assayed against 30 μM Nictide and specific activity was determined by correcting incorporation of phosphate for protein levels in the immunoprecipitate by quantitative immunoblot using Odyssey LICOR and is presented as counts per minute/LICOR absorbance units (cpm/LICOR AU). Data are mean±SEM and were performed in duplicate and are representative of at least 4 separate experiments. E.) The indicated forms of LRRK2 were expressed in 293 cells by transient transfection. 36 hours post transfection these were immunoprecipitated with Flag antibody and immunoblotted with phosphospecific antibodies against S910 (S357C) and S935 (S814C). Direct binding of immunoprecipitates to 14-3-3 was assessed by overlay assay and co-immunoprecipitation of 14-3-3 and Hsp90 assessed by immunoblotting with the respective antibodies. F.) LRRK2 was immunoprecipitated from tissues of wild type male C57BL/6 mice and immunoblotted for Ser910 and Ser 935 phosphorylation and 14-3-3 binding was assessed by overlay assay as in E. G.) Multiple sequence alignment of LRRK2 from *Homo sapiens* (NP_940980), *Mus musculus* (NP_080006), *Rattus norvegicus* (XP_235581), *Bos Taurus* (XP_615760), *Canis lupis familiaris* (XP_543734), and *Gallus gallus* (XP_427077). Position of the phosphorylated residues Serine 910 and 935 are indicated. Identical residues are indicated. H.) Sequence comparison of residues surrounding the Ser910 and Ser935 phosphorylation sites of human LRRK2.1.) Multiple sequence alignment of LRRK2 from *Homo sapiens* (NP_940980), *Pan troglodytes* (XP_001168494), *Mus musculus* (NP_080006), *Rattus norvegicus* (XP_235581), *Bos Taurus* (XP_615760), *Canis lupis familiaris* (XP_543734), and *Gallus gallus* (XP_427077). Position of the phosphorylated residues Serine 910 and 935 are indicated. Identical residues are indicated.

Sequence alignments indicate that the Ser910 and Ser935 sites as well as residues surrounding them are highly conserved in mammalian species (FIG. 3G). This region encompassing Ser910 and Ser935 is not present in *Caenorhabditis elegans* or *Drosophila melanogaster* LRK-1, or indeed mammalian LRRK1. Comparison of the residues surrounding Ser910 and Ser935 indicates some striking similarities (FIG. 3 H i.e. basic residues −3 and −4 positions, Ser residue at the −2 position, Asn at the −1 position and a large hydrophobic residue at the +1 position).

Figure 4:
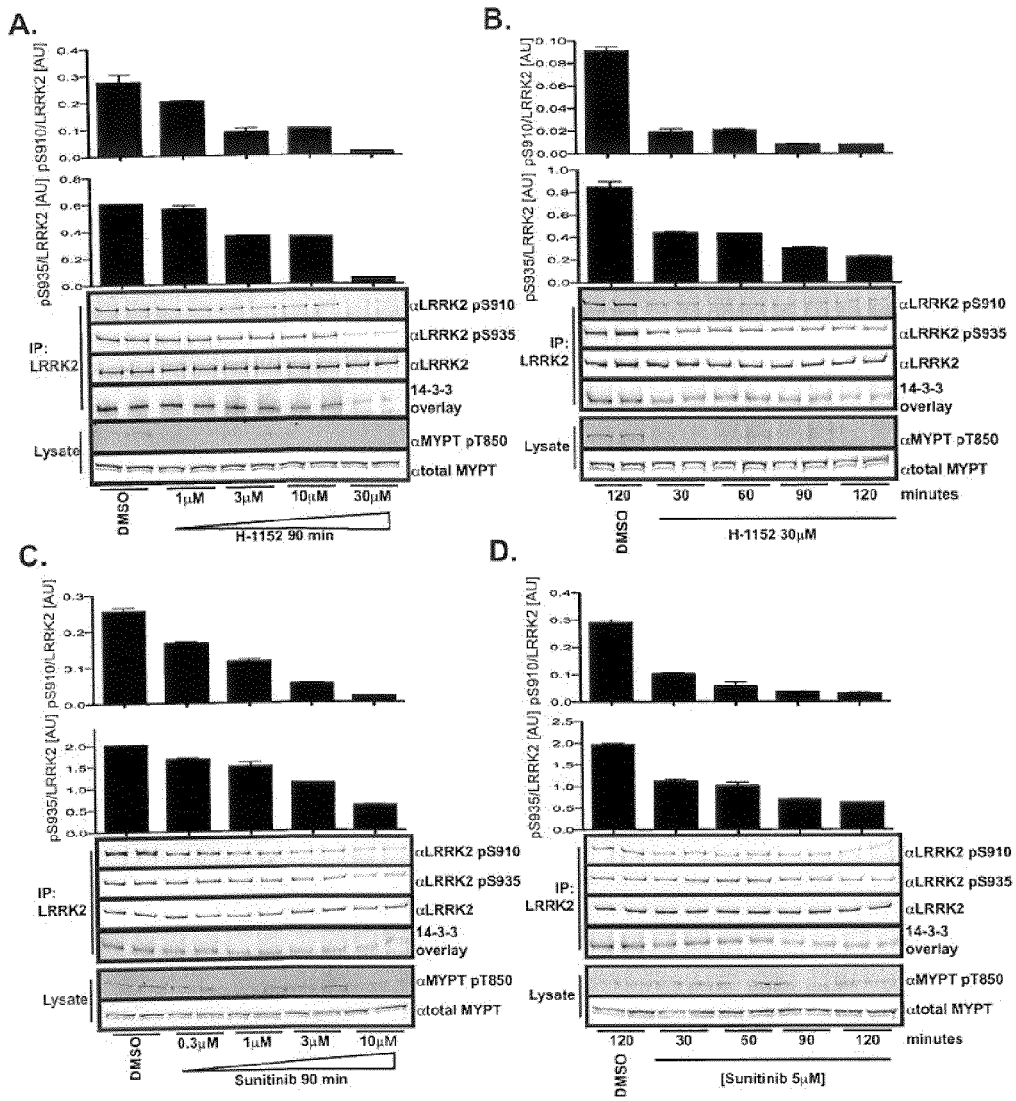
FIG. 4. H-1152 and sunitinib treatment leads to dephosphorylation of S910 and 935 and disruption of 14-3-3 interaction. A.) Endogenous LRRK2 was immunoprecipitated with anti-LRRK2 100-500 (S348C) from Swiss 3T3 cells were treated with DMSO vehicle control or the indicated concentrations of H-1152 for 90 minutes. Immunoprecipitates were resolved on 4-12% Novex gels and subjected to 14-3-3 overlay far western analysis and immunoblotted with anti-pS910 (S357C), anti-pS935 (S814C) and anti-LRRK2 (S374C) antibodies. Immunoblots were quantitated by Odyssey LICOR and the amount of LRRK2 phosphorylation is presented as a ratio of phosphospecific antibody/total LICOR absorbance units (pS910/LRRK2 [AU]). B.) Endogenous LRRK2 immunoprecipitates were analyzed as in A, except that cells were treated with H-1152 at 30 μM for the indicated time prior to cell lysis. C.) and D.) as in A. and B. respectively, except that sunitinib was employed rather than H1152. Data are mean±SEM and were performed in duplicate and are representative of at least 2 separate experiments.

LRRK2 inhibitors induced dephosphorylation of Ser910/935 and disrupted 14-3-3 binding. Incubation of Swiss 3T3 cells with increasing amounts of the LRRK2 inhibitors H-1152 (FIG. 4A) or sunitinib (FIG. 4C) resulted in a dose dependent dephosphorylation of endogenous LRRK2 at Ser910 and Ser935 which was accompanied by a concomitant reduction in 14-3-3 binding. 10-30 µM H-1152 or 3-10 µM sunitinib induced almost complete dephosphorylation of Ser910 and Ser935 resulting in a loss of 14-3-3 binding. The inhibitory effects of H-1152 (FIG. 4B) and sunitinib (FIG. 4D) on endogenous LRRK2-Ser910/Ser935 phosphorylation and 14-3-3 binding were observed within 30 min and sustained for at least 2 hours.

Evidence that LRRK2 kinase activity controls Ser910 and Ser935 phosphorylation as well as 14-3-3 binding. To determine whether the effect of H1152 and sunitinib on LRRK2 phosphorylation and 14-3-3 binding resulted from inhibition of LRRK2 protein kinase activity, we treated HEK-293 overexpressing LRRK2[G2019S] or the H1152/Sunitinib resistant LRRK2[A2016T+G2019S] mutant with LRRK2 inhibitors. As observed with the endogenous LRRK2, we found that H-1152 and sunitinib induced a dose-dependent dephosphorylation of the Parkinson's disease LRRK2[G2019S] mutant at Ser910 and Ser935 as well as disrupting binding to 14-3-3 (FIG. 5A—upper panel). Crucially however, neither H-1152 nor sunitinib significantly inhibited Ser910 or Ser935 phosphorylation or 14-3-3 binding to drug resistant LRRK2 [A2016T+G2019S] mutant (FIG. 5A—lower panel). This strongly suggests that the ability of H1152 and sunitinib to induce dephosphorylation of Ser910 as well as Ser935 and hence disrupt 14-3-3 binding is dependent upon the ability of these compounds to inhibit LRRK2 protein kinase activity.

In agreement with the pharmacological data demonstrating that H-1152 and sunitinib inhibit mutant LRRK2[G2019S] 2 to 4-fold more potently than wild type LRRK2 [8], we found that H1152 and sunitinib were more potent in inducing dephosphorylation and impairing binding to 14-3-3 to LRRK2[G2019S] than wild type LRRK2 (compare FIG. 5A & FIG. 5B—upper panels). The potency of H-1152 and sunitinib at inducing dephosphorylation of wild type FLAG-LRRK2 in 293 cells was similar to the effects of these drugs observed for endogenous LRRK2 in Swiss 3T3 cells (compare FIGS. 4 and 5B).

Figure 6:
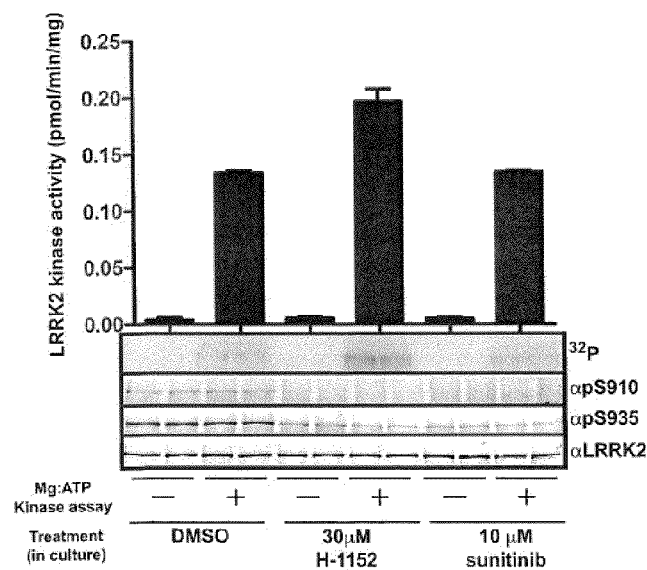
FIG. 6. Evidence that Ser910 and Ser935 phosphorylation is not mediated by LRRK2 autophosphorylation. Endogenous LRRK2 was immunoprecipitated from Swiss 3T3 cells treated with DMSO or 30 μM H1152 or 10 μM sunitinib for 2 h to induce dephosphorylation of Ser 910 and Ser 935. Immunoprecipitates were washed with lysis buffer containing 0.5 M NaCl to remove inhibitor and were then incubated in kinase buffer containing 20 μM Nictide with the presence or absence of magnesium-ATP for 30 min. Following incubation, immunoprecipitates were centrifuged at 8000 rpm for 0.5 min and the supernatant spotted on to P81 paper for measurement of LRRK2 kinase activity. Sample buffer was added to the pelleted beads and LRRK2 S910 and S935 phosphorylation was quantified following immunoblot analysis. A membrane was also subjected to autoradiography to assess LRRK2 autophosphorylation. The minor effect that H-1152 had on LRRK2 kinase assay is not significant.

Evidence that LRRK2 does not autophosphorylate Ser910 and Ser935. LRRK2 possesses marked preference for phosphorylating threonine over serine residues [8], suggesting that Ser910 and Ser935 phosphorylation might not be mediated by autophosphorylation. Consistent with this, other studies investigating LRRK2 autophosphorylation sites have mapped a number of phospho-threonine autophosphorylation sites, but not reported LRRK2 to phosphorylate at Ser910 or Ser935 [16-18]. To further investigate whether endogenous LRRK2 can phosphorylate itself at Ser910 and Ser935, we treated Swiss 3T3 cells with either no drug, or 30 µM H-1152 in order to induce dephosphorylation of Ser910 and Ser935 (FIG. 6). Endogenous LRRK2 was immunoprecipitated, washed to remove drug and immunoprecipitates were incubated in the absence or presence of magnesium-ATP. After 30 min, LRRK2 kinase activity as well as phosphorylation of Ser910 and Ser935 was quantified. These studies revealed that the LRRK2 isolated from H-1152 treated cells was dephosphorylated, and possessed the same activity as LRRK2 isolated from untreated cells indicating that the drug had been removed (FIG. 6). Importantly, we observed no increase in phosphorylation of Ser910 or Ser935 following incubating LRRK2 from H1152 treated cells with magnesium-ATP. The amount of phosphorylation of LRRK2 isolated from non-drug treated cells on Ser910 and Ser935 was also not increased in the autophosphorylation reaction.

Effect of multiple signal transduction inhibitors on Ser910/Ser935 phosphorylation. To gain further insight into the specificity of Ser910 and Ser 935 dephosphorylation HEK293 cells stably expressing GFP-LRRK2 were treated with a panel of 33 kinase inhibitors including those that suppress major signal transduction pathways in cells including PI 3-kinase, mTOR, ERK, p38, JNK and innate immune signalling pathways (FIG. 16). All inhibitors were utilised at the higher limits of concentrations routinely employed in the literature and our unit known to suppress signalling pathways. As expected, 10 µM Sunitinib induced marked dephosphorylation of Ser910 and Ser 935 whilst 32 of the inhibitors tested did not significantly affect dephosphorylation of Ser910/Ser935. Some dephosphorylation of Ser910 and Ser935 was observed with the relatively non specific JNK inhibitor SP600125 which was used at a concentration of 15 µM and is known to inhibit many protein kinases more potently than JNK [34]. It should be noted that the more potent JNK inhibitor AS601245 did not induce dephosphorylation of these sites. Further work will be required to delineate the protein kinase(s) that directly mediate Ser910 and Ser935 phosphorylation.

Disruption of 14-3-3 binding alters cellular localisation of LRRK2. A common role of 14-3-3 proteins is to influence the subcellular localisation of the protein to which it binds. We therefore studied whether 14-3-3 binding might affect LRRK2 cellular localisation. To ensure low level and as uniform as possible expression, we generated Flp-in T-REx 293 cells that stably express wild type and non-14-3-3-binding Ser910/Ser935 mutant forms of full-length GFP-LRRK2. Immunoblot analysis revealed that wild type and mutant GFP-LRRK2 forms were expressed at similar levels (FIG.

8A). We next studied the cellular localisation using confocal microscopy and found, that consistent with a previous report [18], wild type LRRK2 was uniformly distributed throughout the cytosol and excluded from the nucleus (FIG. 8B). In contrast, the non-14-3-3-binding LRRK2[S910A], LRRK2 [S935A] and LRRK2[S910A+S935A] mutants accumulated within cytosolic pools (FIG. 8B).

Characterisation of 14-3-3 binding of 41 LRRK2 disease associated mutants. We next decided to investigate the Ser910/Ser935 phosphorylation and 14-3-3 binding properties of 41 Parkinson's disease forms of LRRK2. The location of the different mutations in LRRK2 analysed is indicated in the FIG. 9 inset. We expressed full-length wild type and mutant forms of LRRK2 with an N-terminal Flag epitope tag in 293 cells. LRRK2 was immunoprecipitated and levels of protein determined by quantitative LICOR-immunoblotting analysis. Similar levels of LRRK2 forms were subjected to immunoblot analysis, which revealed that most of the mutants were phosphorylated at Ser910 and Ser935 to a similar extent as the wild type enzyme and interacted with 14-3-3 (FIG. 9, lower panel). However, Ser910/Ser935 phosphorylation and hence 14-3-3 binding were abolished in four mutants (R1441G, Y1699C, E1874stop and I2020T) (FIG. 9, lower panel). Phosphorylation of Ser910/Ser935 and 14-3-3 binding were significantly reduced in six other mutants (M712V, R1441H, R1441C, A1442P, L1795F and G2385R) (FIG. 9, lower panel).

We also compared the relative protein kinase specific activity of the 41 mutant forms of LRRK2 employing the LRRK-tide peptide substrate [9] (FIG. 5). Consistent with previous work [7-9], LRRK2[G2019S] mutant possessed ~3-fold higher specific activity than wild type LRRK2. Two other mutants LRRK2[R1728H] and LRRK2[T2031S] also exhibited two and four-fold increased activity respectively than wild type LRRK2. Apart from the R1874stop mutation that lacks the kinase domain and is therefore inactive, all other mutants tested possessed similar activity to wild type LRRK2.

Association of 14-3-3 with endogenous LRRK2 is impaired in LRRK2[R1441C] knockin mice. To obtain further evidence that the LRRK2[R144C] Parkinson's disease mutation disrupts 14-3-3 binding, we compared levels of 14-3-3 associated with endogenous LRRK2 derived from previously reported littermate wild type and homozygous LRRK2[R144C] knockin mice [19]. LRRK2 was immunoprecipitated from spleen, kidney and brain from three separate mice of each genotype. Immunoblotting and 14-3-3 overlay analysis demonstrated that level of LRRK2 expression was similar in the wild type and knock-in mice, however the level of Ser910/Ser935 phosphorylation and associated 14-3-3 was markedly reduced in tissues derived from LRRK2 [R1441C] knock-in mice compared to wild type (FIG. 10). The largest effect of the mutation was observed in kidney.

Figures 11A, 11B:
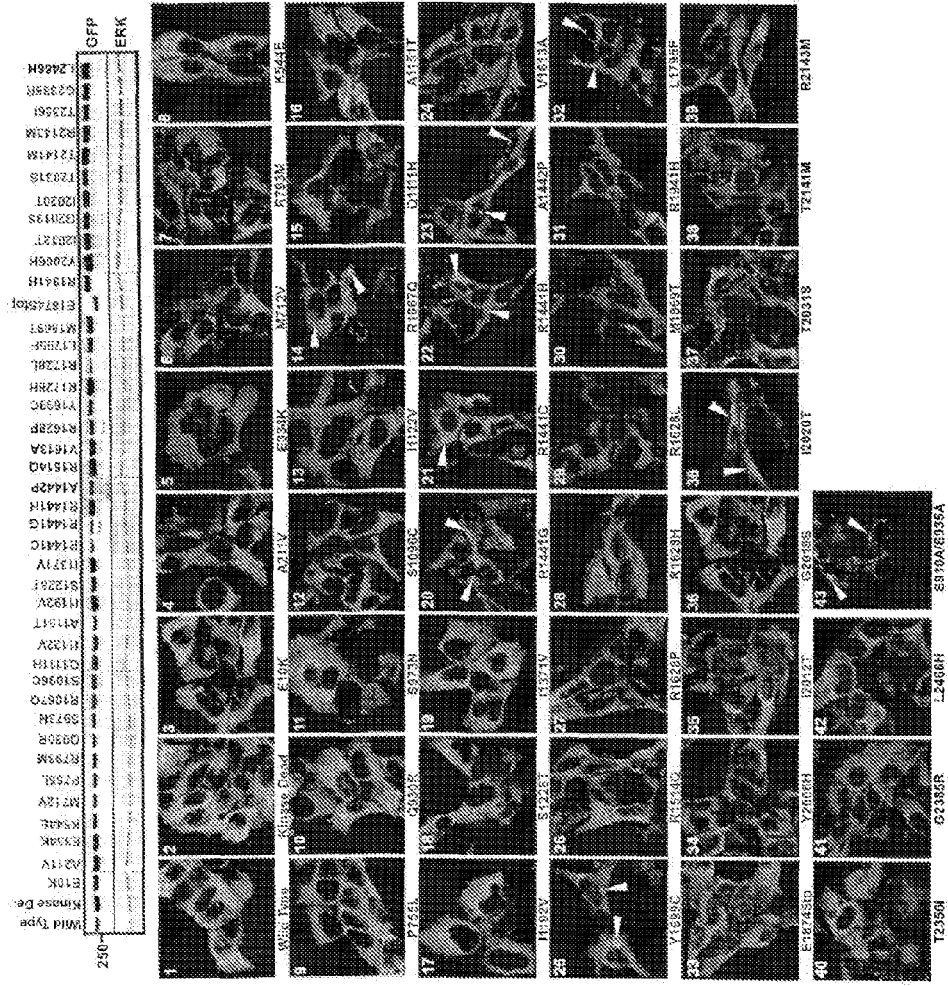

Cellular localisation of 41 mutant forms of LRRK2. To ensure low level and as uniform as possible expression of wild type and mutant forms of full length GFP-LRRK2, we generated the Flp-in T-REx 293 cells that stably express wild type and mutant forms of GFP-LRRK2. Immunoblot analysis revealed that GFP-LRRK2 forms were expressed at relatively similar levels (FIG. 11A). The localisation of wild type, kinase dead and many other LRRK2 mutants studied were uniformly distributed throughout the cytosol and excluded from the nucleus with no accumulation within cytoplasmic pools observed (see FIG. 11B or FIG. 13 to view larger images). Strikingly, most mutants that displayed reduced Ser910/Ser935 phosphorylation and binding to 14-3-3, accumulated within cytosolic pools (R1441C, R1441G, R1441H, A1442P, Y1699C, L1795F, I2020T). Not counting the truncated E1874stop mutant, which displays diffuse cytoplasmic localisation, only two other mutants (M712V and G2385R) displaying reduced Ser910/Ser935 phosphorylation and 14-3-3 binding (FIG. 9) but did not accumulate in cytoplasmic pools (FIG. 11B or FIG. 13). Only a single mutant (R1067Q) was found to interact with 14-3-3 and accumulate within cytoplasmic pools (FIG. 11B or FIG. 13).

Disruption of 14-3-3 binding alters cellular localisation of LRRK2. Mutants of LRRK2 that do not interact with 14-3-3 rather than being diffusely localised throughout the cytoplasm accumulate within cytoplasmic aggregates, as shown in this Example. This prompted us to investigate whether H-1152 treatment induces cytoplasmic re-localisation of GFP-LRRK2 or GFP-LRRK2[G2019S] to discrete cytoplasmic pools (FIG. 14). We employed stable-inducible T-REx cells lines expressing at low levels drug sensitive or drug resistant (A2016T mutant) forms of GFP-LRRK2 or GFP-LRRK2[G2019S]. In untreated cells, GFP-LRRK2 and GFP-LRRK2[G2019S] was diffusely localised throughout the cytoplasm and not observed in the nucleus (FIG. 14A). However, H-1152 treatment induced a marked accumulation of LRRK2 within cytoplasmic pools (FIG. 14A). In accordance with this effect of H-1152 being mediated via inhibition of LRRK2 kinase activity, no cytoplasmic pool accumulation was observed upon treatment of cells expressing drug resistant LRRK2[A2016T] or LRRK2[A2016T+G2019S] with H-1152 (FIG. 4A). As a further control, we studied the localisation of GFP-LRRK2[R1441C] and GFP-LRRK2[Y1699C] that do not bind 14-3-3 and were previously shown to accumulate within cytoplasmic pools [this Example; 33]. We confirmed that these mutants accumulated within cytoplasmic pools-like structures similar to those observed for GFP-LRRK2 and GFP-LRRK2[G2019S] following treatment with H-1152 (compare FIG. 14A & FIG. 14B).

Discussion

The key finding in this paper is that the kinase activity of LRRK2 indirectly controls phosphorylation of Ser910/Ser935 and hence 14-3-3 binding as well as LRRK2 cytoplasmic localisation. In the cell lines we have investigated (Swiss 3T3 (FIG. 4) and HEK-293 (FIG. 5)), phosphorylation of LRRK2 at Ser910 and Ser935 and hence binding to 14-3-3 was reversed by treatment with the structurally diverse H-1152 and sunitinib LRRK2 inhibitors. We have also found that H-1152 induces LRRK2 to accumulate within discrete cytoplasmic pools that are similar to those observed for LRRK2 mutants that do not bind 14-3-3 (FIG. 14B). We conclude that dephosphorylation and cytoplasmic re-localisation results from inhibition of LRRK2 kinase activity, as LRRK2 inhibitors are ineffective at inducing dephosphorylation or re-localisation of drug resistant LRRK2[A2016T] mutants (FIG. 5). The finding that, H-1152 and sunitinib are more potent at inducing Ser910/Ser935 dephosphorylation of LRRK2[G2019S] than wild type LRRK2 (FIG. 5), is also consistent with these drugs inhibiting LRRK2[G2019S] two to four-fold more potently than the wild type LRRK2 [8].

We demonstrate that 14-3-3 isoforms interact with endogenous LRRK2 and this is mediated by phosphorylation of Ser910 and Ser935. 14-3-3 proteins interact dynamically with many intracellular proteins, which exerts a widespread influence on diverse cellular processes. They operate by binding to specific phosphorylated residues on target proteins. The finding that LRRK2 interacts with 14-3-3 isoforms could not be predicted by analysis of the primary sequence, because the residues surrounding the 910 and 935 phosphorylation sites do not adhere to the optimal Mode 1 and 2 consensus binding motifs for a common mode of 14-3-3 interaction [11, 15]. However, many proteins that interact with 14-3-3 do so via diverse non-predictable atypical binding motifs, presumably because other structural features contribute to the interactions [11].

In all cell lines we have investigated (Swiss 3T3 (FIG. 4) and HEK-293 (FIG. 5)), phosphorylation of LRRK2 at Ser910 and Ser935 and hence binding to 14-3-3 was reversed by treatment of cells with the structurally diverse H-1152 and sunitinib LRRK2 inhibitors. We conclude that dephosphorylation results from inhibition of LRRK2 kinase activity, as H-1152 as well as sunitinib is ineffective at inducing dephosphorylation of a drug resistant LRRK2[T2016A] mutant (FIG. 5). Furthermore, H-1152 and sunitinib are more potent at inducing dephosphorylation of LRRK2[G2019S] than wild type LRRK2 (FIG. 5), consistent with these drugs inhibiting LRRK2[G2019S] two to four-fold more potently than the wild type LRRK2.

A key question concerns the mechanism by which LRRK2 controls phosphorylation of Ser910 and Ser935. One possibility is that Ser910 and Ser935 comprise direct LRRK2 autophosphorylation sites. However, our data suggest that dephosphorylated LRRK2 isolated from H-1152 or sunitinib treated cells is unable to phosphorylate itself at Ser910/Ser935 following incubation with magnesium-ATP (FIG. 6). This is consistent with LRRK2 having a marked preference for phosphorylating threonine residues over serine residues as demonstrated by our finding that substituting the phosphorylated Thr residue in an optimal peptide substrate to a Ser residue, abolished phosphorylation by LRRK2 [8]. Furthermore, a number of studies aimed at mapping LRRK2 autophosphorylation sites have not identified Ser910 or Ser935 [16-18]. A global phosphoproteomic study of a melanoma tumour identified phosphorylation of LRRK2 at Ser935 as one of 5600 phosphorylation sites catalogued on 2250 proteins but this was not investigated further [19].

There is significant similarity in the sequences surrounding Ser910 and Ser935 suggesting a single protein kinase may phosphorylate both of these residues (FIG. 3G). An implication of our finding is that the Ser910/Ser935 kinase may be stimulated by LRRK2 and/or the protein phosphatase(s) that acts on these residues is inhibited by LRRK2. In future work it will be important to identify the kinase(s) and/or protein phosphatase(s) that act on Ser910 and Ser935 and to determine whether they are controlled by LRRK2.

Our data suggests that phosphorylation of both Ser910 and Ser935 is required for stable interaction of 14-3-3 with LRRK2 as binding as mutation of either Ser910 or Ser935 abolishes interaction 14-3-3 interaction. 14-3-3 molecules form dimers with each monomer having the ability to interact with a phosphorylated residue [15]. Thus, a 14-3-3 dimer has the capacity to interact with two phosphorylated residues. It is possible that one dimer of 14-3-3 interacts with both phosphorylated Ser910 and phosphorylated Ser935. We also observed that mutation of either Ser910 or Ser935 to an Ala residue induced a significant dephosphorylation the other residue (FIG. 3E). This could be explained if 14-3-3 binding protected LRRK2 from becoming dephosphorylated by a protein phosphatase. Thus abolishing 14-3-3 binding by mutation of either Ser910 or Ser935 would promote dephosphorylation of the other site. 14-3-3 binding to other targets such as phosphatidylinositol 4-kinase III beta [20] or Cdc25C [21] has been shown to protect these enzymes from dephosphorylation, presumably by sterically shielding phosphorylated residues from protein phosphatases.

14-3-3 proteins were originally identified over 42 years ago as acidic proteins that were highly expressed in the brain [31]. Since then 14-3-3 proteins have been implicated in the regulation of numerous neurological disorders including Parkinson's disease [26, 27]. For example, 14-3-3 eta binds to parkin, a protein mutated in autosomal recessive juvenile parkinsonism, and negatively regulates its E3 ligase activity [22]. 14-3-3 proteins interact with alpha-synuclein [23] and have been found in Lewy bodies in brains of patients with Parkinson's disease [24]. Additionally, 14-3-3 theta, epsilon and gamma was recently shown to suppress the toxic effects of alpha-synuclein overexpression in a cell based model of neurotoxicity [25]. Our data suggests that 14-3-3 binding to LRRK2 may be relevant to Parkinson's disease as strikingly 10 out of 41 mutations studied displayed reduced phosphorylation of Ser910/Ser935 and binding to 14-3-3 isoforms (FIG. 12).

Our data suggest that the 14-3-3 interaction does not control LRRK2 protein kinase activity, as mutation of Ser910 and/or Ser935 does not influence LRRK2 catalytic activity (FIG. 3D). Furthermore, treatment of cells with H-1152 or sunitinib induced dephosphorylation of Ser910 and Ser935 as well as disrupting 14-3-3 binding, but did not affect endogenous LRRK2 kinase activity (FIG. 6). 14-3-3 binding to LRRK2 may impact on its interaction with a substrate or other regulators or may influence LRRK2 stability or cellular localisation. Our experiments indicate that 14-3-3 binding influences the cytoplasmic localisation of LRRK2, as disruption of 14-3-3 binding by mutation of Ser910/Ser935 caused LRRK2 to accumulate within cytoplasmic pools. Previous work has revealed that LRRK2 mutants including LRRK2 [R1441C] and LRRK2[Y1699C] when expressed in cells accumulate within cytoplasmic pools [33, 35, 36], a finding we were able to confirm in this study (FIG. 11B or FIG. 13). These cytoplasmic pools were suggested to comprise aggregates of misfolded unstable LRRK2 protein [35]. If this were the case it may suggest that 14-3-3 plays a role in stabilising LRRK2. Significantly, we found that seven out of eight mutations that accumulated within cytoplasmic pools displayed reduced Ser910/Ser935 phosphorylation and binding to 14-3-3 under conditions in which wild type LRRK2 and most other LRRK2 mutants analysed bound 14-3-3 and did not accumulate within cytosolic pools (FIG. 11B). We also validate these findings by demonstrating that Ser910/Ser935 phosphorylation and 14-3-3 binding is markedly reduced in three mouse tissues derived from homozygous R1441C knockin mice that display impaired dopaminergic neurotransmission [37].

In FIG. 12 we subdivide the 41 LRRK2 mutations we have analysed into six groups based on the impact that the mutations analysed in this study have on protein kinase activity, Ser910/Ser935 phosphorylation and 14-3-3-binding as well as cellular localisation. Only three out of the 41 mutations analysed markedly enhanced LRRK2 protein kinase two to four-fold. Strikingly, the LRRK2[T2031S] mutation was more active than the LRRK2[G2019S] mutant, displaying nearly 4-fold higher activity than wild type LRRK2. The LRRK2[T2031S] mutation has only been reported in a single Spanish patient with a family history of PD [38]. Interestingly, Thr2031 lies within the T-loop of the LRRK2 kinase domain, a region where many kinases are activated by phosphorylation. A recent study has suggested that a catalytically active fragment of LRRK2 expressed in insect cells autophosphorylates at several residues including Thr2031 [16], although we have thus far never been able to observe phosphorylation of this site in endogenous or overexpressed LRRK2. We have found that changing Thr2031 to Ala to prevent phosphorylation led to a similar increase in activity as the T2031S mutation (RJN data not shown) and mutation to Glu to mimic phosphorylation inactivates LRRK2 (ND data not shown). Further work is warranted to understand the role of Thr2031 and how its mutation to Ser and/or phosphorylation or other covalent modification impacts on LRRK2 catalytic activity. The LRRK2[R1728H] mutation displayed 2-fold increased in kinase activity and was identified in a single patient with a family history of PD [39]. The Arg1728 residue is located outside the kinase domain in the COR domain (FIG. 9).

Figure 7:
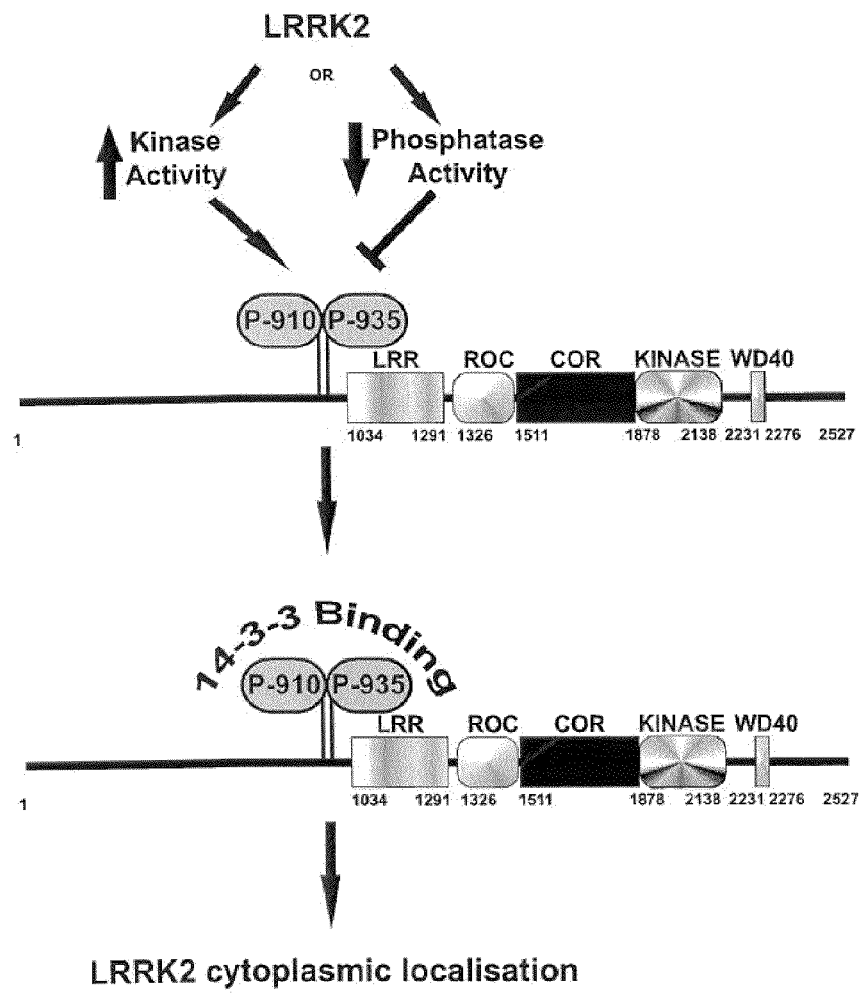
FIG. 7. Proposed model of how LRRK2 controls Ser910 and Ser935 phosphorylation leading to 14-3-3 binding. Our data suggest that LRRK2 kinase activity stimulates the activity of a protein kinase or inhibits the activity of a protein phosphatase that acts on Ser910 and Ser935. This enables LRRK2 to interact with 14-3-3 isoforms and stabilises diffuse cytoplasmic localisation of LRRK2. Treatment of cells with LRRK2 inhibitors thus leads to dephosphorylation of Ser910 and Ser935 and dissociation of 14-3-3 isoforms. Our findings indicate that LRRK2 phosphorylation of Ser910 and Ser935 as well as 14-3-3 binding could be employed as a biomarker to benchmark efficacy of LRRK2 inhibitors that are being developed.

In FIG. 7 we present a model by which phosphorylation of Ser910 and Ser935 is dependent upon LRRK2 activity and mediates binding to 14-3-3 isoforms. Phosphorylation of LRRK2 at Ser910 and Ser935, or 14-3-3 binding, can be deployed as a cell-based readout to evaluate the relative potency of LRRK2 inhibitors being developed. This assay can be deployed in cell lines or tissues of animals or humans treated with LRRK2 inhibitors. For human patients administered LRRK2 inhibitors in a clinical trial, the phosphorylation status of LRRK2 at Ser910 and Ser935 in the blood could be employed as a biomarker of LRRK2 inhibitor efficacy (as LRRK2 is strongly expressed in blood cells). We believe this to be the first, simple, cell-based system that can be used to assess the efficacy of LRRK2 protein kinase inhibitors, based on measuring phosphorylation of an endogenous LRRK2 target.

REFERENCES

1 Zimprich, A., Biskup, S., Leitner, P., Lichtner, P., Farrer, M., Lincoln, S., Kachergus, J., Hulihan, M., Uitti, R. J., Calne, D. B., Stoessl, A. J., Pfeiffer, R. F., Patenge, N., Carbajal, I. C., Vieregge, P., Asmus, F., Muller-Myhsok, B., Dickson, D. W., Meitinger, T., Strom, T. M., Wszolek, Z. K. and Gasser, T. (2004) Mutations in LRRK2 cause autosomal-dominant parkinsonism with pleomorphic pathology. Neuron. 44, 601-607

2 Paisan-Ruiz, C., Jain, S., Evans, E. W., Gilks, W. P., Simon, J., van der Brug, M., Lopez de Munain, A., Aparicio, S., Gil, A. M., Khan, N., Johnson, J., Martinez, J. R., Nicholl, D., Carrera, I. M., Pena, A. S., de Silva, R., Lees, A., Marti-Masso, J. F., Perez-Tur, J., Wood, N. W. and Singleton, A. B. (2004) Cloning of the gene containing mutations that cause PARK8-linked Parkinson's disease. Neuron. 44, 595-600

3 Healy, D. G., Falchi, M., O'Sullivan, S. S., Bonifati, V., Durr, A., Bressman, S., Brice, A., Aasly, J., Zabetian, C. P., Goldwurm, S., Ferreira, J. J., Tolosa, E., Kay, D. M., Klein, C., Williams, D. R., Marras, C., Lang, A. E., Wszolek, Z. K., Berciano, J., Schapira, A. H., Lynch, T., Bhatia, K. P., Gasser, T., Lees, A. J. and Wood, N. W. (2008) Phenotype, genotype, and worldwide genetic penetrance of LRRK2-associated Parkinson's disease: a case-control study. Lancet Neurol. 7, 583-590

4 Mata, I. F., Wedemeyer, W. J., Farrer, M. J., Taylor, J. P. and Gallo, K. A. (2006) LRRK2 in Parkinson's disease: protein domains and functional insights. Trends Neurosci. 29, 286-293

5 Biskup, S, and West, A. B. (2008) Zeroing in on LRRK2-linked pathogenic mechanisms in Parkinson's disease. Biochim Biophys Acta 6 Greggio, E. and Cookson, M. R. (2009) Leucine Rich Repeat Kinase 2 mutations and Parkinson's disease: Three Questions. ASN Neuro. In Press 7 Jaleel, M., Nichols, R. J., Deak, M., Campbell, D. G., Gillardon, F., Knebel, A. and Alessi, D. R. (2007) LRRK2 phosphorylates moesin at threonine-558: characterization of how Parkinson's disease mutants affect kinase activity. Biochem J. 405, 307-317

8 Nichols, R. J., Dzamko, N., Hutti, J. E., Cantley, L. C., Deak, M., Moran, J., Bamborough, P., Reith, A. D. and Alessi, D. R. (2009) Substrate specificity and inhibitors of LRRK2, a protein kinase mutated in Parkinson's disease. Biochem J. 424, 47-60

9 Covy, J. P. and Giasson, B. I. (2009) Identification of compounds that inhibit the kinase activity of leucine-rich repeat kinase 2. Biochem Biophys Res Commun. 378, 473-477

10 Anand, V. S., Reichling, L. J., Lipinski, K., Stochaj, W., Duan, W., Kelleher, K., Pungaliya, P., Brown, E. L., Reinhart, P. H., Somberg, R., Hirst, W. D., Riddle, S. M. and Steven, P. B. (2009) Investigation of leucine-rich repeat kinase 2: enzymological properties and novel assays. Febs J. 276, 466-478

11 Mackintosh, C. (2004) Dynamic interactions between 14-3-3 proteins and phosphoproteins regulate diverse cellular processes. Biochem J. 381, 329-342

12 Reed, S. E., Staley, E. M., Mayginnes, J. P., Pintel, D. J. and Tullis, G. E. (2006) Transfection of mammalian cells using linear polyethylenimine is a simple and effective means of producing recombinant adeno-associated virus vectors. J Virol Methods. 138, 85-98

13 Moorhead, G., Douglas, P., Cotelle, V., Harthill, J., Morrice, N., Meek, S., Deiting, U., Stitt, M., Scarabel, M., Aitken, A. and MacKintosh, C. (1999) Phosphorylation-dependent interactions between enzymes of plant metabolism and 14-3-3 proteins. Plant J. 18, 1-12

14 Wang, L., Xie, C., Greggio, E., Parisiadou, L., Shim, H., Sun, L., Chandran, J., Lin, X., Lai, C., Yang, W. J., Moore, D. J., Dawson, T. M., Dawson, V. L., Chiosis, G., Cookson, M. R. and Cai, H. (2008) The chaperone activity of heat shock protein 90 is critical for maintaining the stability of leucine-rich repeat kinase 2. J. Neurosci. 28, 3384-3391

15 Yaffe, M. B., Rittinger, K., Volinia, S., Caron, P. R., Aitken, A., Leffers, H., Gamblin, S. J., Smerdon, S. J. and Cantley, L. C. (1997) The structural basis for 14-3-3:phosphopeptide binding specificity. Cell. 91, 961-971

16 Greggio, E., Taymans, J. M., Zhen, E. Y., Ryder, J., Vancraenenbroeck, R., Beilina, A., Sun, P., Deng, J., Jaffe, H., Baekelandt, V., Merchant, K. and Cookson, M. R. (2009) The Parkinson's disease kinase LRRK2 autophosphorylates its GTPase domain at multiple sites. Biochem Biophys Res Commun. 389, 449-454

17 Kamikawaji, S., Ito, G. and Iwatsubo, T. (2009) Identification of the autophosphorylation sites of LRRK2. Biochemistry. 48, 10963-10975

18 Gloeckner, C. J., Schumacher, A., Boldt, K. and Ueffing, M. (2009) The Parkinson disease-associated protein kinase LRRK2 exhibits MAPKKK activity and phosphorylates MKK3/6 and MKK4/7, in vitro. J. Neurochem. 109, 959-968

19 Zanivan, S., Gnad, F., Wickstrom, S. A., Geiger, T., Macek, B., Cox, J., Fassler, R. and Mann, M. (2008) Solid tumor proteome and phosphoproteome analysis by high resolution mass spectrometry. J Proteome Res. 7, 5314-5326

20 Hausser, A., Link, G., Hoene, M., Russo, C., Selchow, O. and Pfizenmaier, K. (2006) Phospho-specific binding of 14-3-3 proteins to phosphatidylinositol 4-kinase III beta protects from dephosphorylation and stabilizes lipid kinase activity. J Cell Sci. 119, 3613-3621

21 Hutchins, J. R., Dikovskaya, D. and Clarke, P. R. (2002) Dephosphorylation of the inhibitory phosphorylation site S287 in *Xenopus* Cdc25C by protein phosphatase-2A is inhibited by 14-3-3 binding. FEBS Lett. 528, 267-271

22 Sato, S., Chiba, T., Sakata, E., Kato, K., Mizuno, Y., Hattori, N. and Tanaka, K. (2006) 14-3-3eta is a novel regulator of parkin ubiquitin ligase. EMBO J. 25, 211-221

23. Ostrerova, N., Petrucelli, L., Farrer, M., Mehta, N., Choi, P., Hardy, J. and Wolozin, B. (1999) alpha-Synuclein shares physical and functional homology with 14-3-3 proteins. J. Neurosci. 19, 5782-5791
24. Ubl, A., Berg, D., Holzmann, C., Kruger, R., Berger, K., Arzberger, T., Bornemann, A. and Riess, O. (2002) 14-3-3 protein is a component of Lewy bodies in Parkinson's disease-mutation analysis and association studies of 14-3-3 eta. Brain Res Mol Brain Res. 108, 33-39
25. Yacoubian, T. A., Slone, S. R., Harrington, A. J., Hamamichi, S., Schieltz, J. M., Caldwell, G. A. and Standaert, D. G. (2010) Differential neuroprotective effects of 14-3-3 proteins in models of Parkinson's disease. Cell Death and Disease. 1, e2
26. Chen, H. K., Fernandez-Funez, P., Acevedo, S. F., Lam, Y. C., Kaytor, M. D., Fernandez, M. H., Aitken, A., Skoulakis, E. M., Orr, H. T., Botas, J. and Zoghbi, H. Y. (2003) Interaction of Akt-phosphorylated ataxin-1 with 14-3-3 mediates neurodegeneration in spinocerebellar ataxia type 1. Cell. 113, 457-468
27. Berg, D., Holzmann, C. and Riess, O. (2003) 14-3-3 proteins in the nervous system. Nat Rev Neurosci. 4, 752-762
28. Cox, J. and Mann, M. (2008) MaxQuant enables high peptide identification rates, individualized p.p.b.-range mass accuracies and proteome-wide protein quantification. Nat. Biotechnol. 26, 1367-1372
29. Goodman, K. B., Cui, H., Dowdell, S. E., Gaitanopoulos, D. E., Ivy, R. L., Sehon, C. A., Stavenger, R. A., Wang, G. Z., Viet, A. Q., Xu, W., Ye, G., Semus, S. F., Evans, C., Fries, H. E., Jolivette, L. J., Kirkpatrick, R. B., Dul, E., Khandekar, S. S., Yi, T., Jung, D. K., Wright, L. L., Smith, G. K., Behm, D. J., Bentley, R., Doe, C. P., Hu, E. and Lee, D. (2007) Development of dihydropyridone indazole amides as selective Rho-kinase inhibitors. J Med Chem. 50, 6-9
30. Dubois, F., Vandermoere, F., Gernez, A., Murphy, J., Toth, R., Chen, S., Geraghty, K. M., Morrice, N. A. and Mackintosh, C. (2009) Differential 14-3-3-affinity capture reveals new downstream targets of PI 3-kinase signaling. Mol Cell Proteomics
31. M Moore, B. W. and Perez, V. J. (1967) Specific acidic proteins of the nervous system. Physiological and Biochemical Aspects of Nervous Integration (F. D Carlson, ed). Wood Hole, Mass.; Prentice-Hall, Inc, 343-359
32. Anand, V. S, and Braithwaite, S. P. (2009) LRRK2 in Parkinson's disease: biochemical functions. FEBS J. 276, 6428-6435
33. Alegre-Abarrategui, J., Christian, H., Lufino, M. M., Mutihac, R., Venda, L. L., Ansorge, O. and Wade-Martins, R. (2009) LRRK2 regulates autophagic activity and localizes to specific membrane microdomains in a novel human genomic reporter cellular model. Hum Mol. Genet. 18, 4022-4034
34. Bain, J., Plater, L., Elliott, M., Shpiro, N., Hastie, C. J., McLauchlan, H., Klevernic, I., Arthur, J. S., Alessi, D. R. and Cohen, P. (2007) The selectivity of protein kinase inhibitors: a further update. Biochem J. 408, 297-315
35. Greggio, E., Jain, S., Kingsbury, A., Bandopadhyay, R., Lewis, P., Kaganovich, A., van der Brug, M. P., Beilina, A., Blackinton, J., Thomas, K. J., Ahmad, R., Miller, D. W., Kesavapany, S., Singleton, A., Lees, A., Harvey, R. J., Harvey, K. and Cookson, M. R. (2006) Kinase activity is required for the toxic effects of mutant LRRK2/dardarin. Neurobiol Dis. 23, 329-341
36. Smith, W. W., Pei, Z., Jiang, H., Moore, D. J., Liang, Y., West, A. B., Dawson, V. L., Dawson, T. M. and Ross, C. A. (2005) Leucine-rich repeat kinase 2 (LRRK2) interacts with parkin, and mutant LRRK2 induces neuronal degeneration. Proc Natl Acad Sci USA. 102, 18676-18681
37. Tong, Y., Pisani, A., Martella, G., Karouani, M., Yamaguchi, H., Pothos, E. N. and Shen, J. (2009) R1441C mutation in LRRK2 impairs dopaminergic neurotransmission in mice. Proc Natl Acad Sci USA. 106, 14622-14627
38. Lesage, S., Janin, S., Lohmann, E., Leutenegger, A. L., Leclere, L., Viallet, F., Pollak, P., Durif, F., Thobois, S., Layet, V., Vidailhet, M., Agid, Y., Durr, A., Brice, A., Bonnet, A. M., Borg, M., Broussolle, E., Damier, P., Destee, A., Martinez, M., Penet, C., Rasco, O., Tison, F., Tranchan, C. and Verin, M. (2007) LRRK2 exon 41 mutations in sporadic Parkinson disease in Europeans. Arch Neurol. 64, 425-430
39. Paisan-Ruiz, C., Nath, P., Washecka, N., Gibbs, J. R. and Singleton, A. B. (2008) Comprehensive analysis of LRRK2 in publicly available Parkinson's disease cases and neurologically normal controls. Hum Mutat. 29, 485-490
40. Nichols, R. J., Dzamko, N., Hutti, J. E., Cantley, L. C., Deak, M., Moran, J., Bamborough, P., Reith, A. D. and Alessi, D. R. (2009) Substrate specificity and inhibitors of LRRK2, a protein kinase mutated in Parkinson's disease. Biochem J. 424, 47-60
41. Raynaud, F. I., Eccles, S. A., Patel, S., Alix, S., Box, G., Chuckowree, I., Folkes, A., Gowan, S., De Haven Brandon, A., Di Stefano, F., Hayes, A., Henley, A. T., Lensun, L., Pergl-Wilson, G., Robson, A., Saghir, N., Zhyvoloup, A., McDonald, E., Sheldrake, P., Shuttleworth, S., Valenti, M., Wan, N. C., Clarke, P. A. and Workman, P. (2009) Biological properties of potent inhibitors of class I phosphatidylinositide 3-kinases: from PI-103 through PI-540, PI-620 to the oral agent GDC-0941. Mol Cancer Ther. 8, 1725-1738
42. Fan, Q. W., Knight, Z. A., Goldenberg, D. D., Yu, W., Mostov, K. E., Stokoe, D., Shokat, K. M. and Weiss, W. A. (2006) A dual PI3 kinase/mTOR inhibitor reveals emergent efficacy in glioma. Cancer Cell. 9, 341-349
43. Feldman, R. I., Wu, J. M., Polokoff, M. A., Kochanny, M. J., Dinter, H., Zhu, D., Biroc, S. L., Alicke, B., Bryant, J., Yuan, S., Buckman, B. O., Lentz, D., Ferrer, M., Whitlow, M., Adler, M., Finster, S., Chang, Z. and Arnaiz, D. O. (2005) Novel small molecule inhibitors of 3-phosphoinositide-dependent kinase-1. J Biol Chem. 280, 19867-19874
44. Logie, L., Ruiz-Alcaraz, A. J., Keane, M., Woods, Y. L., Bain, J., Marquez, R., Alessi, D. R. and Sutherland, C. (2007) Characterization of a protein kinase B inhibitor in vitro and in insulin-treated liver cells. Diabetes. 56, 2218-2227
45. Garcia-Martinez, J. M., Moran, J., Clarke, R. G., Gray, A., Cosulich, S. C., Chresta, C. M. and Alessi, D. R. (2009) Ku-0063794 is a specific inhibitor of the mammalian target of rapamycin (mTOR). Biochem J. 421, 29-42
46. Ring, D. B., Johnson, K. W., Henriksen, E. J., Nuss, J. M., Goff, D., Kinnick, T. R., Ma, S. T., Reeder, J. W., Samuels, I., Slabiak, T., Wagman, A. S., Hammond, M. E. and Harrison, S. D. (2003) Selective glycogen synthase kinase 3 inhibitors potentiate insulin activation of glucose transport and utilization in vitro and in vivo. Diabetes. 52, 588-595
47. Wilhelm, S. M., Carter, C., Tang, L., Wilkie, D., McNabola, A., Rong, H., Chen, C., Zhang, X., Vincent, P., McHugh, M., Cao, Y., Shujath, J., Gawlak, S., Eveleigh, D., Rowley, B., Liu, L., Adnane, L., Lynch, M., Auclair, D., Taylor, I., Gedrich, R., Voznesensky, A., Riedl, B., Post, L. E., Bollag, G. and Trail, P. A. (2004) BAY 43-9006 exhibits broad spectrum oral antitumor activity and targets the RAF/MEK/ERK pathway and receptor tyrosine kinases involved in tumor progression and angiogenesis. Cancer Res. 64, 7099-7109

48. Barrett, S. D., Bridges, A. J., Dudley, D. T., Saltiel, A. R., Fergus, J. H., Flamme, C. M., Delaney, A. M., Kaufman, M., LePage, S., Leopold, W. R., Przybranowski, S. A., Sebolt-Leopold, J., Van Becelaere, K., Doherty, A. M., Kennedy, R. M., Marston, D., Howard, W. A., Jr., Smith, Y., Warmus, J. S, and Tecle, H. (2008) The discovery of the benzhydroxamate MEK inhibitors CI-1040 and PD 0325901. Bioorg Med Chem. Lett. 18, 6501-6504

49. Sapkota, G. P., Cummings, L., Newell, F. S., Armstrong, C., Bain, J., Frodin, M., Grauert, M., Hoffmann, M., Schnapp, G., Steegmaier, M., Cohen, P. and Alessi, D. R. (2007) BI-D1870 is a specific inhibitor of the p90 RSK (ribosomal S6 kinase) isoforms in vitro and in vivo. Biochem J. 401, 29-38

50. Pargellis, C., Tong, L., Churchill, L., Cirillo, P. F., Gilmore, T., Graham, A. G., Grob, P. M., Hickey, E. R., Moss, N., Pay, S, and Regan, J. (2002) Inhibition of p38 MAP kinase by utilizing a novel allosteric binding site. Nat Struct Biol. 9, 268-272

51. Cuenda, A., Rouse, J., Doza, Y. N., Meier, R., Cohen, P., Gallagher, T. F., Young, P. R. and Lee, J. C. (1995) SB 203580 is a specific inhibitor of a MAP kinase homologue which is stimulated by cellular stresses and interleukin-1. FEBS Lett. 364, 229-233

52. Gaillard, P., Jeanclaude-Etter, I., Ardissone, V., Arkinstall, S., Cambet, Y., Camps, M., Chabert, C., Church, D., Cirillo, R., Gretener, D., Halazy, S., Nichols, A., Szyndralewiez, C., Vitte, P. A. and Gotteland, J. P. (2005) Design and synthesis of the first generation of novel potent, selective, and in vivo active (benzothiazol-2-yl)acetonitrile inhibitors of the c-Jun N-terminal kinase. J Med. Chem. 48, 4596-4607

53. Bennett, B. L., Sasaki, D. T., Murray, B. W., O'Leary, E. C., Sakata, S. T., Xu, W., Leisten, J. C., Motiwala, A., Pierce, S., Satoh, Y., Bhagwat, S. S., Manning, A. M. and Anderson, D. W. (2001) SP600125, an anthrapyrazolone inhibitor of Jun Nterminal kinase. Proc Natl Acad Sci USA. 98, 13681-13686

54. Burke, J. R., Pattoli, M. A., Gregor, K. R., Brassil, P. J., MacMaster, J. F., McIntyre, K. W., Yang, X., Iotzova, V. S., Clarke, W., Strnad, J., Qiu, Y. and Zusi, F. C. (2003) BMS-345541 is a highly selective inhibitor of I kappa B kinase that binds at an allosteric site of the enzyme and blocks NF-kappa B-dependent transcription in mice. J Biol. Chem. 278, 1450-1456

55. Castro, A. C., Dang, L. C., Soucy, F., Grenier, L., Mazdiyasni, H., Hottelet, M., Parent, L., Pien, C., Palombella, V. and Adams, J. (2003) Novel IKK inhibitors: beta-carbolines. Bioorg Med Chem. Lett. 13, 2419-2422

56. Hu, Y., Green, N., Gavrin, L. K., Janz, K., Kaila, N., Li, H. Q., Thomason, J. R., Cuozzo, J. W., Hall, J. P., Hsu, S., Nickerson-Nutter, C., Telliez, J. B., Lin, L. L. and Tam, S. (2006) Inhibition of Tp12 kinase and TNFalpha production with quinoline-3-carbonitriles for the treatment of rheumatoid arthritis. Bioorg Med Chem. Lett. 16, 6067-6072

57. Degterev, A., Hitomi, J., Germscheid, M., Ch'en, I. L., Korkina, O., Teng, X., Abbott, D., Cuny, G. D., Yuan, C., Wagner, G., Hedrick, S. M., Gerber, S. A., Lugovskoy, A. and Yuan, J. (2008) Identification of RIP1 kinase as a specific cellular target of necrostatins. Nat Chem. Biol. 4, 313-321

58. Leemhuis, J., Boutillier, S., Schmidt, G. and Meyer, D. K. (2002) The protein kinase A inhibitor H89 acts on cell morphology by inhibiting Rho kinase. J Pharmacol Exp Ther. 300, 1000-1007

59. Muid, R. E., Dale, M. M., Davis, P. D., Elliott, L. H., Hill, C. H., Kumar, H., Lawton, G., Twomey, B. M., Wadsworth, J., Wilkinson, S. E. and et al. (1991) A novel conformationally restricted protein kinase C inhibitor, Ro 31-8425, inhibits human neutrophil superoxide generation by soluble, particulate and post-receptor stimuli. FEBS Lett. 293, 169-172

60. Gschwendt, M., Muller, H. J., Kielbassa, K., Zang, R., Kittstein, W., Rincke, G. and Marks, F. (1994) Rottlerin, a novel protein kinase inhibitor. Biochem Biophys Res Commun. 199, 93-98

61. Tokumitsu, H., Inuzuka, H., Ishikawa, Y. and Kobayashi, R. (2003) A single amino acid difference between alpha and beta Ca2+/calmodulin-dependent protein kinase kinase dictates sensitivity to the specific inhibitor, STO-609. J Biol. Chem. 278, 10908-10913

62. Zhou, G., Myers, R., Li, Y., Chen, Y., Shen, X., Fenyk-Melody, J., Wu, M., Ventre, J., Doebber, T., Fujii, N., Musi, N., Hirshman, M. F., Goodyear, L. J. and Moller, D. E. (2001) Role of AMP-activated protein kinase in mechanism of metformin action. J Clin Invest. 108, 1167-1174

63. Meydan, N., Grunberger, T., Dadi, H., Shahar, M., Arpaia, E., Lapidot, Z., Leeder, J. S., Freedman, M., Cohen, A., Gazit, A., Levitzki, A. and Roifman, C. M. (1996) Inhibition of acute lymphoblastic leukaemia by a Jak-2 inhibitor. Nature. 379, 645-648

64. Hanke, J. H., Gardner, J. P., Dow, R. L., Changelian, P. S., Brissette, W. H., Weringer, E. J., Pollok, B. A. and Connelly, P. A. (1996) Discovery of a novel, potent, and Src family-selective tyrosine kinase inhibitor. Study of Lck- and FynTdependent T cell activation. J Biol. Chem. 271, 695-701

65. Nagao, M., Kaziro, Y. and Itoh, H. (1999) The Src family tyrosine kinase is involved in Rho-dependent activation of c-Jun N-terminal kinase by Galpha12. Oncogene. 18, 4425-4434

66. Song, Y., Kesuma, D., Wang, J., Deng, Y., Duan, J., Wang, J. H. and Qi, R. Z. (2004) Specific inhibition of cyclin-dependent kinases and cell proliferation by harmine. Biochem Biophys Res Commun. 317, 128-132

67. Meijer, L., Borgne, A., Mulner, O., Chong, J. P., Blow, J. J., Inagaki, N., Inagaki, M., Delcros, J. G. and Moulinoux, J. P. (1997) Biochemical and cellular effects of roscovitine, a potent and selective inhibitor of the cyclin-dependent kinases cdc2, cdk2 and cdk5. Eur J. Biochem. 243, 527-536

68. Blake, R. A., Broome, M. A., Liu, X., Wu, J., Gishizky, M., Sun, L. and Courtneidge, S. A. (2000) SU6656, a selective src family kinase inhibitor, used to probe growth factor signaling. Mol Cell Biol. 20, 9018-9027

69. Harrington, E. A., Bebbington, D., Moore, J., Rasmussen, R. K., Ajose-Adeogun, A. O., Nakayama, T., Graham, J. A., Demur, C., Hercend, T., Diu-Hercend, A., Su, M., Golec, J. M. and Miller, K. M. (2004) VX-680, a potent and selective small-molecule inhibitor of the Aurora kinases, suppresses tumor growth in vivo. Nat. Med. 10, 262-267

70. Holder, S., Zemskova, M., Zhang, C., Tabrizizad, M., Bremer, R., Neidigh, J. W. and Lilly, M. B. (2007) Characterization of a potent and selective small-molecule inhibitor of the PIM1 kinase. Mol Cancer Ther. 6, 163-172

71. Hardcastle, I. R., Cockcroft, X., Curtin, N. J., El-Murr, M. D., Leahy, J. J., Stockley, M., Golding, B. T., Rigoreau, L., Richardson, C., Smith, G. C. and Griffin, R. J. (2005)

Discovery of potent chromen-4-one inhibitors of the DNA-dependent protein kinase (DNA-PK) using a small-molecule library approach. J Med. Chem. 48, 7829-7846

72. Steegmaier, M., Hoffmann, M., Baum, A., Lenart, P., Petronczki, M., Krssak, M., Gurtler, U., Garin-Chesa, P., Lieb, S., Quant, J., Grauert, M., Adolf, G. R., Kraut, N., Peters, J. M. and Rettig, W. J. (2007) BI 2536, a potent and selective inhibitor of polo-like kinase 1, inhibits tumor growth in vivo. Curr Biol. 17, 316-322

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The invention claimed is:

1. A method for assessing the effect of a test compound on LRRK2 in a cell-based system, the method comprising the steps of:
   a) assessing the effect of exposing the cell-based system comprising LRRK2 to the test compound on the phosphorylation state of Ser910 and/or Ser935 of the LRRK2; and/or
   b) assessing the effect of exposing the cell-based system comprising LRRK2 to the test compound on the binding of the LRRK2 to a 14-3-3 polypeptide and selecting a compound as being considered to have an inhibitory effect on LRRK2 in the cell-based system, wherein a test compound is so selected if the binding of the LRRK2 to the 14-3-3 polypeptide is reduced following exposure; and/or
   c) assessing the effect of exposing the cell-based system comprising LRRK2 to the test compound on the subcellular localization of LRRK2,
   wherein a test compound is selected as inhibitory if the accumulation of LRRK2 in cytoplasmic pools is increased following the exposure.

2. The method of claim 1, further comprising the step of selecting a compound as being considered to have an inhibitory effect on LRRK2 in a cell-based system, wherein a test compound is so selected if the phosphorylation of Ser910 and/or Ser935 of the LRRK2 is reduced following the exposure.

3. The method of claim 1, wherein phosphorylation of Ser910 is assessed using an antibody that binds specifically to LRRK2 phosphorylated at Ser910 or an antibody that binds specifically to LRRK2 that is not phosphorylated at Ser910.

4. The method of claim 1, wherein phosphorylation of Ser935 is assessed using an antibody that binds specifically to LRRK2 phosphorylated at Ser935 or an antibody that binds specifically to LRRK2 that is not phosphorylated at Ser935.

5. The method of claim 1, wherein binding of the LRRK2 to the 14-3-3 polypeptide is assessed using fluorescence resonance energy transfer (FRET).

6. The method of claim 1, wherein the cell based system is an in vitro cell system.

7. The method of claim 1, wherein the cell based system is an ex vivo cell system.

8. The method of claim 1, wherein the cell based system is an in vivo system.

9. The method of claim 8, wherein the cell-based system comprising LRRK2 has been exposed to the test compound in a test animal.

10. The method of claim 9, wherein the assessing of the phosphorylation state of Ser910 and/or Ser935 of the LRRK2; and/or the assessing of the binding of the LRRK2 to the 14-3-3 polypeptide; and/or the assessing of accumulation of LRRK2 in cytoplasmic pools is performed on cells obtained from the test animal.

11. The method of claim 10, wherein the cells obtained from the test animal are cells obtained in blood from the test animal.

12. The method of claim 1, wherein the cell based system is a broken cell system.

13. The method of claim 1, wherein the cell based system is a lymphoblastoid cell-based system.

14. A method of assessing the effect of a test compound on LRRK2 in a cell-based system, the method comprising the step of exposing the cell-based system to the test compound and assessing the phosphorylation state of Ser910 and/or Ser935 of the LRRK2, wherein the phosphorylation state of Ser910 and/or Ser935 is assessed with:
   1) an antibody that binds specifically to LRRK2 phosphorylated at Ser910, or an antibody that binds specifically to LRRK2 that is not phosphorylated at Ser910; and/or
   2) an antibody that binds specifically to LRRK2 phosphorylated at Ser935, or an antibody that binds specifically to LRRK2 that is not phosphorylated at Ser935.

* * * * *